(12) United States Patent
England et al.

(10) Patent No.: US 8,809,031 B2
(45) Date of Patent: Aug. 19, 2014

(54) ENHANCED AMYLASE PRODUCTION BY N-TERMINAL ADDITION TO MATURE AMYLASE PROTEIN

(75) Inventors: George England, Redwood City, CA (US); Marc Kolkman, Oegstgeest (NL); Casper Vroemen, Oegstgeest (NL)

(73) Assignee: Danisco US Inc., Palo Alto, CA (US)

( * ) Notice: Subject to any disclaimer, the term of this patent is extended or adjusted under 35 U.S.C. 154(b) by 874 days.

(21) Appl. No.: 12/596,821

(22) PCT Filed: Mar. 20, 2008

(86) PCT No.: PCT/US2008/003778
§ 371 (c)(1),
(2), (4) Date: Apr. 14, 2010

(87) PCT Pub. No.: WO2008/118377
PCT Pub. Date: Oct. 2, 2008

(65) Prior Publication Data
US 2011/0105376 A1    May 5, 2011

Related U.S. Application Data

(60) Provisional application No. 60/907,174, filed on Mar. 23, 2007.

(51) Int. Cl.
| | | |
|---|---|---|
| C12N 9/28 | (2006.01) | |
| C12P 19/14 | (2006.01) | |
| C12S 11/00 | (2006.01) | |
| C09B 67/00 | (2006.01) | |

(52) U.S. Cl.
USPC ............. 435/202; 435/99; 510/392; 510/393; 8/401

(58) Field of Classification Search
None
See application file for complete search history.

(56) References Cited

U.S. PATENT DOCUMENTS

| | | | |
|---|---|---|---|
| 5,316,691 A | | 5/1994 | Sone et al. |
| 5,429,766 A | | 7/1995 | Sone et al. |
| 5,736,499 A | * | 4/1998 | Mitchinson et al. .......... 510/392 |
| 5,824,532 A | | 10/1998 | Barnett et al. |
| 5,856,164 A | | 1/1999 | Outtrup et al. |
| 5,912,157 A | | 6/1999 | von der Osten et al. |
| 5,989,169 A | | 11/1999 | Svendsen et al. |
| 6,001,639 A | | 12/1999 | Schulein et al. |
| 6,022,724 A | | 2/2000 | Svendsen et al. |
| 6,093,562 A | | 7/2000 | Bisgård-Frantzen et al. |
| 6,117,664 A | | 9/2000 | Schulein et al. |
| 6,162,628 A | | 12/2000 | Cherry et al. |
| 6,197,565 B1 | | 3/2001 | Svendsen et al. |
| 6,218,164 B1 | | 4/2001 | Jones et al. |
| 6,297,038 B1 | | 10/2001 | Bisgård-Frantzen et al. |
| 6,338,959 B1 | | 1/2002 | Hatada et al. |
| 6,387,690 B1 | | 5/2002 | Schulein et al. |
| 6,403,355 B1 | | 6/2002 | Hagihara et al. |
| 6,432,689 B1 | | 8/2002 | Jones et al. |
| 6,440,716 B1 | | 8/2002 | Svendsen et al. |
| 6,482,622 B1 | | 11/2002 | Cherry et al. |
| 6,528,298 B1 | | 3/2003 | Svendsen et al. |
| 6,617,143 B1 | | 9/2003 | Fukuyama |
| 6,638,748 B2 | | 10/2003 | Hatada et al. |
| 6,855,531 B2 | | 2/2005 | Shulein et al. |
| 6,867,031 B2 | | 3/2005 | Bisgard-Frantzen et al. |
| 6,876,932 B1 | | 4/2005 | Cherry et al. |
| 6,887,986 B1 | | 5/2005 | Svendsen et al. |
| 6,916,645 B2 | | 7/2005 | Hagihara et al. |
| 6,939,703 B2 | | 9/2005 | Van Der Laan et al. |
| 6,979,731 B1 | | 12/2005 | Hatada et al. |
| 6,982,159 B2 | | 1/2006 | Dunn-Coleman et al. |
| 7,005,289 B2 | | 2/2006 | Dunn-Coleman et al. |
| 7,041,488 B2 | | 5/2006 | Outtrup et al. |
| 7,045,332 B2 | | 5/2006 | Dunn-Coleman et al. |
| 7,189,552 B2 | | 3/2007 | Lan et al. |
| 7,629,158 B2 | * | 12/2009 | Perez-Prat Vinuesa et al. ........ 435/201 |
| 8,153,412 B2 | * | 4/2012 | Chang et al. .................. 435/202 |
| 8,206,966 B2 | * | 6/2012 | Casc o-Pereira et al. ..... 435/201 |
| 8,236,545 B2 | * | 8/2012 | Cascao-Pereira et al. .... 435/202 |
| 2005/0176000 A1 | | 8/2005 | Callen et al. |
| 2005/0181493 A1 | | 8/2005 | Endo et al. |
| 2005/0214920 A1 | | 9/2005 | Harris et al. |
| 2005/0250663 A1 | | 11/2005 | Thisted et al. |
| 2005/0261156 A1 | | 11/2005 | Kottwitz et al. |
| 2005/0261158 A1 | | 11/2005 | Kottwitz et al. |
| 2006/0014265 A1 | | 1/2006 | Ferrari et al. |
| 2006/0019856 A1 | | 1/2006 | Kasturi et al. |

FOREIGN PATENT DOCUMENTS

| | | |
|---|---|---|
| EP | 0667910 B1 | 8/2003 |
| EP | 1 050 579 B1 | 4/2006 |
| EP | 1 199 356 B1 | 7/2009 |
| WO | WO 94/02597 A1 | 2/1994 |

(Continued)

OTHER PUBLICATIONS

Yamaguchi K et al. Random Point Mutation Analysis of the Signal Peptide Cleavage Area of *Bacillus stearothermophilus* alpha amylase. 1991. Agricultural Biological Chemistry. 55:11. 2875-2876.*
Genbank Accession No. AX428291, accessed at www.ncbi.nlm.nih.gov/nuccore/21538247?sat=13&satkey=12016854, 2 pp., Oct. 9, 2012.
Genbank Accession No. AAN18957, accessed at www.ncbi.nlm.nih.gov/protein/AAN18957 on Oct. 9, 2012, 1 pg.
Svendsen, et al., Database GenBank: CAC16483.1, "Bacillus licheniformis" (2000) http://www.ncbi.nlm.nih.gov/protein/CAC16483.1.
Database: UniProtKB/TrEMBL, Q208A7 (Q208A7_BACL1), (2006) http://www.uniprot.org/uniprot/Q208A7#section_features.

*Primary Examiner* — David J Steadman
*Assistant Examiner* — Paul Holland
(74) *Attorney, Agent, or Firm* — Dansico US Inc.

(57) ABSTRACT

A method of making a *Bacillus* alpha-amylase variant that increases alpha-amylase production and the alpha-amylases produced thereby. The recombinant alpha-amylases can be placed in compositions and used for purposes of laundry detergents, cleaning and dishwashing detergents, fabric desizing, starch liquefaction, cereal liquefaction, starch saccharification, biofilm removal, and starch hydrolysis in cane sugar processing.

15 Claims, 4 Drawing Sheets

(56) References Cited

FOREIGN PATENT DOCUMENTS

| | | |
|---|---|---|
| WO | WO 94/18314 A1 | 8/1994 |
| WO | WO 95/24471 A1 | 9/1995 |
| WO | WO 95/26397 A1 | 10/1995 |
| WO | WO 95/35382 A2 | 12/1995 |
| WO | WO 96/23873 A1 | 8/1996 |
| WO | WO 96/29397 A1 | 9/1996 |
| WO | WO 96/39528 * | 12/1996 |
| WO | WO 97/10342 A1 | 3/1997 |
| WO | WO 97/41213 A1 | 11/1997 |
| WO | WO 97/43424 A1 | 11/1997 |
| WO | WO 99/19467 A1 | 4/1999 |
| WO | WO 00/29560 A1 | 5/2000 |
| WO | 0060059 A2 | 10/2000 |
| WO | WO 01/29195 A1 | 4/2001 |
| WO | WO 02/10355 A2 | 2/2002 |
| WO | WO 02/10356 A2 | 2/2002 |
| WO | 2004042006 A2 | 5/2004 |
| WO | WO 2005/111203 A2 | 11/2005 |
| WO | WO 2006/002643 A2 | 1/2006 |

* cited by examiner

US 8,809,031 B2

SEQUENCE LISTING

<160> NUMBER OF SEQ ID NOS: 18

<210> SEQ ID NO 1
<211> LENGTH: 4
<212> TYPE: PRT
<213> ORGANISM: Artificial
<220> FEATURE:
<223> OTHER INFORMATION: synthetic alpha-amylase variant motif
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (2)..(2)
<223> OTHER INFORMATION: Xaa can be any naturally occurring amino acid
      except Ala or Val
<220> FEATURE:
<221> NAME/KEY: misc_feature
<222> LOCATION: (3)..(3)
<223> OTHER INFORMATION: Xaa can be Asp, Ala, His, or Gly
<220> FEATURE:
<221> NAME/KEY: misc_feature
<222> LOCATION: (4)..(4)
<223> OTHER INFORMATION: Xaa can be Leu, Gly, Pro, or Asp

<400> SEQUENCE: 1

Xaa Xaa Xaa Xaa
1

<210> SEQ ID NO 2
<211> LENGTH: 29
<212> TYPE: PRT
<213> ORGANISM: Bacillus licheniformis

<400> SEQUENCE: 2

Met Lys Gln Gln Lys Arg Leu Tyr Ala Arg Leu Leu Thr Leu Leu Phe
1               5                   10                  15

Ala Leu Ile Phe Leu Leu Pro His Ser Ala Ala Ser Ala
            20                  25

<210> SEQ ID NO 3
<211> LENGTH: 47
<212> TYPE: DNA
<213> ORGANISM: Artificial
<220> FEATURE:
<223> OTHER INFORMATION: synthetic primer

<400> SEQUENCE: 3
gaatgtctgc agcttcagca gcaaatctta atgggacgct gatgcag                47

<210> SEQ ID NO 4
<211> LENGTH: 46
<212> TYPE: DNA
<213> ORGANISM: Artificial
<220> FEATURE:
<223> OTHER INFORMATION: synthetic primer

<400> SEQUENCE: 4
cccggggtta actcatcttt gaacataaat tgaaaccgac ccgccg                 46

<210> SEQ ID NO 5
<211> LENGTH: 39
<212> TYPE: DNA
<213> ORGANISM: Artificial
<220> FEATURE:
<223> OTHER INFORMATION: synthetic primer

<400> SEQUENCE: 5

```
atcctactcg aggctttcct tttggaagaa aatataggg                                    39
```

<210> SEQ ID NO 6
<211> LENGTH: 35
<212> TYPE: DNA
<213> ORGANISM: Artificial
<220> FEATURE:
<223> OTHER INFORMATION: synthetic primer

<400> SEQUENCE: 6

```
tggaatctcg aggttttatc ctttaccttg tctcc                                        35
```

<210> SEQ ID NO 7
<211> LENGTH: 131
<212> TYPE: DNA
<213> ORGANISM: Artificial
<220> FEATURE:
<223> OTHER INFORMATION: synthetic primer

<400> SEQUENCE: 7

```
accccccctcg aggctttcct tttggaagaa aatataggga aatggtact tgttaaaaat             60
tcggaatatt tatacaatat catatgtttc acattgaaag gggaggagaa tcatgaaaca            120
acaaaaacgg c                                                                 131
```

<210> SEQ ID NO 8
<211> LENGTH: 107
<212> TYPE: DNA
<213> ORGANISM: Artificial
<220> FEATURE:
<223> OTHER INFORMATION: synthetic primer

<400> SEQUENCE: 8

```
gtcgacctcg aggttttatc ctttaccttg tctccaagct taaaataaaa aaacggattt             60
ccttcaggaa atccgtcctc tgttaactca tctttgaaca taaattg                          107
```

<210> SEQ ID NO 9
<211> LENGTH: 483
<212> TYPE: PRT
<213> ORGANISM: Bacillus licheniformis

<400> SEQUENCE: 9

Ala Asn Leu Asn Gly Thr Leu Met Gln Tyr Phe Glu Trp Tyr Met Pro
 1               5                  10                  15

Asn Asp Gly Gln His Trp Lys Arg Leu Gln Asn Asp Ser Ala Tyr Leu
                20                  25                  30

Ala Glu His Gly Ile Thr Ala Val Trp Ile Pro Pro Ala Tyr Lys Gly
            35                  40                  45

Thr Ser Gln Ala Asp Val Gly Tyr Gly Ala Tyr Asp Leu Tyr Asp Leu
        50                  55                  60

Gly Glu Phe His Gln Lys Gly Thr Val Arg Thr Lys Tyr Gly Thr Lys
 65                  70                  75                  80

Gly Glu Leu Gln Ser Ala Ile Lys Ser Leu His Ser Arg Asp Ile Asn
                85                  90                  95

Val Tyr Gly Asp Val Val Ile Asn His Lys Gly Ala Asp Ala Thr
                100                 105                 110

Glu Asp Val Thr Ala Val Glu Val Asp Pro Ala Asp Arg Asn Arg Val
            115                 120                 125

Ile Ser Gly Glu His Leu Ile Lys Ala Trp Thr His Phe His Phe Pro
        130                 135                 140

```
Gly Arg Gly Ser Thr Tyr Ser Asp Phe Lys Trp His Trp Tyr His Phe
145                 150                 155                 160

Asp Gly Thr Asp Trp Asp Glu Ser Arg Lys Leu Asn Arg Ile Tyr Lys
                165                 170                 175

Phe Gln Gly Lys Ala Trp Asp Trp Glu Val Ser Asn Glu Asn Gly Asn
            180                 185                 190

Tyr Asp Tyr Leu Met Tyr Ala Asp Ile Asp Tyr Asp His Pro Asp Val
        195                 200                 205

Ala Ala Glu Ile Lys Arg Trp Gly Thr Trp Tyr Ala Asn Glu Leu Gln
210                 215                 220

Leu Asp Gly Phe Arg Leu Asp Ala Val Lys His Ile Lys Phe Ser Phe
225                 230                 235                 240

Leu Arg Asp Trp Val Asn His Val Arg Glu Lys Thr Gly Lys Glu Met
                245                 250                 255

Phe Thr Val Ala Glu Tyr Trp Gln Asn Asp Leu Gly Ala Leu Glu Asn
            260                 265                 270

Tyr Leu Asn Lys Thr Asn Phe Asn His Ser Val Phe Asp Val Pro Leu
        275                 280                 285

His Tyr Gln Phe His Ala Ala Ser Thr Gln Gly Gly Gly Tyr Asp Met
290                 295                 300

Arg Lys Leu Leu Asn Gly Thr Val Val Ser Lys His Pro Leu Lys Ser
305                 310                 315                 320

Val Thr Phe Val Asp Asn His Asp Thr Gln Pro Gly Gln Ser Leu Glu
                325                 330                 335

Ser Thr Val Gln Thr Trp Phe Lys Pro Leu Ala Tyr Ala Phe Ile Leu
            340                 345                 350

Thr Arg Glu Ser Gly Tyr Pro Gln Val Phe Tyr Gly Asp Met Tyr Gly
        355                 360                 365

Thr Lys Gly Asp Ser Gln Arg Glu Ile Pro Ala Leu Lys His Lys Ile
370                 375                 380

Glu Pro Ile Leu Lys Ala Arg Lys Gln Tyr Ala Tyr Gly Ala Gln His
385                 390                 395                 400

Asp Tyr Phe Asp His His Asp Ile Val Gly Trp Thr Arg Glu Gly Asp
                405                 410                 415

Ser Ser Val Ala Asn Ser Gly Leu Ala Ala Leu Ile Thr Asp Gly Pro
            420                 425                 430

Gly Gly Ala Lys Arg Met Tyr Val Gly Arg Gln Asn Ala Gly Glu Thr
        435                 440                 445

Trp His Asp Ile Thr Gly Asn Arg Ser Glu Pro Val Val Ile Asn Ser
450                 455                 460

Glu Gly Trp Gly Glu Phe His Val Asn Gly Gly Ser Val Ser Ile Tyr
465                 470                 475                 480

Val Gln Arg

<210> SEQ ID NO 10
<211> LENGTH: 483
<212> TYPE: PRT
<213> ORGANISM: Artificial
<220> FEATURE:
<223> OTHER INFORMATION: synthetic variant

<400> SEQUENCE: 10

Ala Asn Leu Asn Gly Thr Leu Met Gln Tyr Phe Glu Trp Tyr Thr Pro
1               5                   10                  15
```

```
Asn Asp Gly Gln His Trp Lys Arg Leu Gln Asn Asp Ser Ala Tyr Leu
                20                  25                  30
Ala Glu His Gly Ile Thr Ala Val Trp Ile Pro Pro Ala Tyr Lys Gly
            35                  40                  45
Thr Ser Gln Ala Asp Val Gly Tyr Gly Ala Tyr Asp Leu Tyr Asp Leu
        50                  55                  60
Gly Glu Phe His Gln Lys Gly Thr Val Arg Thr Lys Tyr Gly Thr Lys
65                  70                  75                  80
Gly Glu Leu Gln Ser Ala Ile Lys Ser Leu His Ser Arg Asp Ile Asn
                85                  90                  95
Val Tyr Gly Asp Val Val Ile Asn His Lys Gly Gly Ala Asp Ala Thr
            100                 105                 110
Glu Asp Val Thr Ala Val Glu Val Asp Pro Ala Asp Arg Asn Arg Val
        115                 120                 125
Ile Ser Gly Glu Tyr Leu Ile Lys Ala Trp Thr His Phe His Phe Pro
130                 135                 140
Gly Arg Gly Ser Thr Tyr Ser Asp Phe Lys Trp His Trp Tyr His Phe
145                 150                 155                 160
Asp Gly Thr Asp Trp Asp Glu Ser Arg Lys Leu Asn Arg Ile Tyr Lys
                165                 170                 175
Phe Gln Gly Lys Ala Trp Asp Trp Glu Val Ser Ser Glu Asn Gly Asn
            180                 185                 190
Tyr Asp Tyr Leu Met Tyr Ala Asp Ile Asp Tyr Asp His Pro Asp Val
        195                 200                 205
Val Ala Glu Ile Lys Arg Trp Gly Thr Trp Tyr Ala Asn Glu Leu Gln
210                 215                 220
Leu Asp Gly Phe Arg Leu Asp Ala Val Lys His Ile Lys Phe Ser Phe
225                 230                 235                 240
Leu Arg Asp Trp Val Asn His Val Arg Glu Lys Thr Gly Lys Glu Met
                245                 250                 255
Phe Thr Val Ala Glu Tyr Trp Gln Asn Asp Leu Gly Ala Leu Glu Asn
            260                 265                 270
Tyr Leu Asn Lys Thr Asn Phe Asn His Ser Val Phe Asp Val Pro Leu
        275                 280                 285
His Tyr Gln Phe His Ala Ala Ser Thr Gln Gly Gly Gly Tyr Asp Met
290                 295                 300
Arg Lys Leu Leu Asn Gly Thr Val Val Ser Lys His Pro Leu Lys Ser
305                 310                 315                 320
Val Thr Phe Val Asp Asn His Asp Thr Gln Pro Gly Gln Ser Leu Glu
                325                 330                 335
Ser Thr Val Gln Thr Trp Phe Lys Pro Leu Ala Tyr Ala Phe Ile Leu
            340                 345                 350
Thr Arg Glu Ser Gly Tyr Pro Gln Val Phe Tyr Gly Asp Met Tyr Gly
        355                 360                 365
Thr Lys Gly Asp Ser Gln Arg Glu Ile Pro Ala Leu Lys His Lys Ile
370                 375                 380
Glu Pro Ile Leu Lys Ala Arg Lys Gln Tyr Ala Tyr Gly Ala Gln His
385                 390                 395                 400
Asp Tyr Phe Asp His His Asp Ile Val Gly Trp Thr Arg Glu Gly Asp
                405                 410                 415
Ser Ser Val Ala Asn Ser Gly Leu Ala Ala Leu Ile Thr Asp Gly Pro
            420                 425                 430
Gly Gly Ala Lys Arg Met Tyr Val Gly Arg Gln Asn Ala Gly Glu Thr
```

```
                    435                 440                 445
Trp His Asp Ile Thr Gly Asn Arg Ser Glu Pro Val Val Ile Asn Ser
    450                 455                 460

Glu Gly Trp Gly Glu Phe His Val Asn Gly Gly Ser Val Ser Ile Tyr
465                 470                 475                 480

Val Gln Arg

<210> SEQ ID NO 11
<211> LENGTH: 483
<212> TYPE: PRT
<213> ORGANISM: Artificial
<220> FEATURE:
<223> OTHER INFORMATION: synthetic variant

<400> SEQUENCE: 11

Ala Asn Leu Asn Gly Thr Leu Met Gln Tyr Phe Glu Trp Tyr Met Pro
1               5                   10                  15

Asn Asp Gly Gln His Trp Arg Arg Leu Gln Asn Asp Ser Ala Tyr Leu
            20                  25                  30

Ala Glu His Gly Ile Thr Ala Val Trp Ile Pro Pro Ala Tyr Lys Gly
        35                  40                  45

Thr Ser Gln Ala Asp Val Gly Tyr Gly Ala Tyr Asp Leu Tyr Asp Leu
    50                  55                  60

Gly Glu Phe His Gln Lys Gly Thr Val Arg Thr Lys Tyr Gly Thr Lys
65                  70                  75                  80

Gly Glu Leu Gln Ser Ala Ile Lys Ser Leu His Ser Arg Asp Ile Asn
                85                  90                  95

Val Tyr Gly Asp Val Val Ile Asn His Lys Gly Gly Ala Asp Ala Thr
            100                 105                 110

Glu Asp Val Thr Ala Val Glu Val Asp Pro Ala Asp Arg Asn Arg Val
        115                 120                 125

Ile Ser Gly Glu His Leu Ile Lys Ala Trp Thr His Phe His Phe Pro
    130                 135                 140

Gly Arg Gly Ser Thr Tyr Ser Asp Phe Lys Trp His Trp Tyr His Phe
145                 150                 155                 160

Asp Gly Thr Asp Trp Asp Glu Ser Arg Lys Leu Asn Arg Ile Tyr Lys
                165                 170                 175

Phe Gln Gly Lys Ala Trp Asp Trp Glu Val Ser Asn Glu Asn Gly Asn
            180                 185                 190

Tyr Asp Tyr Leu Met Tyr Ala Asp Ile Asp Tyr Asp His Pro Asp Val
        195                 200                 205

Ala Ala Glu Ile Lys Arg Trp Gly Thr Trp Tyr Ala Asn Glu Leu Gln
    210                 215                 220

Leu Asp Gly Phe Arg Leu Asp Ala Val Lys His Ile Lys Phe Ser Phe
225                 230                 235                 240

Leu Arg Asp Trp Val Asn His Val Arg Glu Lys Thr Gly Lys Glu Met
                245                 250                 255

Phe Thr Val Ala Glu Tyr Trp Gln Asn Asp Leu Gly Ala Leu Glu Asn
            260                 265                 270

Tyr Leu Asn Lys Thr Asn Phe Asn His Ser Val Phe Asp Val Pro Leu
        275                 280                 285

His Tyr Gln Phe His Ala Ala Ser Thr Gln Gly Gly Gly Tyr Asp Met
    290                 295                 300

Arg Lys Leu Leu Asn Gly Thr Val Val Ser Lys His Pro Leu Lys Ser
305                 310                 315                 320
```

Val Thr Phe Val Asp Asn His Asp Thr Gln Pro Gly Gln Ser Leu Glu
            325                 330                 335

Ser Thr Val Gln Thr Trp Phe Lys Pro Leu Ala Tyr Ala Phe Ile Leu
            340                 345                 350

Thr Arg Glu Ser Gly Tyr Pro Gln Val Phe Tyr Gly Asp Met Tyr Gly
            355                 360                 365

Thr Lys Gly Asp Ser Gln Arg Glu Ile Pro Ala Leu Lys His Lys Ile
            370                 375                 380

Glu Pro Ile Leu Lys Ala Arg Lys Gln Tyr Ala Tyr Gly Ala Gln His
385                 390                 395                 400

Asp Tyr Phe Asp His His Asp Ile Val Gly Trp Thr Arg Glu Gly Asp
                405                 410                 415

Ser Ser Val Ala Asn Ser Gly Leu Ala Ala Leu Ile Thr Asp Gly Pro
            420                 425                 430

Gly Gly Ala Lys Arg Met Tyr Val Gly Arg Gln Asn Ala Gly Glu Thr
            435                 440                 445

Trp His Asp Ile Thr Gly Asn Arg Ser Glu Pro Val Val Ile Asn Ser
            450                 455                 460

Glu Gly Trp Gly Glu Phe His Val Asn Gly Gly Ser Val Ser Ile Tyr
465                 470                 475                 480

Val Gln Arg

<210> SEQ ID NO 12
<211> LENGTH: 486
<212> TYPE: PRT
<213> ORGANISM: Artificial
<220> FEATURE:
<223> OTHER INFORMATION: synthetic variant

<400> SEQUENCE: 12

Ala Ala Pro Phe Asn Gly Thr Met Met Gln Tyr Phe Glu Trp Tyr Leu
1               5                   10                  15

Pro Asp Asp Gly Thr Leu Trp Thr Lys Val Ala Asn Glu Ala Asn Asn
            20                  25                  30

Leu Ser Ser Leu Gly Ile Thr Ala Leu Trp Leu Pro Pro Ala Tyr Lys
        35                  40                  45

Gly Thr Ser Arg Ser Asp Val Gly Tyr Gly Val Tyr Asp Leu Tyr Asp
    50                  55                  60

Leu Gly Glu Phe Asn Gln Lys Gly Thr Val Arg Thr Lys Tyr Gly Thr
65                  70                  75                  80

Lys Ala Gln Tyr Leu Gln Ala Ile Gln Ala Ala His Ala Ala Gly Met
                85                  90                  95

Gln Val Tyr Ala Asp Val Val Phe Asp His Lys Gly Gly Ala Asp Gly
            100                 105                 110

Thr Glu Trp Val Asp Ala Val Glu Val Asn Pro Ser Asp Arg Asn Gln
        115                 120                 125

Glu Ile Ser Gly Thr Tyr Gln Ile Gln Ala Trp Thr Lys Phe Asp Phe
    130                 135                 140

Pro Gly Arg Gly Asn Thr Tyr Ser Ser Phe Lys Trp Arg Trp Tyr His
145                 150                 155                 160

Phe Asp Gly Val Asp Trp Asp Glu Ser Arg Lys Leu Ser Arg Ile Tyr
                165                 170                 175

Lys Phe Arg Gly Lys Ala Trp Asp Trp Glu Val Asp Thr Glu Phe Gly
            180                 185                 190

```
Asn Tyr Asp Tyr Leu Met Tyr Ala Asp Leu Asp Met Asp His Pro Glu
            195                 200                 205

Val Val Thr Glu Leu Lys Asn Trp Gly Lys Trp Tyr Val Asn Thr Thr
    210                 215                 220

Asn Ile Asp Gly Phe Arg Leu Asp Ala Val Lys His Ile Lys Phe Ser
225                 230                 235                 240

Phe Phe Pro Asp Trp Leu Ser Tyr Val Arg Ser Gln Thr Gly Lys Pro
                245                 250                 255

Leu Phe Thr Val Gly Glu Tyr Trp Ser Tyr Asp Ile Asn Lys Leu His
                260                 265                 270

Asn Tyr Ile Thr Lys Thr Asn Gly Thr Met Ser Leu Phe Asp Ala Pro
            275                 280                 285

Leu His Asn Lys Phe Tyr Thr Ala Ser Lys Ser Gly Gly Ala Phe Asp
    290                 295                 300

Met Arg Thr Leu Met Thr Asn Thr Leu Met Lys Asp Gln Pro Thr Leu
305                 310                 315                 320

Ala Val Thr Phe Val Asp Asn His Asp Thr Glu Pro Gly Gln Ala Leu
                325                 330                 335

Gln Ser Trp Val Asp Pro Trp Phe Lys Pro Leu Ala Tyr Ala Phe Ile
                340                 345                 350

Leu Thr Arg Gln Glu Gly Tyr Pro Cys Val Phe Tyr Gly Asp Tyr Tyr
            355                 360                 365

Gly Ile Pro Gln Tyr Asn Ile Pro Ser Leu Lys Ser Lys Ile Asp Pro
    370                 375                 380

Leu Leu Ile Ala Arg Arg Asp Tyr Ala Tyr Gly Thr Gln His Asp Tyr
385                 390                 395                 400

Leu Asp His Ser Asp Ile Ile Gly Trp Thr Arg Glu Gly Gly Thr Glu
                405                 410                 415

Lys Pro Gly Ser Gly Leu Ala Ala Leu Ile Thr Asp Gly Pro Gly Gly
                420                 425                 430

Ser Lys Trp Met Tyr Val Gly Lys Gln His Ala Gly Lys Val Phe Tyr
            435                 440                 445

Asp Leu Thr Gly Asn Arg Ser Asp Thr Val Thr Ile Asn Ser Asp Gly
    450                 455                 460

Trp Gly Glu Phe Lys Val Asn Gly Gly Ser Val Ser Val Trp Val Pro
465                 470                 475                 480

Arg Lys Thr Thr Val Ser
                485

<210> SEQ ID NO 13
<211> LENGTH: 5
<212> TYPE: PRT
<213> ORGANISM: Artificial
<220> FEATURE:
<223> OTHER INFORMATION: synthetic alpha-amylase variant motif
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (2)..(2)
<223> OTHER INFORMATION: Xaa can be any naturally occurring amino acid
      except Ala or Val
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
```

```
<222> LOCATION: (4)..(4)
<223> OTHER INFORMATION: Xaa can be Asp, Ala, His, or Gly
<220> FEATURE:
<221> NAME/KEY: misc_feature
<222> LOCATION: (5)..(5)
<223> OTHER INFORMATION: Xaa can be Leu, Gly, Pro, or Asp

<400> SEQUENCE: 13

Xaa Xaa Xaa Xaa Xaa
1               5

<210> SEQ ID NO 14
<211> LENGTH: 6
<212> TYPE: PRT
<213> ORGANISM: Artificial
<220> FEATURE:
<223> OTHER INFORMATION: synthetic alpha-amylase variant motif
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(3)
<223> OTHER INFORMATION: Xaa can be any naturally occurring amino acid
      except Ala or Val
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be Asp, Ala, His, or Gly
<220> FEATURE:
<221> NAME/KEY: misc_feature
<222> LOCATION: (6)..(6)
<223> OTHER INFORMATION: Xaa can be Leu, Gly, Pro, or Asp

<400> SEQUENCE: 14

Xaa Ala Xaa Xaa Xaa Xaa
1               5

<210> SEQ ID NO 15
<211> LENGTH: 5
<212> TYPE: PRT
<213> ORGANISM: Artificial
<220> FEATURE:
<223> OTHER INFORMATION: synthetic alpha-amylase variant motif
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(3)
<223> OTHER INFORMATION: Xaa can be any naturally occurring amino acid
      except Ala or Val
<220> FEATURE:
<221> NAME/KEY: misc_feature
<222> LOCATION: (4)..(4)
<223> OTHER INFORMATION: Xaa can be Asp, Ala, His, or Gly
<220> FEATURE:
<221> NAME/KEY: misc_feature
<222> LOCATION: (5)..(5)
<223> OTHER INFORMATION: Xaa can be Leu, Gly, Pro, or Asp

<400> SEQUENCE: 15

Xaa Ala Xaa Xaa Xaa
1               5

<210> SEQ ID NO 16
<211> LENGTH: 6
```

```
<212> TYPE: PRT
<213> ORGANISM: Artificial
<220> FEATURE:
<223> OTHER INFORMATION: synthetic alpha-amylase variant motif
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (2)..(2)
<223> OTHER INFORMATION: Xaa can be Val, His, or Asp
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be Asp, Ala, His, or Gly
<220> FEATURE:
<221> NAME/KEY: misc_feature
<222> LOCATION: (6)..(6)
<223> OTHER INFORMATION: Xaa can be Leu, Gly, Pro, or Asp

<400> SEQUENCE: 16

Xaa Xaa Xaa Xaa Xaa Xaa
1               5

<210> SEQ ID NO 17
<211> LENGTH: 5
<212> TYPE: PRT
<213> ORGANISM: Artificial
<220> FEATURE:
<223> OTHER INFORMATION: synthetic alpha-amylase variant motif
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (2)..(2)
<223> OTHER INFORMATION: Xaa can be Val, His, or Asp
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be Asp, Ala, His, or Gly
<220> FEATURE:
<221> NAME/KEY: misc_feature
<222> LOCATION: (5)..(5)
<223> OTHER INFORMATION: Xaa can be Leu, Gly, Pro, or Asp

<400> SEQUENCE: 17

Xaa Xaa Xaa Xaa Xaa
1               5

<210> SEQ ID NO 18
<211> LENGTH: 4
<212> TYPE: PRT
<213> ORGANISM: Artificial
<220> FEATURE:
<223> OTHER INFORMATION: synthetic junction
<220> FEATURE:
<221> NAME/KEY: misc_feature
<222> LOCATION: (3)..(3)
<223> OTHER INFORMATION: Xaa can be Ala or Thr
```

```
<400> SEQUENCE: 18

Ala Ser Xaa Ala
1
```

ENHANCED AMYLASE PRODUCTION BY N-TERMINAL ADDITION TO MATURE AMYLASE PROTEIN

CROSS-REFERENCE TO RELATED APPLICATIONS

This application claims priority under 35 USC §371 to PCT/US2008/003778 (WO 2008/118377), with an international filing date of 20 Mar. 2008, which claims priority to U.S. 60/907,174, filed 23 Mar. 2007.

SEQUENCE LISTING

Incorporated herein by reference is a sequence listing comprising SEQ ID NOS: 1-12.

FIELD OF THE INVENTION

Disclosed are nucleic acids encoding polypeptides with amylase activity, wherein the polypeptide is modified from a *Bacillus* α-amylase, such as from a *Bacillus licheniformis* α-amylase.

BACKGROUND

Starch consists of a mixture of amylose (15-30% w/w) and amylopectin (70-85% w/w). Amylose consists of linear chains of α-1,4-linked glucose units having a molecular weight (MW) from about 60,000 to about 800,000. Amylopectin is a branched polymer containing α-1,6 branch points every 24-30 glucose units; its MW may be as high as 100 million.

Sugars from starch, in the form of concentrated dextrose syrups, are currently produced by an enzyme catalyzed process involving: (1) liquefaction (or viscosity reduction) of solid starch with an α-amylase into dextrins having an average degree of polymerization of about 7-10, and (2) saccharification of the resulting liquefied starch (i.e. starch hydrolysate) with amyloglucosidase (also called glucoamylase or GA). The resulting syrup has a high glucose content. Much of the glucose syrup that is commercially produced is subsequently enzymatically isomerized to a dextrose/fructose mixture known as isosyrup.

α-amylases (EC 3.2.1.1) hydrolyze starch, glycogen, and related polysaccharides by cleaving internal α-1,4-glucosidic bonds at random. This enzyme has a number of important commercial applications in, for example the sugar, brewing, alcohol, and textile industries. α-amylases are isolated from a wide variety of bacterial, fungal, plant and animal sources. The industrially many important α-amylases are those isolated from Bacilli.

For a number of years, α-amylase enzymes have been used for a variety of different purposes, including starch liquefaction, textile desizing, starch modification in the paper and pulp industry, and for brewing. These enzymes can also be used to remove starchy stains during dishwashing and laundry washing.

*Bacillus licheniformis* and other *Bacillus* species have a high capacity to secrete (heterologous) proteins (e.g., amylases, proteases, etc.) in to the growth medium. To direct these proteins outside the cell, they are synthesized as pre-proteins with an amino-terminal signal peptide. In general, signal peptides, which are usually 18 to 35 amino acids long, do not contain strict consensus sequences. However, the signal peptides do share tripartite structures formed by (1) a positively charged amino terminus (N-domain) and a more polar region, (2) followed by a hydrophobic core (H-domain), and (3) a more polar region, containing the signal peptide cleavage site (C-domain). The amino acids-3 and -1 (relative to the start of the mature protein) are usually residues with small neutral side chains (e.g., alanine, glycine and serine). In *B. subtilis*, the residue at position 1 of the mature chain is in most cases an alanine (Tjalsma, 1999, "Signal Peptidases of *Bacillus subtilis*: A Functional Analysis," Ph.D. thesis, University of Groningen, ISBN 90-367-1086-3). There are observations that indicate that processing of the pre-proteins, i.e. cleavage of the signal peptide, by signal peptidase is a secretion bottleneck for the production of some proteins (Bolhuis, 1999, "A Genetic Analysis of Determinants for Efficient Protein Secretion in *Bacillus subtilis*," Ph.D. thesis, University of Groningen, ISBN 90-367-1055-3).

Thus, there is a continued need for α-amylases, wherein greater amounts of α-amylase can be produced in an organism. Increased production will lead to, amongst other things, reduced costs, improved cost margins, plant capacity savings, and higher activity products.

SUMMARY

Accordingly, an aspect is directed to α-amylase variants that can be produced in an increased amount at less cost. These variants can be used in a variety of compositions and processes that use α-amylases.

One aspect contemplated is an isolated polypeptide comprising the motif depicted in SEQ ID NO: 1 or SEQ ID NO: 1 without a signal peptide, such as a mature α-amylase or variant. Thus, one aspect contemplates a SEQ ID NO: 1 that comprises SEQ ID NO: 2 (a signal peptide). Another aspect contemplates SEQ ID NO: 1 without a signal peptide, wherein said SEQ ID NO: 1 without a signal peptide comprises SEQ ID NOS: 9, 10, 11, or 12. Another aspect contemplates SEQ ID NO: 1 comprising SEQ ID NO: 13, 14, 15, 16, 17, or 18. Thus, the polypeptide sequences contemplated can be with the signal peptide, in the form of a pre-protein, or as a mature protein. The pre-protein can include signal peptides from the same species that produces the α-amylase, or can be a heterologous to the mature protein (i.e., wherein the signal peptide was derived from another microorganism than the mature protein).

Another embodiment contemplates a nucleic acid sequence that encodes any of the isolated polypeptide sequences discussed above.

Yet another aspect provides for a vector comprising any of the nucleic acid sequences encoding the polypeptide sequences.

A further aspect contemplates an isolated cell comprising either the nucleic acid sequence or a vector that comprises any of the aforementioned nucleic acid sequences. The isolated cell can be a microorganism. The microorganism can be a bacterium or a fungus. Exemplary bacteria include but are not limited to a Gram positive bacterium selected from the group consisting of *Bacillus subtilis, B. licheniformis, B. lentus, B. brevis, B. stearothermophilus, B. alkalophilus, B. amyloliquefaciens, B. coagulans, B. circulans, B. lautus, B. thuringiensis, Streptomyces lividans*, or *S. murinus*; or a Gram negative bacterium, wherein said Gram negative bacterium is *Escherichia coli*.

Also contemplated are uses for the above polypeptides in compositions for washing (in either manual or automatic formulations), dishwashing (in either manual or automatic formulations), textile desizing, hydrolyzing biofilms, saccharifying starch, liquefying starch, or processing starch from cane sugar.

A further aspect contemplates a detergent additive comprising any of the above polypeptides, wherein said detergent additive is optionally in the form of a non-dusting granulate, stabilized liquid, or protected enzyme. The additive can further comprise a cellulase, a protease, or an amylase, or a combination thereof. The amylase can be an α-amylase, a β-amylase, or a glucoamylase, or a combination thereof.

Yet a further aspect contemplates a detergent composition comprising any of the aforementioned polypeptides. Alternatively, the detergent composition can comprise the above-mentioned detergent additive. The detergent composition can further comprise an enzyme, where said enzyme is a protease, a lipase, a peroxidase, an amylase, a cellulase, a mannanase, a pectate lyase, or a combination of said enzymes.

Another aspect contemplates a manual or automatic dishwashing detergent composition comprising any of the above-mentioned polypeptides. The manual or automatic dishwashing detergent can further comprise an enzyme, where said enzyme is a protease, a lipase, a peroxidase, an amylase, a cellulase, a mannanase, a pectate lyase, or a combination of said enzymes.

In yet another embodiment, a manual or automatic laundry washing composition comprising any of the aforementioned polypeptides is contemplated. The manual or automatic laundry washing composition is further contemplated to comprise an enzyme, wherein said enzyme is a protease, a lipase, a peroxidase, an amylase, a cellulase, a mannanase, a pectate lyase, or a combination of enzymes.

Another embodiment contemplates a desizing composition comprising any of the above-mentioned polypeptides in an aqueous solution and optionally comprising an enzyme.

Another aspect contemplates a starch processing composition comprising any of the above-mentioned polypeptides in an aqueous solution. The starch processing composition can further comprise a glucoamylase, an isoamylase, a pullanase, or a combination thereof. The starch processing composition can be used in a method of processing a starch comprising administering the composition for a time sufficient to liquefy said starch, or saccharify said starch, or both liquefy and saccharify said starch.

Yet a further aspect provides for a biofilm hydrolyzing composition comprising any of the above mentioned polypeptides, wherein said composition is in a solution or gel, and optionally further comprises a cellulase, a hemicellulase, a xylanase, a lipase, a protease, a pectinase, an antimicrobial agent, or a combination thereof. Also contemplated is a method of hydrolyzing a biofilm comprising administering the composition for a period of time sufficient to partially or fully hydrolyze said biofilm.

BRIEF DESCRIPTION OF THE DRAWINGS

The accompanying drawings are incorporated in and constitute a part of this specification, illustrate embodiments. In the drawings.

DETAILED DESCRIPTION

Figure 1:
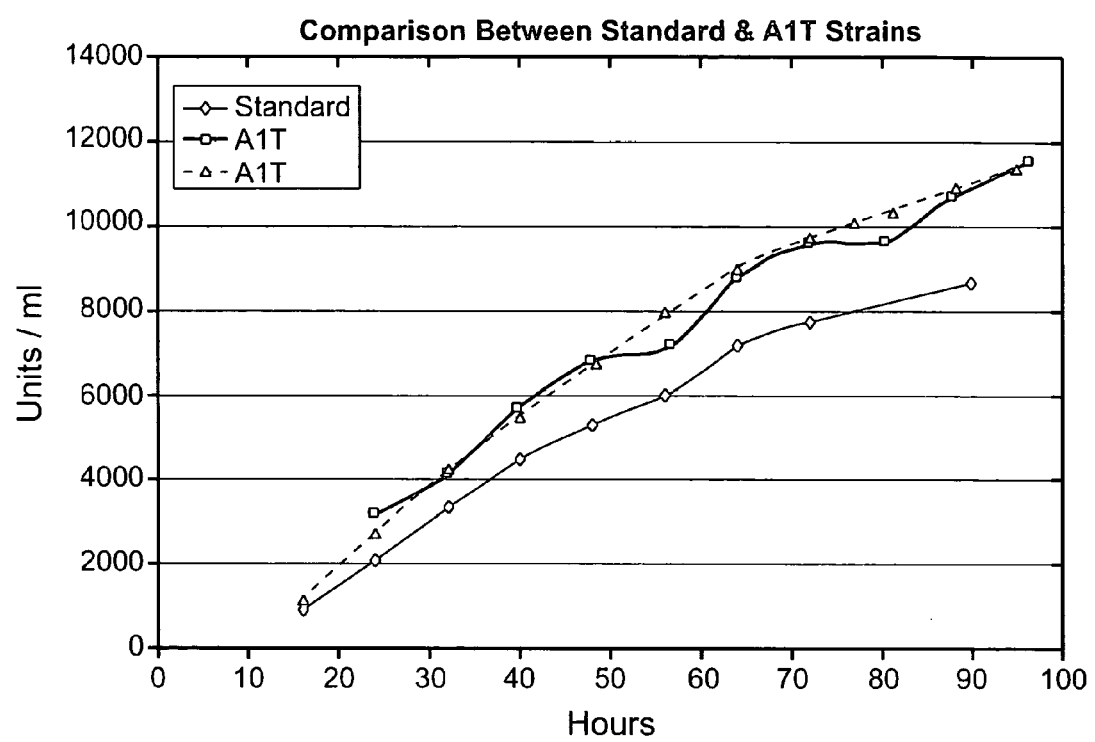
FIG. 1 is the comparison of production capacity between two batches of A1T and Spezyyme® FRED in *B. licheniformis*.

The application deals with a method of enhancing the amount of a *Bacillus* sp. α-amylase by modifying the polypeptide sequence of the mature α-amylase. Alternatively, the method can be used on any wild type or recombinant *Bacillus* sp. α-amylase. The following provides details on how this can be done, as well as compositions and uses for the α-amylase variants produced thereby.

1. Definitions & Abbreviations

In accordance with this detailed description, the following abbreviations and definitions apply. It must be noted that as used herein, the singular forms "a", "an", and "the" include plural referents unless the context clearly dictates otherwise. Thus, for example, reference to "an enzyme" includes a plurality of such enzymes and reference to "the formulation" includes reference to one or more formulations and equivalents thereof known to those skilled in the art, and so forth.

Unless defined otherwise, all technical and scientific terms used herein have the same meaning as commonly understood by one of ordinary skill in the art. The following terms are provided below.

1.1 Definitions

By "amylase" is meant to include any amylase such as glucoamylases, α-amylase, β-amylases and wild-type α-amylases of *Bacillus* sp., such as *B. licheniformis* and *B. subtilis*. Exemplary production strains are those used for KLM3' protein, amylase for grain processing (SGA), and an amylase for fabric and household cleaning. "Amylase" shall mean an enzyme that is, among other things, capable of catalyzing the degradation of starch. Amylases are hydrolases that cleave the α-D-(1→4) O-glycosidic linkages in starch. Generally, α-amylases (EC 3.2.1.1; α-D-(1→4)-glucan glucanohydrolase) are defined as endo-acting enzymes cleaving α-D-(1→4) O-glycosidic linkages within the starch molecule in a random fashion. In contrast, the exo-acting amylolytic enzymes, such as β-amylases (EC 3.2.1.2; α-D-(1→4)-glucan maltohydrolase) and some product-specific amylases like maltogenic α-amylase (EC 3.2.1.133) cleave the starch molecule from the non-reducing end of the substrate. β-Amylases, α-glucosidases (EC 3.2.1.20; α-D-glucoside glucohydrolase), glucoamylase (EC 3.2.1.3; α-D-(1→4)-glucan glucohydrolase), and product-specific amylases can produce malto-oligosaccharides of a specific length from starch.

By "α-amylase variant", "α-amylase variant polypeptide", and "variant enzyme" are meant an α-amylase protein that has been modified by substituting amino acid residues at the amino terminus of the mature α-amylase protein. As used herein, "parent enzymes," "parent sequence", "parent polypeptide", "wild-type α-amylase protein", and "parent polypeptides" shall mean enzymes and polypeptides from which the α-amylase variant polypeptides are derived. The parent enzyme may be a wild-type enzyme or an α-amylase that had previously been recombinantly engineered. The α-amylase variant can further include mutations in the signal sequence of the α-amylase parent polypeptide, or elsewhere in the α-amylase parent polypeptide. Thus, the α-amylase polypeptide can be a recombinantly engineered enzyme.

The α-amylase variant can also be a fusion protein, or "hybrid" or "chimeric protein," comprising a polypeptide sequence not endogenous to *B. licheniformis* or SEQ ID NO: 1 sequences. In one embodiment, the polypeptide sequence facilitates purification of the expressed protein. In another aspect, the heterologous sequence is an α-amylase polypeptide derived from a different genus or species than *B. licheniformis*. For example, the α-amylase variant can comprise a variant of a *B. licheniformis* α-amylase linked to the signal peptide of another *Bacillus* α-amylase, such as, but not limited to, *B. stearothermophilus*. Alternatively, the α-amylase protein can comprise the signal peptide of *B. licheniformis* (LAT) linked to the mature protein of another *Bacillus* α-amylase, wherein the fusion protein also has the enzyme-production enhanced mutation occurring at the $X_2$ residue of the mature protein. These can include substitutions with any amino acid other than an alanine or valine residue at $X_2$. The $X_2$ can further have additional amino acids in addition to the residue substituting for the alanine. The term "variant" may be used interchangeably with the term "mutant". Variants shall include polypeptides as well as nucleic acids. Variants shall include insertions; these variants can further contain additional substitutions, insertions, transversions, truncations, and/or inversions, at one or more locations. Variants can include sequences that are complementary to sequences that are capable of hybridizing to the nucleotide sequences presented herein. For example, a variant sequence is complementary to sequences capable of hybridizing under stringent conditions (e.g., 50° C. and 0.2×SSC {1×SSC=0.15 M NaCl, 0.015 M $Na_3$ citrate, pH 7.0}) to the nucleotide sequences presented herein. The term variant encompasses sequences that are complementary to sequences that are capable of hybridizing under high stringent conditions (e.g., 65° C. and 0.1×SSC {1×SSC=0.15 M NaCl, 0.015 M $Na_3$ citrate, pH 7.0}) to the nucleotide sequences presented herein. The variant may comprise 1, 2, 3, 4, 5, 10, 15, 20, 30, 40, 50, 60 or 70 amino acid substitutions, deletions or insertions, or any integer value in between, provided the variant retains α-amylase activity. The surface charge of the variant also may be altered by any number. For example, the number of positively charged amino acid residues on the enzyme surface may be reduced by 1, 2, 3, 4, 5, 6, 7 or 8. Such amino acid substitutions are expected to change the isoelectric point (pI) of the variant, among other things. Other characteristics of the variant may differ from the wild-type enzyme, as described herein.

By "isolated" is meant that the sequence is at least substantially free from at least one other component that the sequence is naturally associated and found in nature.

By "purified" is meant that the material is in a relatively pure state, e.g. at least about 90% pure, or at least about 95% pure, or at least about 98% pure.

By "thermostable" is meant the ability of the enzyme to retain activity after exposure to elevated temperatures. The thermostability of an enzyme, such as an α-amylase enzymes, is measured by its half-life. The half-life ($t_{1/2}$) is the time in minute, hours, or days during which half the enzyme activity is lost under defined conditions. The half-life value is calculated by measuring the residual amylase activity.

By "pH range" is meant the ability of the enzyme to exhibit catalytic activity from acidic to basic conditions spanning 5 or more pH units.

As used herein, "pH stable" relates to the ability of the enzyme to retain activity over a wide range of pHs.

As used herein, "food" shall include both prepared food, as well as an ingredient for a food, such as flour.

As used herein, "food ingredient" shall include a formulation, which is or can be added to functional foods or foodstuffs and includes formulations used at low levels in a wide variety of products that require, for example, acidifying or emulsifying. The food ingredient may be in the form of a solution or as a solid, depending on the use and/or the mode of application and/or the mode of administration.

As used herein, "functional food" means food capable of providing not only a nutritional effect and/or a taste satisfaction, but is also capable of delivering a further beneficial effect to consumer.

As used herein, "amino acid sequence" is synonymous with the term "polypeptide" and/or the term "protein". In some instances, the term "amino acid sequence" is synonymous with the term "peptide". In some instances, the term "amino acid sequence" is synonymous with the term "enzyme".

As used herein, "nucleotide sequence" or "nucleic acid sequence" refers to an oligonucleotide sequence or polynucleotide sequence, and variant, homologues, fragments and derivatives thereof (such as portions thereof). The nucleotide sequence may be of genomic or synthetic or recombinant origin, and may be double-stranded or single-stranded whether representing the sense or anti-sense strand. As used herein, the term nucleotide sequence includes genomic DNA, cDNA, synthetic DNA, and RNA. The DNA includes a cDNA sequence coding for an α-amylase variant polypeptide.

By "homologue" and "homology" shall mean an entity having a certain degree of identity with the subject amino acid sequences and the subject nucleotide sequences. A homologous sequence is taken to include an amino acid sequence at least 75%, 80%, 85% or 90% identical, at least 95%, 96%, 97%, 98% or 99% identical to the subject sequence. Typically, homologues will comprise the same active sites as the subject amino acid sequence.

As used herein, "hybridization" shall include the process by which a strand of nucleic acid joins with a complementary strand through base pairing, as well as the process of amplification as carried out in polymerase chain reaction (PCR) technologies. The α-amylase variant nucleic acid may exist as single- or double-stranded DNA or RNA, an RNA/DNA heteroduplex or an RNA/DNA copolymer.

As used herein, "copolymer" refers to a single nucleic acid strand that comprises both ribonucleotides and deoxyribonucleotides. The α-amylase variant nucleic acid may even be codon optimized to further increase expression.

As used herein, "synthetic" shall refer to that which is produced by in vitro chemical or enzymatic synthesis. It includes, but is not limited to, α-amylase variant nucleic acids made with optimal codon usage for host organisms, such as the methylotrophic yeasts *Pichia, Hansenula, Streptomyces, Trichoderma reesei*, or other expression hosts of choice, such as *Bacillus*.

As used herein, "transformed cell" shall include cells that have been transformed by use of recombinant DNA techniques. Transformation typically occurs by insertion of one or more nucleotide sequences into a cell. The inserted nucleotide sequence may be a heterologous nucleotide sequence (i.e. is a sequence that is not natural to the cell that is to be transformed, such as a sequence encoding a fusion protein).

As used herein, "operably linked" shall mean that the components described are in a relationship permitting them to function in their intended manner. A regulatory sequence operably linked to a coding sequence is ligated in such a way that expression of the coding sequence is achieved under condition compatible with the control sequences.

As used herein, "biologically active" shall refer to a sequence having a similar structural function (but not necessarily to the same degree), and/or similar regulatory function (but not necessarily to the same degree) and/or similar biochemical function (but not necessarily to the same degree) of the naturally occurring sequence.

1.2 Abbreviations

The following abbreviations apply unless indicated otherwise:
A1 T alanine to threonine substitution at position 1 ($X_2$) of a *Bacillus* α-amylase (or A 1→T)
AE alcohol ethoxylate
AEO alcohol ethoxylate
AEOS alcohol ethoxysulfate
AES alcohol ethoxysulfate
AFAU acid fungal α-amylase units
AGU glucoamylase activity unit
AOS α-olefinsulfonate
AS alcohol sulfate
BSA bovine serum albumin
cDNA complementary DNA
CMC carboxymethylcellulose
DNA deoxyribonucleic acid
DP3 degree of polymerization with three subunits
DPn degree of polymerization with n subunits
DS or ds dry solid
DTMPA diethyltriaminepentaacetic acid
EC enzyme commission for enzyme classification
EDTA ethylenediaminetetraacetic acid
EO ethylene oxide
F&HC fabric and household care
FAU fungal amylase unit
GA glucoamylase
HFCS high fructose corn syrup
HFSS high fructose starch based syrup
IPTG isopropyl β-D-thiogalactoside
LAS linear alkylbenzenesulfonate
LAT pertaining to *B. licheniformis* amylase
LU Liquiphon unit
MW molecular weight
NOBS nonanoyloxybenzenesulfonate
NTA nitrilotriacetic acid
OxAm Purastar® HPAM 5000 L
PCR polymerase chain reaction
PEG polyethyleneglycol
PVA poly(vinyl alcohol)
PVP poly(vinylpyrrolidone)
RNA ribonucleic acid
SAS secondary alkane sulfonates
TAED tetraacetylethylenediamine
TCA trichloroacetic acid
w/v weight/volume
w/w weight/weight
wt wild-type

2. α-Amylase Variants

The amylase variants can be created from any *Bacillus* amylase, including wild-type forms as well as engineered forms that have been engineered for enhanced specific activity, pH profile, thermostability, and temperature range profile, calcium ion requirements, and other enhanced characteristics. The variants described herein have enhanced production capability, wherein more protein can be secreted into the cell medium than the parent strain produced.

The motif of these variants is as follows:

$$NH_2-X_1-X_2-X_3-X_4-Y-COOH \quad \text{(SEQ ID NO: 1)}$$

wherein $X_1$ is the last amino acid in a signal peptide that ranges in size from 18-35 amino acids; wherein the signal peptide is tripartite in nature with a charged portion in the amino-terminus, an H-domain that is hydrophobic, and a carboxy domain that is charged; and wherein the $X_2$ domain can be derived from the same parent α-amylase or may be a heterologous or chimeric protein;

$X_1$ is the last amino acid in the signal sequence;

$X_2$ is A'-B', wherein when $X_2$ is alanine, A' is any amino acid other than alanine or valine, and B' is any amino acid residue or no amino acid residue; when $X_2$ is valine, histidine, or aspartic acid, A' is any amino acid and B' is any amino acid residue or no amino acid residue;

$X_3$ is asparagine, alanine, histidine, or glycine;

$X_4$ is leucine, glycine, proline or asparagine; and

Y is the remainder of the mature bacterial α-amylase or α-amylase variant. In one aspect, $X_2$ has A' as a threonine, and B' is no amino acid, or B' is any one or more amino acids up to 5 residues. The mature protein can be in the form initially of a fusion protein to a signal peptide derived from another *Bacillus* spp. or from the same species as the parental sequence. These can be wild-type *Bacillus* α-amylases or recombinant α-amylases, such as Teramyl-like α-amylases, as well as those described in U.S. Pat. Nos. 6,979,731; 6,338,959; 6,638,748; 6,440,716; 5,989,169; 6,022,724; 6,197,565; 6,887,986; 6,162,628; 6,482,622; 6,876,932; 6,093,562; 6,297,038; 6,867,031; 5,824,531; 5,856,164; 6,939,703; 6,218,164; 6,432,689; 5,316,691; 5,429,766; 6,197,565; 6,617,143; 6,916,645, 6,403,355; 6,982,159; 7,005,289; 7,041,488; 7,045,332; 6,001,639; 6,387,690; 6,855,531; 5,912,157; 6,117,664; and U.S. Publication Nos. 2005176000; 2005181493; 2005250663; 2005261156; 2005261158; 2006014265; 2006019856; 2006051849; 2005214920; and International PCT Application Nos. WO 06/002643; WO 94/02597; WO 94/18314; WO 96/23873; WO 97/43424; WO 97/41213; WO 99/19467; WO 95/26397; WO 99/19467; and European Patent Nos. 1050579; EP 1131418; EP 1226236; EP 1307547; EP 815209; EP 753057; EP 772684; EP 850307; and EP 749473. Also contemplated are nucleic acids which encode the various α-amylase variants, such as but not limited to *Bacillus* sp. A7-7 (DSM12368) α-amylase, Stainzyme® α-amylase, *Bacillus* sp. AA560 α-amylase (SEQ ID NO: 24 of U.S. Pat. No. 6,528,298), *B. halmapalus* α-amylase (SEQ ID NO: 2 U.S. Pat. No. 6,093, 562, Natalase®), *Bacillus* sp. no. 707 α-amylase, *Bacillus* sp. KSM-AP1378 α-amylase (GenBank Accession No. AX428291 and SEQ ID NO: 3 of EP 1199356), *Bacillus* sp. KSM-K38 α-amylase (SEQ ID NO: 4 of U.S. Pat. No. 6,403, 355), *Bacillus* sp. KSM-K36 α-amylase (SEQ ID NO: 2 of U.S. Pat. No. 6,403,355; GenBank Accession No. AAN18957), *B. clausii* KSM-K16 α-amylase, *B. halodurans* α-amylase, *B. clausii* BT-21 α-amylase (GenBank Accession No. AX037557), *B. amyloliquefaciens* α-amylase, SEQ ID NO: 2 of U.S. Pat. No. 5,856,164, OxAm® α-amylase, Duramyl®, and *B. stearothermophilus* α-amylase.

To secrete proteins in *B. licheniformis*, the signal peptide of *B. licheniformis* α-amylase (LAT) is frequently used. However, signal proteins from other *Bacillus* α-amylases can also be substituted. The amino acid sequence of the LAT signal peptide is:

MKQQKRLYARLLTLLFALIFLLPHSAASA.    (SEQ ID NO: 2)

One cleavage site of this signal peptide matches the general motif as described above: Ala-Ser-Ala/Ala (SEQ ID NO:18). It was observed that the production/secretion of Spezyme® FRED (a *B. licheniformis* α-amylase mutant) was increased by more than 20% by substitution of the alanine at position +1 ($X_2$) with threonine. Thus, part of the secretion bottleneck of proteins translocated by the LAT signal peptide is overcome by altering the cleavage site by replacing the last alanine in Ala-Ser-Ala/Ala (i.e., the $X_2$ site of SEQ ID NO:18) with threonine. Thus, one aspect provides for recombinant proteins where $X_2$ is any amino acid other than alanine or valine. For example, $X_2$ can be threonine. Another aspect contemplates having a substitution of two amino acids at position $X_2$, wherein $X_2$ is A-B, wherein A is any amino acid other than alanine or valine, and B is any amino acid including alanine. "B" can also be no residue and "A" is any amino acid other than alanine or valine. For example, the sequence at the junction of the signal peptide and the mature chain can be Ala-Ser-Ala/Ala (SEQ ID NO:18) where $X_2$ is replaced with Thr-Ala (i.e., the A-B introduced at $X_2$ is Thr-Ala). The cleavage site in this case is the same as that obtained by substituting alanine at +1 with threonine. The addition of a threonine residue (or another residue except Ala) to the N-terminal side of the mature chain of *Bacillus* α-amylase, such as Spezyme® FRED, or any other heterologous protein translocated by the LAT signal peptide is contemplated to result in increased production/secretion.

2.1 α-Amylase Variant Characterization

Enzyme variants can be characterized by nucleic acid and polypeptide sequences, by their secondary, tertiary, and/or quaternary structures, and/or by their specific activity. Additional features of the α-amylase variant include stability, calcium ion ($Ca^{+2}$) dependence, pH range, oxidation stability, and thermostability. The production enhanced α-amylase variants will have essentially the same characteristics as the parent protein, e.g., the same specific activity.

In one aspect, mutations (including amino acid substitutions and deletions in addition to the amino acids substituted or added to increase protein production) are of importance with respect to achieving altered stability, in particular improved stability (i.e., higher or lower), at especially high temperatures (i.e., 70-120° C.) and/or extreme pH (i.e. low or high pH, i.e., pH 4.0 to 6.0 or pH 8.0 to 11.0, respectively), and calcium concentrations below 60 ppm (i.e., unbound, therefore in solution).

Altered $Ca^{2+}$ stability means the stability of the enzyme under $Ca^{2+}$ depletion has been improved, i.e., higher or lower stability. Mutations (in addition to the Thr-Ala or the A-B introduced at $X_2$ position at the amino terminus of the mature protein) of importance are those which achieve altered $Ca^{2+}$ stability, in particular improved $Ca^{2+}$ stability, i.e., higher or lower stability, at especially high pH (i.e., pH 8.0-10.5). Thus, the mutants with the enhanced production capability can further include mutations that enhance calcium ion stability.

In a further aspect, important mutations (including amino acid substitutions and deletions) with respect to obtaining variants exhibiting altered specific activity, in particular increased or decreased specific activity in addition to enhanced production capacity, obtained by the $X_2$ mutation, especially at temperatures from 10-60° C., 20-50° C., and 30-40° C. for use in cleaning compositions. Specific activity temperature ranges for baking products may be higher.

α-amylase variants also may have altered oxidation stability, in particular higher oxidation stability, in comparison to the parent alpha-amylase. Increased oxidation stability is advantageous in, e.g., detergent compositions and decreased oxidation stability may be advantageous in composition for starch liquefaction.

The α-amylase variant can also have a mutation for thermostability. Such α-amylase variants can be used in baking or under other conditions that require elevated temperatures. For example, the α-amylase variant can degrade starch at temperatures of from about 55° C. to about 80° C. or more. The α-amylase variant can retain its activity after exposure to temperatures of up to about 95° C.

The α-amylase variant polypeptides described herein can also have mutations that extend half-life relative to the parent enzyme by for example 10%, 20%, 30%, 40%, 50%, 60%, 70%, 80%, 90%, 100%, 200% or more, and at elevated temperatures of from about 55° C. to about 95° C. or more, such as at about 80° C. or more. For example, the α-amylase variant can be heated for about 1-10 minutes at 80° C. or higher.

The α-amylase variant polypeptide has the same polypeptide stability as the parent sequence from which it derives. However, further mutations contemplated to enhance stability as well as to enhance production of the enzyme, can be combined with the those described herein for position $X_2$.

Thus, the nucleic acid encoding the α-amylase variant polypeptide also may comprise one or more mutations in addition to those set out above. Other mutations, such as deletions, insertions, substitutions, transversions, transitions and inversions, at one or more locations other than $X_2$, may also be included to have one or more of the above characteristics as needed. Likewise, the polypeptide encoded by the nucleic acid may be missing at least one of the substitutions set forth above.

The α-amylase variant polypeptide encoded by the nucleic acid can have the same pH stability as the parental sequence or different. For example, the variant can also have mutations that confer a greater pH stability range, or shifts the pH range to a desired range for the end commercial purpose of the enzyme. The variant is capable of degrading starch at a pH of from about 5.0 to about 10.5. The specific pH conditions may be any pH from pH 5.0 to pH 10.5. The α-amylase variant polypeptide encoded by the nucleic acid may have a longer half-life, or a higher activity (depending on the assay) when compared to the parent polypeptide under identical conditions or it may have the same activity as the parent polypeptide. The α-amylase variant polypeptide also may have about 10%, 20%, 30%, 40%, 50%, 60%, 70%, 80%, 90%, 100%, 200% or longer half life when compared to their parent polypeptide under identical pH conditions. Alternatively, or in addition, the enzyme variant may have higher activity when compared to the parent polypeptide under identical pH conditions.

In other embodiments, a nucleic acid complementary to a nucleic acid encoding any of the α-amylase variants set forth herein is provided. Additionally, a nucleic acid capable of hybridizing to the complement is provided. In another aspect, a nucleic acid encoding the functional equivalents capable of specifically hybridizing to any of the sequences set out above is provided herein, as well as its complement.

In a further embodiment, the sequence for use in the methods and compositions described here is a synthetic sequence.

It includes, but is not limited to, sequences made with optimal codon usage for expression in host organisms—such as the methylotrophic yeasts *Pichia* and *Hansenula*.

3. Production of α-Amylase Variants

A DNA sequence encoding the enzyme variant produced by methods described herein, or by any alternative methods known in the art, can be expressed, in enzyme form, using an expression vector which typically includes control sequences encoding a suitable promoter, operator, ribosome binding site, translation initiation signal, and, optionally, a repressor gene or various activator genes.

The recombinant expression vector carrying the DNA sequence encoding an α-amylase variant may be any vector that may conveniently be subjected to recombinant DNA procedures, and the choice of vector will often depend on the host cell into which it is to be introduced. Thus, the vector may be an autonomously replicating vector, i.e., a vector that exists as an extrachromosomal entity, the replication of which is independent of chromosomal replication, e.g., a plasmid, a bacteriophage or an extrachromosomal element, mini-chromosome or an artificial chromosome. Alternatively, the vector may be one which, when introduced into a host cell, is integrated into the host cell genome and replicated together with the chromosome(s) into which it has been integrated. The integrated gene may also be amplified to create multiple copies of the gene in the chromosome by use of an amplifiable construct driven by antibiotic selection or other selective pressure, such as an essential regulatory gene or by complementation through dose effect of an essential metabolic pathway gene.

In the vector, the DNA sequence should be operably connected to a suitable promoter sequence. The promoter may be any DNA sequence that shows transcriptional activity in the host cell of choice and may be derived from genes encoding proteins either homologous or heterologous to the host cell. Examples of suitable promoters for directing the transcription of the DNA sequence encoding an α-amylase variant, especially in a bacterial host, are the promoter of the lac operon of *E. coli*, the *Streptomyces coelicolor* agarase gene dagA or celA promoters, the promoters of the *Bacillus licheniformis* α-amylase gene (amyL), the promoters of the *Bacillus stearothermophilus* maltogenic amylase gene (amyM), the promoters of the *Bacillus amyloliquefaciens* α-amylase (amyQ), the promoters of the *Bacillus subtilis* xylA and xylB genes etc. For transcription in a fungal host, examples of useful promoters are those derived from the gene encoding *Aspergillus oryzae* TAKA amylase, *Rhizomucor miehei* aspartic proteinase, *Aspergillus niger* neutral α-amylase, *A. niger* acid stable α-amylase, *A. niger* glucoamylase, *Rhizomucor miehei* lipase, *A. oryzae* alkaline protease, *A. oryzae* triose phosphate isomerase, or *A. nidulans* acetamidase. When the gene encoding the α-amylase variant polypeptide is expressed in a bacterial species such as *E. coli*, a suitable promoter can be selected, for example, from a bacteriophage promoter including a T7 promoter and a phage lambda promoter. Examples of suitable promoters for the expression in a yeast species include but are not limited to the Gal 1 and Gal 10 promoters of *Saccharomyces cerevisiae* and the *Pichia pastoris* AOX1 or AOX2 promoters. For expression in *Trichoderma reesei*, the CBHII promoter also may be used. The expression vector may also comprise a suitable transcription terminator and, in eukaryotes, polyadenylation sequences operably connected to the DNA sequence encoding the α-amylase variant. Termination and polyadenylation sequences may be derived from the same sources as the promoter.

The vector may further comprise a DNA sequence enabling the vector to replicate in the host cell in question. Examples of such sequences are the origins of replication of plasmids pUC19, pACYC177, pUB110, pE194, pAMB1, pICatH, pHPLT (Genencor International, Inc.) and pIJ702.

The vector may also comprise a selectable marker, e.g. a gene the product of which complements a defect in the host cell, such as the dal genes from *B. subtilis* or *B. licheniformis*, or a gene which confers antibiotic resistance such as, e.g., ampicillin, kanamycin, chloramphenicol or tetracyclin resistance. Furthermore, the vector may comprise *Aspergillus* selection markers such as amdS, argB, niaD and xxsC, a marker giving rise to hygromycin resistance, or the selection may be accomplished by co-transformation, such as known in the art. See, e.g., International PCT Application WO 91/17243.

While intracellular expression or solid state fermentation may be advantageous in some respects, e.g. when using certain bacteria or fungi as host cells, generally, the expression of the variant is extracellular and into the culture medium. In general, the *Bacillus* α-amylases mentioned herein comprise a pre-protein format permitting secretion of the expressed protease into the culture medium. If desirable, this pre-protein peptide may be replaced by a different pre-peptide or signal sequence, conveniently accomplished by substitution of the DNA sequences encoding the respective pre-protein. The pre-proteins are typically characterized as having three domains, an N-terminal domain, an H-domain, and a C-terminal domain and range from 18 to 35 residues in length.

The expression vector typically includes the components of a cloning vector, such as, for example, an element that permits autonomous replication of the vector in the selected host organism and one or more phenotypically detectable markers for selection purposes. The expression vector normally comprises control nucleotide sequences encoding a promoter, operator, ribosome binding site, translation initiation signal and optionally, a repressor gene or one or more activator genes. Signal sequences are generally used to target the material to the cell culture media for easier enzyme collection, and optionally purification.

The procedures used to ligate the DNA construct encoding an α-amylase variant, the promoter, terminator and other elements, respectively, and to insert them into suitable vectors containing the information necessary for replication, are well known to persons skilled in the art (see e.g., Sambrook et al., MOLECULAR CLONING: A LABORATORY MANUAL, 2nd ed., Cold Spring Harbor, 1989 and $3^{rd}$ ed., 2001).

An isolated cell, either comprising a DNA construct or an expression vector, is advantageously used as a host cell in the recombinant production of an α-amylase variant. The cell may be transformed with the DNA construct encoding the variant, conveniently by integrating the DNA construct (in one or more copies) in the host chromosome. This integration is generally considered to be an advantage as the DNA sequence is more likely to be stably maintained in the cell. Integration of the DNA constructs into the host chromosome may be performed according to conventional methods, e.g., by homologous or heterologous recombination. Alternatively, the cell may be transformed with an expression vector as described above in connection with the different types of host cells.

Examples of suitable bacterial host organisms are Gram positive bacterial species such as Bacillaceae including *Bacillus subtilis, Bacillus licheniformis, Bacillus lentus, Bacillus brevis, Bacillus stearothermophilus, Bacillus alkalophilus, Bacillus amyloliquefaciens, Bacillus coagulans, Bacillus lautus, Bacillus megaterium,* and *Bacillus thuringiensis;*

*Streptomyces* species such as *Streptomyces murinus*; lactic acid bacterial species including *Lactococcus* spp. such as *Lactococcus lactis*; *Lactobacillus* spp. including *Lactobacillus reuteri*; *Leuconostoc* spp.; *Pediococcus* spp.; and *Streptococcus* spp. Alternatively, strains of a Gram negative bacterial species belonging to Enterobacteriaceae including *E. coli*, or to Pseudomonadaceae can be selected as the host organism. A suitable yeast host organism can be selected from the biotechnologically relevant yeasts species such as but not limited to yeast species such as *Pichia* sp., *Hansenula* sp., or *Kluyveromyces*, *Yarrowinia* species or a species of *Saccharomyces*, including *Saccharomyces cerevisiae* or a species belonging to *Schizosaccharomyces* such as, for example, *S. Pombe* species. A strain of the methylotrophic yeast species *Pichia pastoris* can be used as the host organism. Alternatively, the host organism can be a *Hansenula* species. Suitable host organisms among filamentous fungi include species of *Aspergillus*, e.g. *Aspergillus niger*, *Aspergillus oryzae*, *Aspergillus tubigensis*, *Aspergillus awamori*, or *Aspergillus nidulans*. Alternatively, strains of a *Fusarium* species, e.g. *Fusarium oxysporum* or of a *Rhizomucor* species such as *Rhizomucor miehei* can be used as the host organism. Other suitable strains include *Thermomyces* and *Mucor* species.

Yeast species contemplated include but are not limited to a species of *Saccharomyces* or *Schizosaccharomyces*, e.g. *Saccharomyces cerevisiae*. The filamentous fungus may advantageously belong to a species of *Aspergillus*, e.g. *Aspergillus oryzae* or *Aspergillus niger*. Fungal cells may be transformed by a process involving protoplast formation and transformation of the protoplasts followed by regeneration of the cell wall in a manner known per se. A suitable procedure for transformation of *Aspergillus* host cells includes for example those described in EP 238023.

In a yet further aspect, a method of producing an α-amylase variant is provided, which method comprises cultivating a host cell as described above under conditions conducive to the production of the variant and recovering the variant from the cells and/or culture medium.

The medium used to cultivate the cells may be any conventional medium suitable for growing the host cell in question and obtaining expression of the α-amylase variant. Suitable media and media components are available from commercial suppliers or may be prepared according to published recipes (e.g., as described in catalogues of the American Type Culture Collection). Exemplary culture media include but are not limited to those for fed-batch fermentations performed in a three thousand liter (3,000 L) stirred tank fermentor, which was used in the examples provided infra. The media used would be that most suitable for the host cell being used, for example the media discussed below for culturing *Bacillus licheniformis*. The growth medium in that case can consist of corn steep solids and soy flour as sources of organic compounds, along with inorganic salts as a source of sodium, potassium, phosphate, magnesium and sulfate, as well as trace elements. Typically, a carbohydrate source such as glucose is also part of the initial medium. Once the culture has established itself and begins growing, the carbohydrate is metered into the tank to maintain the culture as is known in the art. Samples are removed from the fermentor at regular intervals to measure enzyme titer using, for example, a colorimetric assay method. The fermentation process is halted when the enzyme production rate stops increasing according to the measurements.

An α-amylase variant secreted from the host cells may conveniently be recovered from the culture medium by well-known procedures, including separating the cells from the medium by centrifugation or filtration, and precipitating proteinaceous components of the medium by means of a salt such as ammonium sulfate, followed by the use of chromatographic procedures such as ion exchange chromatography, affinity chromatography, or the like.

Generally, a polynucleotide in a vector is operably linked to a control sequence that is capable of providing for the expression of the coding sequence by the host cell, i.e. the vector is an expression vector. The control sequences may be modified, for example by the addition of further transcriptional regulatory elements to make the level of transcription directed by the control sequences more responsive to transcriptional modulators. The control sequences may in particular comprise promoters.

Host cells may be cultured under suitable conditions which allow expression of the α-amylase variant proteins. Expression of the proteins may be constitutive such that they are continually produced, or inducible, requiring a stimulus to initiate expression. In the case of inducible expression, protein production can be initiated when required by, for example, addition of an inducer substance to the culture medium, for example dexamethasone, IPTG, or Sepharose. Polypeptides can also be produced recombinantly in an in vitro cell-free system, such as the TnT™ (Promega) rabbit reticulocyte system.

An α-amylase variant expressing host also can be cultured in the appropriate medium for the host, under aerobic conditions. Shaking or a combination of agitation and aeration can be provided, with production occurring at the appropriate temperature for that host, e.g., from about 30° C. to about 75° C., depending on the needs of the host and production of the desired α-amylase variant. Culturing can occur from about 12 to about 100 hours or greater (and any hour value there between) or for example, from 24 to 72 hours. Typically, the culture broth is at a pH of about 5.5 to about 8.0, again depending on the culture conditions needed for the host cell relative to production of the α-amylase variant.

4. Purification of α-Amylase Variants

Fermentation, separation, and concentration techniques are known in the art and conventional methods can be used in order to prepare the concentrated α-amylase variant containing solution.

After fermentation, a fermentation broth is obtained, the microbial cells and various suspended solids, including residual raw fermentation materials, are removed by conventional separation techniques in order to obtain an amylase solution. Filtration, centrifugation, microfiltration, rotary vacuum drum filtration, followed by ultra-filtration, extraction or chromatography, or the like are generally used.

It is desirable to concentrate the α-amylase variant containing solution in order to optimize recovery. Use of unconcentrated solutions requires increased incubation time in order to collect the purified α-amylase variant containing precipitate.

The α-amylase variant containing solution is concentrated into a concentrated solution using conventional concentration techniques until the desired enzyme level is obtained. Concentration of the enzyme variant containing solution may be achieved by any of the techniques discussed above. For example, ultrafiltration can be used.

The enzyme variant solution is concentrated into a concentrated enzyme variant solution until the enzyme variant activity of said concentrated α-amylase variant containing solution generally about 4 g/L or greater (e.g., 25 g/L or any amount between 4 and 25 g/L). The concentration is limited only by the amount of enzyme capable of being solubilized in solution.

By "precipitation agent" for purposes of purification is meant a compound effective to precipitate the α-amylase variant from the concentrated enzyme variant solution in solid form, whatever its nature may be, i.e. crystalline, amorphous or blend of both.

Precipitation can be performed using, for example, a metal halide precipitation agent. Metal halide precipitation agents include: alkali metal chlorides, alkali metal bromides and blends of two or more of these metal halides. The metal halide can be any of sodium chloride, potassium chloride, sodium bromide, potassium bromide and blends of two or more of these metal halides. For example, the metal halide is chosen from amongst sodium chloride and potassium chloride. In the case of sodium chloride, it can also serve as a preservative.

The metal halide precipitation agent is used in an amount effective to precipitate the α-amylase variant. The selection of at least an effective amount and an optimum amount of metal halide effective to cause precipitation of the enzyme variant, as well as the conditions of the precipitation for maximum recovery including incubation time, pH, temperature and concentration of α-amylase variant, will be readily apparent to one of ordinary skill in the art after routine testing.

Generally, at least about 5% w/v (weight/volume) to about 25% w/v of metal halide is added to the concentrated enzyme variant solution, and usually at least 8% w/v. Generally, no more than about 25% w/v of metal halide is added to the concentrated enzyme variant solution and usually no more than about 20% w/v. The optimal concentration of the metal halide precipitation agent will depend, among others, on the nature of the specific α-amylase variant and on its concentration in the concentrated α-amylase variant solution.

Another alternative to effect precipitation of the enzyme is to use of organic compounds, which can be added to the concentrated enzyme variant solution. The organic compound precipitating agent can include: 4-hydroxybenzoic acid, alkali metal salts of 4-hydroxybenzoic acid, alkyl esters of 4-hydroxybenzoic acid, and blends of two or more of these organic compounds. The addition of said organic compound precipitation agents can take place prior to, simultaneously with or subsequent to the addition of the metal halide precipitation agent, and the addition of both precipitation agents, organic compound and metal halide, may be carried out sequentially or simultaneously.

For further descriptions, see, e.g., U.S. Pat. No. 5,281,526. Generally, the organic compound precipitation agents are selected from the group consisting of alkali metal salts of 4-hydroxybenzoic acid, such as sodium or potassium salts, and linear or branched alkyl esters of 4-hydroxybenzoic acid, wherein the alkyl group contains from 1 to 12 carbon atoms, and blends of two or more of these organic compounds. The organic compound precipitations agents can be for example linear or branched alkyl esters of 4-hydroxybenzoic acid, wherein the alkyl group contains from 1 to 10 carbon atoms, and blends of two or more of these organic compounds. For example, the organic compounds can be linear alkyl esters of 4-hydroxybenzoic acid, wherein the alkyl group contains from 1 to 6 carbon atoms, and blends of two or more of these organic compounds. Methyl esters of 4-hydroxybenzoic acid, propyl ester of 4-hydroxybenzoic acid, butyl ester of 4-hydroxybenzoic acid, ethyl ester of 4-hydroxybenzoic acid and blends of two or more of these organic compounds can also be used. Additional organic compounds also include but are not limited to 4-hydroxybenzoic acid methyl ester (named methyl PARABEN), 4-hydroxybenzoic acid propyl ester (named propyl PARABEN), which also are amylase preservative agents.

Addition of the said organic compound precipitation agent provides the advantage of high flexibility of the precipitation conditions with respect to pH, temperature, α-amylase variant concentration, precipitation agent concentration, and time of incubation.

The organic compound precipitation agent is used in an amount effective to improve precipitation of the enzyme variant by means of the metal halide precipitation agent. The selection of at least an effective amount and an optimum amount of organic compound precipitation agent, as well as the conditions of the precipitation for maximum recovery including incubation time, pH, temperature and concentration of enzyme variant, will be readily apparent to one of ordinary skill in the art, in light of the present disclosure, after routine testing.

Generally, at least 0.01% w/v of organic compound precipitation agent is added to the concentrated enzyme variant solution and usually at least 0.02% w/v. Generally, no more than 0.3% w/v of organic compound precipitation agent is added to the concentrated enzyme variant solution and usually no more than 0.2% w/v.

The concentrated enzyme variant solution, containing the metal halide precipitation agent and, for example, the organic compound precipitation agent, is adjusted to a pH which will, of necessity, depend on the enzyme variant to be purified. Generally, the pH is adjusted at a level near the isoelectric point of the amylase. Generally, the pH is adjusted at a pH in a range from about 2.5 pH units below the isoelectric point (pI) up to about 2.5 pH units above the isoelectric point. For purposes of illustration, when the enzyme variant is an α-amylase variant derived from *Bacillus licheniformis*, the concentrated enzyme variant solution is usually adjusted to a pH of between about 5.5 and 9.7 or to a pH of between about 6.5 and 9.0. pH changes for other *Bacillus* α-amylases variants can similarly be prepared.

The incubation time necessary to obtain a purified enzyme variant precipitate depends on the nature of the specific enzyme variant, the concentration of enzyme, and the specific precipitation agent(s) and its (their) concentration. Generally, the time effective to precipitate the enzyme variant is between about 1 to about 30 hours; usually it does not exceed about 25 hours. In the presence of the organic compound precipitation agent, the time of incubation can still be reduced to less than about 10 hours, and in most cases even about 6 hours.

Generally, the temperature during incubation is between about 4° C. and about 50° C. Usually, the method is carried out at a temperature between about 10° C. and about 45° C., or between about 20° C. and about 40° C. The optimal temperature for inducing precipitation varies according to the solution conditions and the enzyme variant or precipitation agent(s) used.

The overall recovery of purified enzyme variant precipitate, and the efficiency with which the process is conducted, is improved by agitating the solution comprising the enzyme variant, the added metal halide and the added organic compound. The agitation step is done both during addition of the metal halide and the organic compound, and during the subsequent incubation period. Suitable agitation methods include mechanical stirring or shaking, vigorous aeration, or any similar technique.

After the incubation period, the purified enzyme variant is then separated from the dissociated pigment and other impurities and collected by conventional separation techniques, such as filtration, centrifugation, microfiltration, rotary vacuum filtration, ultrafiltration, press filtration, cross membrane microfiltration, cross flow membrane microfiltration or the like. Cross membrane microfiltration can be one method used. Further purification of the purified enzyme variant precipitate can be obtained by washing the precipitate with water. For example, the purified enzyme variant precipitate is washed with water containing the metal halide precipitation agent, or for example with water containing the metal halide and the organic compound precipitation agents.

During the culturing, thermostable amylase extracellularly accumulates in the culture broth. For the isolation and purification of the desired α-amylase variant, the culture broth is centrifuged or filtered to eliminate cells, and the resulting cell-free liquid is used for the purification of the enzyme. In one embodiment, the cell-free broth is subjected to salting out using ammonium sulfate at about 70% saturation; the 70% saturation-precipitation fraction is then dissolved in a buffer and applied to a column such as a Sephadex G-100 column, and eluted to recover the enzyme variant active fraction. For further purification, a conventional procedure such as ion exchange chromatography may be used.

Purified enzyme variants are useful for all applications in which the enzyme variants are generally utilized. For example, they can be used in laundry detergents and spot removers, in the food industry, in starch processing and baking, and in pharmaceutical compositions as digestive aids. They can be made into a final product that is either liquid (solution, slurry) or solid (granular, powder).

Alternatively, the enzyme product can be recovered and a floccing agent is added to the media in order to remove cells and cell debris by filtration or centrifugation without further purification of the enzyme.

5. Compositions Comprising α-Amylase Variants

The α-amylase variants possess valuable properties allowing for a variety of industrial applications. An enzyme variant can be used as a component in washing, dishwashing and hard-surface cleaning detergent compositions. Numerous variants are particularly useful in the production of sweeteners and ethanol from starch, and/or for textile desizing. Conditions for conventional starch-conversion processes, including starch liquefaction and/or saccharification processes are described in, for example, U.S. Pat. No. 3,912,590 and in EP patent publications Nos. 252,730 and 63,909.

In the pharmaceutical applications α-amylase variants are usually dried, such as by lyophilization.

5.1 Cleaning and Dishwashing Compositions and Use

The α-amylase variants discussed herein can be formulated in detergent compositions for use in cleaning dishes or other cleaning compositions. These can be powders or liquids. The compositions can comprise the α-amylase variant alone, other amylolytic enzymes, other cleaning enzymes, and other components common to cleaning compositions.

Thus, a dishwashing detergent composition can comprise a surfactant. The surfactant may be anionic, non-ionic, cationic, amphoteric or a mixture of these types. The detergent can contain 0% to about 90% by weight of a non-ionic surfactant, such as low- to non-foaming ethoxylated propoxylated straight-chain alcohols.

In the detergent applications, α-amylase variants are usually used in a liquid composition containing propylene glycol. The α-amylase variant is solubilized in for example in propylene glycol by circulating in a 25% volume/volume propylene glycol solution containing 10% calcium chloride.

The detergent composition may contain detergent builder salts of inorganic and/or organic types. The detergent builders may be subdivided into phosphorus-containing and non-phosphorus-containing types. The detergent composition usually contains about 1% to about 90% of detergent builders. Examples of phosphorus-containing inorganic alkaline detergent builders, when present, include the water-soluble salts, especially alkali metal pyrophosphates, orthophosphates, and polyphosphates. An example of phosphorus-containing organic alkaline detergent builder, when present, includes the water-soluble salts of phosphonates. Examples of non-phosphorus-containing inorganic builders, when present, include water-soluble alkali metal carbonates, borates, and silicates, as well as the various types of water-insoluble crystalline or amorphous alumino silicates, of which zeolites are the best-known representatives.

Examples of suitable organic builders include the alkali metal; ammonium and substituted ammonium; citrates; succinates; malonates; fatty acid sulfonates; carboxymethoxy succinates; ammonium polyacetates; carboxylates; polycarboxylates; aminopolycarboxylates; polyacetyl carboxylates; and polyhydroxsulfonates.

Other suitable organic builders include the higher molecular weight polymers and copolymers known to have builder properties, for example appropriate polyacrylic acid, polymaleic and polyacrylic/polymaleic acid copolymers, and their salts.

The cleaning composition may contain bleaching agents of the chlorine/bromine-type or the oxygen-type. Examples of inorganic chlorine/bromine-type bleaches are lithium, sodium or calcium hypochlorite, and hypobromite, as well as chlorinated trisodium phosphate. Examples of organic chlorine/bromine-type bleaches are heterocyclic N-bromo- and N-chloro-imides such as trichloroisocyanuric, tribromoisocyanuric, dibromoisocyanuric, and dichloroisocyanuric acids, and salts thereof with water-solubilizing cations such as potassium and sodium. Hydantoin compounds are also suitable.

The cleaning composition may contain oxygen bleaches, for example in the form of an inorganic persalt, with for example a bleach precursor or as a peroxy acid compound. Typical examples of suitable peroxy bleach compounds are alkali metal perborates, both tetrahydrates and monohydrates, alkali metal percarbonates, persilicates, and perphosphates. Exemplary activator materials are TAED, and glycerol triacetate. Enzymatic bleach activation systems may also be present, e.g., such as perborate or percarbonate, glycerol triacetate and perhydrolase, e.g., as disclosed in International PCT Application WO 2005/056783.

The cleaning composition may be stabilized using conventional stabilizing agents for the enzyme(s), e.g. a polyol such as, e.g., propylene glycol, a sugar or a sugar alcohol, lactic acid, boric acid, or a boric acid derivative (e.g. an aromatic borate ester).

The cleaning composition may also contain other conventional detergent ingredients, e.g. deflocculant material, filler material, foam depressors, anti-corrosion agents, soil-suspending agents, sequestering agents, anti-soil redeposition agents, dehydrating agents, dyes, bactericides, fluorescers, thickeners, and perfumes.

Finally, the α-amylase variants may be used in conventional dishwashing detergents, e.g. in any of the detergents described in any of the following patent publications with the consideration that the α-amylase modified is a *Bacillus* α-amylase modified at $X_2$ of SEQ ID NO: 1 for enhanced production or is an α-amylase in the listed patents and patent application used in addition to the α-amylase variants disclosed herein: CA 2006687, GB 2200132, GB 2234980, GB 2228945, DE 3741617, DE 3727911, DE 4212166, DE 4137470, DE 3833047, DE 4205071, WO 93/25651, WO 93/18129, WO 93/04153, WO 92/06157, WO 92/08777, WO 93/21299, WO 93/17089, WO 93/03129, EP 481547, EP 530870, EP 533239, EP 554943, EP 429124, EP 346137, EP 561452, EP 318204, EP 318279, EP 271155, EP 271156, EP 346136, EP 518719, EP 518720, EP 518721, EP 516553, EP 561446, EP 516554, EP 516555, EP 530635, EP 414197, U.S. Pat. No. 5,112,518, U.S. Pat. No. 5,141,664, and U.S. Pat. No. 5,240,632.

5.2 Laundry Detergent Compositions and Use

According to the embodiment, one or more α-amylase variants may typically be a component of a detergent composition. As such, it may be included in the detergent composition in the form of a non-dusting granulate, a stabilized liquid, or a protected enzyme. Non-dusting granulates may be produced, e.g. as disclosed in U.S. Pat. Nos. 4,106,991 and 4,661,452 (both to Novo Industri A/S) and may optionally be coated by methods known in the art. Examples of waxy coating materials are poly(ethylene oxide) products (polyethyleneglycol, PEG) with mean molar weights of 1,000 to 20,000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in, for example, GB Patent No. 1483591. Liquid enzyme preparations may, for instance, be stabilized by adding a polyol such as propylene glycol, a sugar or sugar alcohol, lactic acid or boric acid according to established methods. Other enzyme stabilizers are well known in the art. Protected enzymes may be prepared according to the method disclosed in for example EP 238,216. Polyols have long been recognized as stabilizers of proteins as well as for improving the solubility of proteins, see e.g., J. K. Kaushik et al., "Why is trehalose an exceptional protein stabilizer? An analysis of the thermal stability of proteins in the presence of the compatible osmolyte trehalose" *J. Biol. Chem.* 278: 26458-65 (2003) and references cited therein; and M. Conti et al., "Capillary isoelectric focusing: the problem of protein solubility," *J. Chromatography* 757: 237-245 (1997).

The detergent composition may be in any convenient form, e.g. as powders, granules, pastes, or liquids. A liquid detergent may be aqueous, typically containing up to about 70% of water, and 0% to about 30% of organic solvent, it may also be in the form of a compact gel type containing only about 30% water.

The detergent composition comprises one or more surfactants, each of which may be anionic, nonionic, cationic, or zwitterionic. The detergent will usually contain 0% to about 50% of anionic surfactant, such as linear alkylbenzenesulfonate (LAS); α-olefinsulfonate (AOS); alkyl sulfate (fatty alcohol sulfate) (AS); alcohol ethoxysulfate (AEOS or AES); secondary alkanesulfonates (SAS); α-sulfo fatty acid methyl esters; alkyl- or alkenylsuccinic acid; or soap. The composition may also contain 0% to about 40% of nonionic surfactant such as alcohol ethoxylate (AEO or AE), carboxylated alcohol ethoxylates, nonylphenol ethoxylate, alkylpolyglycoside, alkyldimethylamineoxide, ethoxylated fatty acid monoethanolamide, fatty acid monoethanolamide, or polyhydroxy alkyl fatty acid amide (as described for example in WO 92/06154).

The detergent composition may additionally comprise one or more other enzymes, such as lipase, cutinase, protease, cellulase, peroxidase, and/or laccase in any combination.

The detergent may contain about 1% to about 65% of a detergent builder or complexing agent such as zeolite, diphosphate, triphosphate, phosphonate, citrate, nitrilotriacetic acid (NTA), ethylenediaminetetraacetic acid (EDTA), diethylenetriaminepentaacetic acid (DTMPA), alkyl- or alkenylsuccinic acid, soluble silicates or layered silicates (e.g. SKS-6 from Hoechst). The detergent may also be unbuilt, i.e. essentially free of detergent builder. Enzymes may be used in any composition compatible with the stability of the enzyme. Enzymes can be protected against generally deleterious components by known forms of encapsulation, as for example, by granulation or sequestration in hydro gels. Enzymes and specifically α-amylases either with or without the starch binding domains are not limited to laundry and dishwashing applications, but may bind use in surface cleaners and ethanol production from starch or biomass.

The detergent may comprise one or more polymers. Examples include carboxymethylcellulose (CMC), poly(vinylpyrrolidone) (PVP), polyethyleneglycol (PEG), poly(vinyl alcohol) (PVA), polycarboxylates such as polyacrylates, maleic/acrylic acid copolymers and lauryl methacrylate/acrylic acid copolymers.

The detergent may contain a bleaching system, which may comprise a $H_2O_2$ source such as perborate or percarbonate, which may be combined with a peracid-forming bleach activator such as tetraacetylethylenediamine (TAED) or nonanoyloxybenzenesulfonate (NOBS). Alternatively, the bleaching system may comprise peroxy acids of e.g. the amide, imide, or sulfone type. The bleaching system can also be an enzymatic bleaching system where a perhydrolase activates peroxide, such as that described in International PCT Application WO 2005/056783.

The enzymes of the detergent composition may be stabilized using conventional stabilizing agents, e.g. a polyol such as propylene glycol or glycerol; a sugar or sugar alcohol; lactic acid; boric acid or a boric acid derivative such as e.g. an aromatic borate ester; and the composition may be formulated as described in, e.g., WO 92/19709 and WO 92/19708.

The detergent may also contain other conventional detergent ingredients such as fabric conditioners including clays, foam boosters, suds suppressors, anti-corrosion agents, soil-suspending agents, anti-soil redeposition agents, dyes, bactericides, optical brighteners, or perfume, for example. The pH (measured in aqueous solution at use concentration) is usually neutral or alkaline, e.g., pH about 7.0 to about 11.0.

The α-amylase variant may be incorporated in concentrations conventionally employed in detergents. It is at present contemplated that, in the detergent composition, the α-amylase variant may be added in an amount corresponding to 0.00001-1.0 mg (calculated as pure enzyme protein) of α-amylase variant per liter of wash liquor. Particular forms of detergent compositions comprising the α-amylase variants can be formulated to include:

1) A detergent composition formulated as a granulate having a bulk density of at least 600 g/L comprising linear alkylbenzenesulfonate (calculated as acid) about 7% to about 12%; alcohol ethoxysulfate (e.g., $C_{12-18}$ alcohol, 1-2 ethylene oxide (EO)) or alkyl sulfate (e.g., $C_{16-18}$) about 1% to about 4%; alcohol ethoxylate (e.g., $C_{14-15}$ alcohol, 7 EO) about 5%

1) to about 9%; sodium carbonate (e.g., $Na_2CO_3$) about 14% to about 20%; soluble silicate (e.g., $Na_2O, 2SiO_2$) about 2 to about 6%; zeolite (e.g., $NaAlSiO_4$) about 15% to about 22%; sodium sulfate (e.g., $Na_2SO_4$) 0% to about 6%; sodium citrate/citric acid (e.g., $C_6H_5Na_3O_7/C_6H_8O_7$) about 0% to about 15%; sodium perborate (e.g., $NaBO_3H_2O$) about 11% to about 18%; TAED about 2% to about 6%; carboxymethylcellulose (CMC) and 0% to about 2%; polymers (e.g., maleic/acrylic acid, copolymer, PVP, PEG) 0-3%; enzymes (calculated as pure enzyme) 0.0001-0.1% protein; and minor ingredients (e.g., suds suppressors, perfumes, optical brightener, photobleach) 0-5%.

2) A detergent composition formulated as a granulate having a bulk density of at least 600 g/L comprising linear alkylbenzenesulfonate (calculated as acid) about 6% to about 11%; alcohol ethoxysulfate (e.g., $C_{12-18}$ alcohol, 1-2 EO) or alkyl sulfate (e.g., $C_{16-18}$) about 1% to about 3%; alcohol ethoxylate (e.g., $C_{14-15}$ alcohol, 7 EO) about 5% to about 9%; sodium carbonate (e.g., $Na_2CO_3$) about 15% to about 21%; soluble silicate (e.g., $Na_2O, 2SiO_2$) about 1% to about 4%; zeolite (e.g., $NaAlSiO_4$) about 24% to about 34%; sodium sulfate (e.g., $Na_2SO_4$) about 4% to about 10%; sodium citrate/citric acid (e.g., $C_6H_5Na_3O_7/C_6H_8O_7$) 0% to about 15%; carboxymethylcellulose (CMC) 0% to about 2%; polymers (e.g., maleic/acrylic acid copolymer, PVP, PEG) 1-6%; enzymes (calculated as pure enzyme protein) 0.0001-0.1%; minor ingredients (e.g., suds suppressors, perfume) 0-5%.

3) A detergent composition formulated as a granulate having a bulk density of at least 600 g/L comprising linear alkylbenzenesulfonate (calculated as acid) about 5% to about 9%; alcohol ethoxylate (e.g., $C_{12-15}$ alcohol, 7 EO) about 7% to about 14%; Soap as fatty acid (e.g., $C_{16-22}$ fatty acid) about 1 to about 3%; sodium carbonate (as $Na_2CO_3$) about 10% to about 17%; soluble silicate (e.g., $Na_2O, 2SiO_2$) about 3% to about 9%; zeolite (as $NaAlSiO_4$) about 23% to about 33%; sodium sulfate (e.g., $Na_2SO_4$) 0% to about 4%; sodium perborate (e.g., $NaBO_3H_2O$) about 8% to about 16%; TAED about 2% to about 8%; phosphonate (e.g., EDTMPA) 0% to about 1%; carboxymethylcellulose (CMC) 0% to about 2%; polymers (e.g., maleic/acrylic acid copolymer, PVP, PEG) 0-3%; enzymes (calculated as pure enzyme protein) 0.0001-0.1%; minor ingredients (e.g., suds suppressors, perfume, optical brightener) 0-5%.

4) A detergent composition formulated as a granulate having a bulk density of at least 600 g/L comprising linear alkylbenzenesulfonate (calculated as acid) about 8% to about 12%; alcohol ethoxylate (e.g., $C_{12-15}$ alcohol, 7 EO) about 10% to about 25%; sodium carbonate (as $Na_2CO_3$) about 14% to about 22%; soluble silicate (e.g., $Na_2O, 2SiO_2$) about 1% to about 5%; zeolite (e.g., $NaAlSiO_4$) about 25% to about 35%; sodium sulfate (e.g., $Na_2SO_4$) 0% to about 10%; carboxymethylcellulose (CMC) 0% to about 2%; polymers (e.g., maleic/acrylic acid copolymer, PVP, PEG) 1-3%; enzymes (calculated as pure enzyme protein) 0.0001-0.1%; and minor ingredients (e.g., suds suppressors, perfume) 0-5%.

5) An aqueous liquid detergent composition comprising linear alkylbenzenesulfonate (calculated as acid) about 15% to about 21%; alcohol ethoxylate (e.g., $C_{12-15}$ alcohol, 7 EO or $C_{12-15}$ alcohol, 5 EO) about 12% to about 18%; soap as fatty acid (e.g., oleic acid) about 3% to about 13%; alkenylsuccinic acid ($C_{12-14}$) 0% to about 13%; aminoethanol about 8% to about 18%; citric acid about 2% to about 8%; phosphonate 0% to about 3%; polymers (e.g., PVP, PEG) 0% to about 3%; borate (e.g., $B_4O_7$) 0% to about 2%; ethanol 0% to about 3%; propylene glycol about 8% to about 14%; enzymes (calculated as pure enzyme protein) 0.0001-0.1%; and minor ingredients (e.g., dispersants, suds suppressors, perfume, optical brightener) 0-5%.

6) An aqueous structured liquid detergent composition comprising linear alkylbenzenesulfonate (calculated as acid) about 15% to about 21%; alcohol ethoxylate (e.g., $C_{12-15}$ alcohol, 7 EO, or $C_{12-15}$ alcohol, 5 EO) 3-9%; soap as fatty acid (e.g., oleic acid) about 3% to about 10%; zeolite (as $NaAlSiO_4$) about 14% to about 22%; potassium citrate about 9% to about 18%; borate (e.g., $B_4O_7$) 0% to about 2%; carboxymethylcellulose (CMC) 0% to about 2%; polymers (e.g., PEG, PVP) 0% to about 3%; anchoring polymers (e.g., lauryl methacrylate/acrylic acid copolymer); molar ratio 25:1, MW 3800) 0% to about 3%; glycerol 0% to about 5%; enzymes (calculated as pure enzyme protein) 0.0001-0.1%; and minor ingredients (e.g., dispersants, suds suppressors, perfume, optical brighteners) 0-5%.

7) A detergent composition formulated as a granulate having a bulk density of at least 600 g/L comprising fatty alcohol sulfate about 5% to about 10%; ethoxylated fatty acid monoethanolamide about 3% to about 9%; soap as fatty acid 0-3%; sodium carbonate (e.g., $Na_2CO_3$) about 5% to about 10%; Soluble silicate (e.g., $Na_2O, 2SiO_2$) about 1% to about 4%; zeolite (e.g., $NaAlSiO_4$) about 20% to about 40%; sodium sulfate (e.g., $Na_2SO_4$) about 2% to about 8%; sodium perborate (e.g., $NaBO_3H_2O$) about 12% to about 18%; TAED about 2% to about 7%; polymers (e.g., maleic/acrylic acid copolymer, PEG) about 1% to about 5%; enzymes (calculated as pure enzyme protein) 0.0001-0.1%; and minor ingredients (e.g., optical brightener, suds suppressors, perfume) 0-5%.

8) A detergent composition formulated as a granulate comprising linear alkylbenzenesulfonate (calculated as acid) about 8% to about 14%; ethoxylated fatty acid monoethanolamide about 5% to about 11%; soap as fatty acid 0% to about 3%; sodium carbonate (e.g., $Na_2CO_3$) about 4% to about 10%; soluble silicate ($Na_2O, 2SiO_2$) about 1% to about 4%; zeolite (e.g., $NaAlSiO_4$) about 30% to about 50%; sodium sulfate (e.g., $Na_2SO_4$) about 3% to about 11%; sodium citrate (e.g., $C_6H_5Na_3O_7$) about 5% to about 12%; polymers (e.g., PVP, maleic/acrylic acid copolymer, PEG) about 1% to about 5%; enzymes (calculated as pure enzyme protein) 0.0001-0.1%; and minor ingredients (e.g., suds suppressors, perfume) 0-5%.

9) A detergent composition formulated as a granulate comprising linear alkylbenzenesulfonate (calculated as acid) about 6% to about 12%; nonionic surfactant about 1% to about 4%; soap as fatty acid about 2% to about 6%; sodium carbonate (e.g., $Na_2CO_3$) about 14% to about 22%; zeolite (e.g., $NaAlSiO_4$) about 18% to about 32%; sodium sulfate (e.g., $Na_2SO_4$) about 5% to about 20%; sodium citrate (e.g., $C_6H_5Na_3O_7$) about 3% to about 8%; sodium perborate (e.g., $NaBO_3H_2O$) about 4% to about 9%; bleach activator (e.g., NOBS or TAED) about 1% to about 5%; carboxymethylcellulose (CMC) 0% to about 2%; polymers (e.g., polycarboxylate or PEG) about 1% to about 5%; enzymes (calculated as pure enzyme protein) 0.0001-0.1%; and minor ingredients (e.g., optical brightener, perfume) 0-5%.

10) An aqueous liquid detergent composition comprising linear alkylbenzenesulfonate (calculated as acid) about 15% to about 23%; alcohol ethoxysulfate (e.g., $C_{12-15}$ alcohol, 2-3 EO) about 8% to about 15%; alcohol ethoxylate (e.g., $C_{12-15}$ alcohol, 7 EO, or $C_{12-15}$ alcohol, 5 EO) about 3% to about 9%; soap as fatty acid (e.g., lauric acid) 0% to about 3%; aminoethanol about 1% to about 5%; sodium citrate about 5% to about 10%; hydrotrope (e.g., sodium toluensulfonate) about 2% to about 6%; borate (e.g., $B_4O_7$) 0% to about 2%; carboxymethylcellulose 0% to about 1%; ethanol about 1% to about 3%; propylene glycol about 2% to about 5%; enzymes (calculated as pure enzyme protein) 0.0001-0.1%; and minor ingredients (e.g., polymers, dispersants, perfume, optical brighteners) 0-5%.

11) An aqueous liquid detergent composition comprising linear alkylbenzenesulfonate (calculated as acid) about 20% to about 32%; alcohol ethoxylate (e.g., $C_{12-15}$ alcohol, 7 EO, or $C_{12-15}$ alcohol, 5 EO) 6-12%; aminoethanol about 2% to about 6%; citric acid about 8% to about 14%; borate (e.g., $B_4O_7$) about 1% to about 3%; polymer (e.g., maleic/acrylic acid copolymer, anchoring polymer, such as lauryl methacrylate/acrylic acid copolymer) 0% to about 3%; glycerol about 3% to about 8%; enzymes (calculated as pure enzyme protein) 0.0001-0.1%; and minor ingredients (e.g., hydrotropes, dispersants, perfume, optical brighteners) 0-5%.

12) A detergent composition formulated as a granulate having a bulk density of at least 600 g/L comprising anionic surfactant (linear alkylbenzenesulfonate, alkyl sulfate, α-olefinsulfonate, α-sulfo fatty acid methyl esters, alkanesulfonates, soap) about 25% to about 40%; nonionic surfactant (e.g., alcohol ethoxylate) about 1% to about 10%; sodium carbonate (e.g., $Na_2CO_3$) about 8% to about 25%; soluble silicates (e.g., $Na_2O$, $2SiO_2$) about 5% to about 15%; sodium sulfate (e.g., $Na_2SO_4$) 0% to about 5%; zeolite ($NaAlSiO_4$) about 15% to about 28%; sodium perborate (e.g., $NaBO_3 4H_2O$) 0% to about 20%; bleach activator (TAED or NOBS) about 0% to about 5%; enzymes (calculated as pure enzyme protein) 0.0001-0.1%; minor ingredients (e.g., perfume, optical brighteners) 0-3%.

13) Detergent compositions as described in compositions 1)-12) supra, wherein all or part of the linear alkylbenzenesulfonate is replaced by ($C_{12}$-$C_{18}$) alkyl sulfate.

14) A detergent composition formulated as a granulate having a bulk density of at least 600 g/L comprising ($C_{12}$-$C_{18}$) alkyl sulfate about 9% to about 15%; alcohol ethoxylate about 3% to about 6%; polyhydroxy alkyl fatty acid amide about 1% to about 5%; zeolite (e.g., $NaAlSiO_4$) about 10% to about 20%; layered disilicate (e.g., SK56 from Hoechst) about 10% to about 20%; sodium carbonate (e.g., $Na_2CO_3$) about 3% to about 12%; soluble silicate (e.g., $Na_2O$, $2SiO_2$) 0% to about 6%; sodium citrate about 4% to about 8%; sodium percarbonate about 13% to about 22%; TAED about 3% to about 8%; polymers (e.g., polycarboxylates and PVP) 0% to about 5%; enzymes (calculated as pure enzyme protein) 0.0001-0.1%; and minor ingredients (e.g., optical brightener, photobleach, perfume, suds suppressors) 0-5%.

15) A detergent composition formulated as a granulate having a bulk density of at least 600 g/L comprising ($C_{12}$-$C_{18}$) alkyl sulfate about 4% to about 8%; alcohol ethoxylate about 11% to about 15%; soap about 1% to about 4%; zeolite MAP or zeolite A about 35% to about 45%; sodium carbonate (as $Na_2CO_3$) about 2% to about 8%; soluble silicate (e.g., $Na_2O$, $2SiO_2$) 0% to about 4%; sodium percarbonate about 13% to about 22%; TAED 1-8%; carboxymethylcellulose (CMC) 0% to about 3%; polymers (e.g., polycarboxylates and PVP) 0% to about 3%; enzymes (calculated as pure enzyme protein) 0.0001-0.1%; and minor ingredients (e.g., optical brightener, phosphonate, perfume) 0-3%.

16) Detergent formulations as described in 1)-15) supra, which contain a stabilized or encapsulated peracid, either as an additional component or as a substitute for already specified bleach systems.

17) Detergent compositions as described supra in 1), 3), 7), 9), and 12), wherein perborate is replaced by percarbonate.

18) Detergent compositions as described supra in 1), 3), 7), 9), 12), 14), and 15), which additionally contains a manganese catalyst.

19) Detergent composition formulated as a non-aqueous detergent liquid comprising a liquid nonionic surfactant such as, e.g., linear alkoxylated primary alcohol, a builder system (e.g., phosphate), an enzyme(s), and alkali. The detergent may also comprise anionic surfactant and/or a bleach system.

The α-amylase variant may be incorporated in concentrations conventionally employed in detergents. It is at present contemplated that, in the detergent composition, the α-amylase variant may be added in an amount corresponding to 0.00001-1.0 mg (calculated as pure enzyme protein) of α-amylase variant per liter of wash liquor.

In another aspect, the 2,6-β-D-fructan hydrolase can be incorporated in detergent compositions and used for removal/cleaning of biofilm present on household and/or industrial textile/laundry.

The detergent composition may for example be formulated as a hand or machine laundry detergent composition, including a laundry additive composition suitable for pre-treatment of stained fabrics and a rinse added fabric softener composition, or be formulated as a detergent composition for use in general household hard surface cleaning operations, or be formulated for hand or machine dishwashing operations.

In a specific aspect, the detergent composition can comprise 2,6-β-D-fructan hydrolase, one or more α-amylase variants, and one or more other cleaning enzymes, such as a protease, a lipase, a cutinase, a carbohydrase, a cellulase, a pectinase, a mannanase, an arabinase, a galactanase, a xylanase, an oxidase, a laccase, and/or a peroxidase, and/or combinations thereof.

In general the properties of the chosen enzyme(s) should be compatible with the selected detergent, (e.g., pH-optimum, compatibility with other enzymatic and non-enzymatic ingredients, etc.), and the enzyme(s) should be present in effective amounts.

Proteases: suitable proteases include those of animal, vegetable or microbial origin. Exemplary proteases include those derived from microorganisms. Chemically modified or protein engineered mutants are included. The protease may be a serine protease or a metalloprotease, an alkaline microbial protease or a trypsin-like protease. Examples of alkaline proteases are subtilisins, especially those derived from *Bacillus*, e.g., subtilisin Novo, subtilisin Carlsberg, subtilisin 309, subtilisin 147, and subtilisin 168 (see, e.g., WO 89/06279). Examples of trypsin-like proteases are trypsin (e.g., of porcine or bovine origin), and *Fusarium* proteases (see, e.g., WO 89/06270 and WO 94/25583). Examples of useful proteases also include but are not limited to the variants described in WO 92/19729, WO 98/20115, WO 98/20116, and WO 98/34946. Exemplary commercially available protease enzymes include Alcalase®, Savinase®, Primase™, Duralase™, Esperase®, and Kannase™ (Novo Nordisk A/S); Maxatase®, Maxacal™, Maxapem™, Properase™, Purafect®, Purafect OxP™, FN2™, and FN3™ (Genencor International, Inc.).

Lipases: suitable lipases include those of bacterial or fungal origin. Chemically modified or protein engineered mutants are included. Examples of useful lipases include but are not limited to lipases from *Humicola* (synonym *Thermomyces*), e.g. from *H. lanuginosa* (*T. lanuginosus*) (see e.g., EP 258068 and EP 305216), from *H. insolens* (see e.g., WO 96/13580); a *Pseudomonas* lipase (e.g. from *P. alcaligenes* or *P. pseudoalcaligenes*; see, e.g., EP 218 272), *P. cepacia* (see e.g., EP 331 376), *P. stutzeri* (see e.g., GB 1,372,034), *P. fluorescens*, *Pseudomonas* sp. strain SD 705 (see e.g., WO 95/06720 and WO 96/27002), *P. wisconsinensis* (see e.g. WO 96/12012); a *Bacillus* lipase (e.g. from *B. subtilis*; see e.g., Dartois et al. *Biochemica et Biophysica Acta*, 1131: 253-360

(1993)), *B. stearothermophilus* (see e.g., JP 64/744992), or *B. pumilus* (see e.g., WO 91/16422). Additional lipase variants contemplated for use in the formulations include those described for example in: WO 92/05249, WO 94/01541, WO 95/35381, WO 96/00292, WO 95/30744, WO 94/25578, WO 95/14783, WO 95/22615, WO 97/04079, WO 97/07202, EP 407225, and EP 260105. Some commercially available lipase enzymes include Lipolase® and Lipolase® Ultra (Novo Nordisk A/S).

Polyesterases: Suitable polyesterases include but are not limited to those described in International PCT Applications WO 01/34899 and WO 01/14629, and can be included in any combination with other enzymes discussed herein.

Amylases: The compositions can be combined with other α-amylases, such as non-production enhanced α-amylase. These can include commercially available amylases, such as but not limited to Duramyl®, Termamyl™, Fungamyl® and BAN™ (Novo Nordisk A/S), Rapidase®, and Purastar® (from Genencor International, Inc.).

Cellulases: Cellulases can be added to the compositions. Suitable cellulases include those of bacterial or fungal origin. Chemically modified or protein engineered mutants are included. Suitable cellulases include cellulases from the genera *Bacillus, Pseudomonas, Humicola, Fusarium, Thielavia, Acremonium*, e.g. the fungal cellulases produced from *Humicola insolens, Myceliophthora thermophila* and *Fusarium oxysporum* disclosed for example in U.S. Pat. Nos. 4,435,307; 5,648,263; 5,691,178; 5,776,757; and WO 89/09259. Exemplary cellulases contemplated for use are those having color care benefit for the textile. Examples of such cellulases are cellulases described in, for example, EP 0495257, EP 0531372, WO 96/11262, WO 96/29397, and WO 98/08940. Other examples are cellulase variants, such as those described in WO 94/07998; WO 98/12307; WO 95/24471; PCT/DK98/00299; EP 531315; U.S. Pat. Nos. 5,457,046; 5,686,593; and 5,763,254. Commercially available cellulases include Celluzyme® and Carezyme® (Novo Nordisk A/S); Clazinase™ and Puradax® HA (Genencor International, Inc.); and KAC-500(B)™ (Kao Corporation).

Peroxidases/Oxidases: Suitable peroxidases/oxidases contemplated for use in the compositions include those of plant, bacterial or fungal origin. Chemically modified or protein engineered mutants are included. Examples of useful peroxidases include peroxidases from *Coprinus*, e.g. from *C. cinereus*, and variants thereof as those described in WO 93/24618, WO 95/10602, and WO 98/15257. Commercially available peroxidases include for example Guardzyme™ (Novo Nordisk A/S).

The detergent enzyme(s) may be included in a detergent composition by adding separate additives containing one or more enzymes, or by adding a combined additive comprising all of these enzymes. A detergent additive, i.e. a separate additive or a combined additive, can be formulated e.g., as a granulate, a liquid, a slurry, etc. Exemplary detergent additive formulations are granulates, in particular non-dusting granulates, liquids, in particular stabilized liquids, or slurries.

Non-dusting granulates may be produced, e.g., as disclosed in U.S. Pat. Nos. 4,106,991 and 4,661,452 and may optionally be coated by methods known in the art. Examples of waxy coating materials are poly(ethylene oxide) products (e.g., polyethyleneglycol, PEG) with mean molar weights of 1,000 to 20,000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in, for example, GB 1483591. Liquid enzyme preparations may, for instance, be stabilized by adding a polyol such as propylene glycol, a sugar or sugar alcohol, lactic acid or boric acid according to established methods. Protected enzymes may be prepared according to the method disclosed in EP 238,216.

The detergent composition may be in any convenient form, e.g., a bar, a tablet, a powder, a granule, a paste, or a liquid. A liquid detergent may be aqueous, typically containing up to about 70% water, and 0% to about 30% organic solvent. Compact detergent gels containing 30% or less water are also contemplated. The detergent composition comprises one or more surfactants, which may be non-ionic including semi-polar and/or anionic and/or cationic and/or zwitterionic. The surfactants are typically present at a level of from 0.1% to 60% by weight.

When included therein the detergent will typically contain from about 1% to about 40% of an anionic surfactant, such as linear alkylbenzenesulfonate, α-olefinsulfonate, alkyl sulfate (fatty alcohol sulfate), alcohol ethoxysulfate, secondary alkanesulfonate, α-sulfo fatty acid methyl ester, alkyl- or alkenylsuccinic acid, or soap.

When included therein, the detergent will usually contain from about 0.2% to about 40% of a non-ionic surfactant such as alcohol ethoxylate, nonylphenol ethoxylate, alkylpolyglycoside, alkyldimethylamineoxide, ethoxylated fatty acid monoethanolamide, fatty acid monoethanolamide, polyhydroxy alkyl fatty acid amide, or N-acyl-N-alkyl derivatives of glucosamine ("glucamides").

The detergent may contain 0% to about 65% of a detergent builder or complexing agent such as zeolite, diphosphate, triphosphate, phosphonate, carbonate, citrate, nitrilotriacetic acid, ethylenediaminetetraacetic acid (EDTA), diethylenetriaminepentaacetic acid, alkyl- or alkenylsuccinic acid, soluble silicates or layered silicates (e.g. SKS-6 from Hoechst).

The detergent may comprise one or more polymers. Examples are carboxymethylcellulose (CMC), poly(vinylpyrrolidone) (PVP), poly(ethylene glycol) (PEG), poly (vinyl alcohol) (PVA), poly(vinylpyridine-N-oxide), poly(vinylimidazole), polycarboxylates e.g., polyacrylates, maleic/acrylic acid copolymers), and lauryl methacrylate/acrylic acid copolymers.

The detergent may contain a bleaching system that may comprise a $H_2O_2$ source, such as perborate or percarbonate, which may be combined with a peracid-forming bleach activator (e.g., tetraacetylethylenediamine or nonanoyloxybenzenesulfonate). Alternatively, the bleaching system may comprise peroxyacids (e.g. the amide, imide, or sulfone type peroxyacids). The bleaching system can also be an enzymatic bleaching system.

The enzyme(s) of the detergent composition may be stabilized using conventional stabilizing agents, e.g., as polyol (e.g., propylene glycol or glycerol), a sugar or sugar alcohol, lactic acid, boric acid, or a boric acid derivative (e.g., an aromatic borate ester), or a phenyl boronic acid derivative (e.g., 4-formylphenyl boronic acid). The composition may be formulated as described in WO 92/19709 and WO 92/19708.

The detergent may also contain other conventional detergent ingredients such as e.g. fabric conditioners including clays, foam boosters, suds suppressors, anti-corrosion agents, soil-suspending agents, anti-soil redeposition agents, dyes, bactericides, optical brighteners, hydrotropes, tarnish inhibitors, or perfumes.

It is at present contemplated that in the detergent compositions, in particular the enzyme variants, may be added in an amount corresponding to about 0.01 to about 100 mg of enzyme protein per liter of wash liquor, for example from about 0.05 to about 5.0 mg of enzyme protein per liter of wash liquor, in particular 0.1 to about 1.0 mg of enzyme protein per liter of wash liquor.

5.3 Methods of Assessing Detergent Compositions

Numerous α-amylase cleaning assays exist. Exemplary description of testing cleaning includes the following.

A "swatch" is a piece of material such as a fabric that has a stain applied thereto. The material can be, for example, fabrics made of cotton, polyester or mixtures of natural and synthetic fibers. The swatch can further be paper, such as filter paper or nitrocellulose, or a piece of a hard material such as ceramic, metal, or glass. For amylases, the stain is starch based, but can include blood, milk, ink, grass, tea, wine, spinach, gravy, chocolate egg, cheese, clay, pigment, oil, or mixtures of these compounds.

A "smaller swatch" is a section of the swatch that has been cut with a single hole punch device, or has been cut with a custom manufactured 96-hole punch device, where the pattern of the multi-hole punch is matched to standard 96-well microtiter plates, or the section has been otherwise removed from the swatch. The swatch can be of textile, paper, metal, or other suitable material. The smaller swatch can have the stain affixed either before or after it is placed into the well of a 24-, 48- or 96-well microtiter plate. The "smaller swatch" can also be made by applying a stain to a small piece of material. The smaller swatch is a stained piece of fabric that is 5/8" in diameter or less, such as a swatch that is 0.25" in diameter. The custom manufactured punch is designed in such a manner that it delivers 96 swatches simultaneously to all wells of a 96-well plate. The device allows delivery of more than one swatch per well by simply loading the same 96-well plate multiple times. Multi-hole punch devices can be conceived of to deliver simultaneously swatches to any format plate, including but not limited to 24-well, 48-well, and 96-well plates. In another conceivable method, the soiled test platform can be a bead made of either metal, plastic, glass, ceramic, or other suitable material that is coated with the soil substrate. The one or more coated beads are then placed into wells of 96-, 48-, or 24-well plates or larger formats, containing suitable buffer and enzyme. In this case, supernatant can be examined for released soil either by direct absorbance measurement or after a secondary color development reaction. Analysis of the released soil might also be taken by mass spectral analysis. A further microscreening assay might be to deliver and secure a swatch, for example, an indigo dyed denim, to a well of a multiwell plate and to add particles such as sand or larger particles such as, for example, garnet sieved to include particles of 6 to 8 or 9 gauge, and agitate the plate so as to cause abrasion of the swatch by the added particles. This assay has been used in for example the assessment of cellulases in stone washing applications. The effectiveness of the enzyme is judged by either color release (i.e., released indigo that is dissolved in dimethylsulfoxide and absorbance at $A_{600}$ nm is measured) to the reaction buffer or by reflectance measurements of the abraded swatch.

When, for example, untreated BMI (blood/milk/ink) swatches are washed in detergent without bleach, a large portion of the ink is released even without the help of a protease. Adding a protease leads to a small increase in ink release, which can be hard to quantify over the large background. The present invention provides a treatment protocol that allows one to control the degree of fixation of a stain. As a result, it is possible to produce swatches that, for example, release varying amounts of stain when washed in the absence of the enzyme being tested. The use of fixed swatches leads to a dramatic improvement of the signal-to-noise ratio in the wash assays. Furthermore, by varying the degree of fixation, one can generate stains that give optimum results under the various cleaning conditions.

Swatches having stains of known "strength" on various types of material are commercially available (EMPA, St. Gallen, Switzerland; wfk—Testgewebe GmbH, Krefeld Germany; or Center for Test Materials, Vlaardingen, The Netherlands) and/or can be made by the practitioner (Morris and Prato, *Textile Research Journal* 52(4): 280 286 (1982)). Exemplary swatches are a blood/milk/ink (BMI) stain on a cotton-containing fabric, a spinach stain on a cotton-containing fabric, or grass on a cotton-containing fabric, and chocolate/milk/soot on a cotton-containing fabric.

In one aspect, a BMI stain can be fixed to cotton with 0.0003% to 0.3% hydrogen peroxide. Other combinations include grass or spinach fixed with 0.001% to 1% glutaraldehyde, gelatin and Coomassie stain fixed with 0.001% to 1% glutaraldehyde, or chocolate, milk and soot fixed with 0.001% to 1% glutaraldehyde.

The swatch can also be agitated during incubation with the enzyme and/or detergent formulation. Wash performance data is dependent on the orientation of the swatches in the wells (horizontal versus vertical), particularly in the 96-well plate. This would indicate that mixing was insufficient during the incubation period. Although there are a number of ways to ensure sufficient agitation during incubation, a plate holder in which the microtiter plate is sandwiched between two plates of aluminum can be constructed. This can be as simple as placing, for example, an adhesive plate sealer over the wells then clamping the two aluminum plates to the 96-well plate with any type of appropriate, commercially available clamps. It can then be mounted in a commercial incubator shaker. Setting the shaker to about 400 rpm results in very efficient mixing, while leakage or cross-contamination is efficiently prevented by the holder.

Trinitrobenzenesulfonic acid (TNBS) can be used to quantify the concentration of amino groups in the wash liquor. This can serve as a measure of the amount of protein that was removed from the swatch (see, e.g., Cayot and Tainturier, *Anal. Biochem.* 249: 184 0200 (1997)). However, if a detergent or an enzyme sample leads to the formation of unusually small peptide fragments (for example, from the presence of peptidases in the sample), then one will obtain a larger TNBS signal, i.e., more "noise".

Another means of measuring wash performance of blood/milk/ink that is based on ink release. Proteolysis of protein on the swatches leads to the release of ink particles which can be quantified by measuring the absorbance of the wash liquor. The absorbance can be measured at any wavelength between 350 and 800 nm. In another aspect, the wavelength is measured at 410 nm or 620 nm. The wash liquor can also be examined to determine the wash performance on stains containing grass, spinach, gelatin or Coomassie stain. Exemplary wavelengths for these stains include and 670 nm for spinach or grass and 620 nm for gelatin or Coomassie. For example, an aliquot of the wash liquor (typically 100 150 μL from a 96-well microplate, for example) is removed and placed in a cuvette or multiwell microplate. This is then placed in a spectrophotometer and the absorbance is read at an appropriate wavelength.

The system can also be used to determine an enzyme and/or detergent composition for dish washing, for example, using a blood/milk/ink stain on a suitable substrate such as cloth, plastic or ceramic.

In one aspect, the a BMI stain is fixed to cotton by applying 0.3% hydrogen peroxide to the BMI/cotton swatch for 30 minutes at 25° C. or by applying 0.03% hydrogen peroxide to the BMI/cotton swatch for 30 minutes at 60° C. Smaller swatches of approximately 0.25" are cut from the BMI/cotton swatch and placed in the wells of a 96-well microtiter plate. Into each well, a known mixture of a detergent composition and an enzyme such as a variant protein is placed. After placing an adhesive plate sealer onto the top of the microtiter plate, the microtiter plate is clamped to an aluminum plate and agitated on an orbital shaker at approximately 250 rpm for about 10 to 60 minutes. At the end of this time, the supernatants are transferred to wells in a new microtiter plate and the absorbance of the ink at 620 nm is measured. This can be similarly tests with spinach stains or grass stains fixed to cotton by applying 0.01% glutaraldehyde to the spinach/cotton swatch or grass/cotton swatch for 30 minutes at 25° C. The same can be done with chocolate, milk, and/or soot stains. For additional variations and conditions for blood/milk/ink assays, refer to U.S. Pat. No. 7,122,334 (Genencor International, Inc.).

5.4 Textile Desizing Compositions and Use

Also contemplated are compositions and methods of treating fabrics (e.g. to desize a textile) using one or more of the enzyme variants. The enzyme variants can be used in any fabric-treating method, which are well known in the art, see, e.g., U.S. Pat. No. 6,077,316. For example, in one aspect, the feel and appearance of a fabric is improved by a method comprising contacting the fabric with an enzyme variants in a solution. In one aspect, the fabric is treated with the solution under pressure.

In one aspect, the enzymes are applied during or after the weaving of textiles, or during the desizing stage, or one or more additional fabric processing steps. During the weaving of textiles, the threads are exposed to considerable mechanical strain. Prior to weaving on mechanical looms, warp yarns are often coated with sizing starch or starch derivatives in order to increase their tensile strength and to prevent breaking. The enzymes can be applied to remove these sizing starch or starch derivatives. After the textiles have been woven, a fabric can proceed to a desizing stage. This can be followed by one or more additional fabric processing steps. Desizing is the act of removing size from textiles. After weaving, the size coating must be removed before further processing the fabric in order to ensure a homogeneous and wash-proof result. Also provided is a method of desizing comprising enzymatic hydrolysis of the size by the action of an enzyme variant.

The enzyme variants can be used alone or with other desizing chemical reagents and/or desizing enzymes to desize fabrics, including cotton-containing fabrics, as detergent additives, e.g., in aqueous compositions. The enzyme variants can also be used in compositions and methods for producing a stonewashed look on indigo-dyed denim fabric and garments. For the manufacture of clothes, the fabric can be cut and sewn into clothes or garments, which is afterwards finished. In particular, for the manufacture of denim jeans, different enzymatic finishing methods have been developed. The finishing of denim garment normally is initiated with an enzymatic desizing step, during which garments are subjected to the action of amylolytic enzymes in order to provide softness to the fabric and make the cotton more accessible to the subsequent enzymatic finishing steps. The enzyme variants can be used in methods of finishing denim garments (e.g., a "bio-stoning process"), enzymatic desizing and providing softness to fabrics, and/or finishing process.

5.5 Starch Processing Compositions and Use

In another aspect, compositions with the disclosed α-amylase variants can be utilized for starch liquefaction or saccharification.

One aspect are compositions and uses of compositions to produce sweeteners from starch. A "traditional" process for conversion of starch to fructose syrups normally consists of three consecutive enzymatic processes, viz. a liquefaction process followed by a saccharification process, and an isomerization process. During the liquefaction process, starch is degraded to dextrins by an α-amylase variant at pH values between about 5.5 and about 6.2 and at temperatures of about 95° C. to about 160° C. for a period of approximately 2 hours. In order to ensure an optimal enzyme stability under these conditions, 1 mM of calcium is added (40 ppm free calcium ions). Starch processing is useful for producing alcohol (e.g., cereal liquefaction for fuel and potable alcohol, alcohol brewing), starch liquefaction for sweetener production, cane sugar processing, and other food related starch processing goals. Other conditions can be used for different α-amylase variants.

After the liquefaction process, the dextrins are converted into dextrose by addition of a glucoamylase (e.g., AMG™) and a debranching enzyme, such as an isoamylase or a pullulanase (e.g., Promozyme®). One pullanase example is pullulanase strain 139 raise in *B. licheniformis* and derived from BML 780 (Δamy gene; amplifiabile PU gene from *B. deramificans* at the cat locus with cat$^R$ marker; Δ spo II AC; Δ apr L; and Δ endo-glu C, which is two protease genes deleted to prevent pullulanase hydrolysis). Before this step, the pH is reduced to a value below about 4.5, maintaining the high temperature (above 95° C.), and the liquefying α-amylase variant activity is denatured. The temperature is lowered to 60° C., and a glucoamylase and a debranching enzyme can be added. The saccharification process proceeds typically for about 24 to about 72 hours.

After the saccharification process, the pH is increased to a value in the range of about 6.0 to about 8.0 (e.g., pH 7.5), and the calcium is removed by ion exchange. The dextrose syrup is then converted into high fructose syrup using, e.g., an immobilized glucose isomerase (such as Sweetzyme®).

At least one enzymatic improvement of this process can be performed. Reduction of the calcium dependency of the liquefying α-amylase variant. Addition of free calcium is required to ensure adequately high stability of the α-amylase variant, but free calcium strongly inhibits the activity of the glucose isomerase and needs to be removed, by means of an expensive unit operation, to an extent that reduces the level of free calcium to below 3-5 ppm. Cost savings can be obtained if such an operation could be avoided, and the liquefaction process could be performed without addition of free calcium ions.

For example, a less calcium-dependent α-amylase variant, which is stable and highly active at low concentrations of free calcium (<40 ppm) can be utilized in the composition and procedures. Such an α-amylase variant should have a pH optimum at a pH in the range of about 4.5 to about 6.5 (e.g., in the range of about 4.5 to about 5.5).

α-amylase variants can be used in laboratory and industrial settings to hydrolyze starch or any maltodextrine-comprising compound for a variety of purposes. These α-amylase variants can be used alone to provide specific hydrolysis or can be combined with other amylases to provide a "cocktail" with a broad spectrum of activity. Exemplary uses include the removal or partial or complete hydrolysis of starch or any maltodextrine-comprising compound from biological, food, animal feed, pharmaceutical, or industrial samples.

One exemplary use is in a fermentation process wherein a starch substrate is liquefied and/or saccharified in the presence of the enzyme variant(s) to produce glucose and/or maltose suitable for conversion into a fermentation product by a fermenting organism, such as a yeast. Such fermentation processes include a process for producing ethanol for fuel or drinking ethanol (portable alcohol), a process for producing a beverage, a process for producing desired organic compounds (e.g., such as citric acid, itaconic acid, lactic acid, gluconic acid, sodium gluconate, calcium gluconate, potassium gluconate, glucono delta lactone, or sodium erythorbate), ketones, amino acids (such as glutamic acid, sodium monoglutaminate), but also more complex compounds (e.g., antibiotics, such as penicillin, tetracyclin), enzymes, vitamins (e.g., riboflavin, vitamin B12, β-carotene), and hormones, which are difficult to produce synthetically.

The starch to be processed may be a highly refined starch quality, for example at least 90%, at least 95%, at least 97%, or at least 99.5% pure. Alternatively, the starch can be a more crude starch containing material comprising milled whole grain including non-starch fractions such as germ residues and fibers. The raw material, such as whole grain, is milled in order to open up the structure and allowing for further processing. Two milling processes can be used: wet and dry milling. Also, corn grits and milled corn grits may be used.

Dry milled grain will, in addition to starch, comprise significant amounts of non-starch carbohydrate compounds. When such a heterogeneous material is processed by jet cooking often only a partial gelatinization of the starch is achieved. As the enzyme variants have a high activity towards ungelatinized starch, the enzyme variants are advantageously applied in a process comprising liquefaction and/or saccharification jet cooked dry milled starch.

Furthermore, due to the superior hydrolysis activity of the enzyme variant, the need for glucoamylase during the saccharification step is greatly reduced. This allows saccharification to be performed at very low levels of glucoamylase activity, and glucoamylase activity is either absent or if present, then present in an amount of no more than or even less than 0.5 AGU/g DS (activity of the GU per gram of dry solids (DS)); no more than or even less than 0.4 AGU/g DS; no more than or even less than about 0.3 AGU/g DS; and less than 0.1 AGU, such as no more than or even less than about 0.05 AGU/g DS of starch substrate. Expressed in mg enzyme protein, the enzyme having glucoamylase activity is either absent or present in an in an amount of no more than or even less than about 0.5 mg EP/g DS (enzyme protein per gram of dry solids); no more than or even less than about 0.4 mg EP/g DS; no more than or even less than about 0.3 mg EP/g DS; and no more than or even less than about 0.1 mg EP/g DS, such as no more than or even less than about 0.05 mg EP/g DS or no more than or even less than 0.02 mg EP/g DS of starch substrate. The glucoamylase may be derived from a strain within *Aspergillus* sp., *Talaromyces* sp., *Pachykytospora* sp., or *Trametes* sp., with exemplary examples being *Aspergillus niger, Talaromyces emersonii, Trametes cingulata*, or *Pachykytospora papyracea*.

Expressed in mg enzyme protein, the enzyme variant may be dosed in amounts of no more than or even less than 0.5 mg EP/g DS; no more than or even less than 0.4 mg EP/g DS; no more than or even less than 0.3 mg EP/g DS; or no more than or even less than 0.1 mg EP/g DS, such as no more than or even less than 0.05 mg EP/g DS or no more than or even less than 0.02 mg EP/g DS of starch substrate. The enzyme variant of the first aspect may be dosed in amounts of 0.05 to 10.0 AFAU/g DS, such as 0.1 to 5.0 AFAU/g DS, such as from 0.25 to 2.5 AFAU/g DS starch.

The process may comprise a) contacting a starch substrate with an enzyme variant comprising a catalytic module having α-amylase activity and a carbohydrate-binding module, e.g., the polypeptide of the first aspect; b) incubating said starch substrate with said enzyme variant for a time and at a temperature sufficient to achieve conversion of at least 90%, or at least 92%, at least 94%, at least 95%, at least 96%, at least 97%, at least 98%, at least 99%, at least 99.5% w/w of said starch substrate into fermentable sugars; c) fermenting to produce a fermentation product; and d) optionally recovering the fermentation product. During the process steps b) and/or c), an enzyme having glucoamylase activity is either absent or present in an amount from 0.001 to 2.0 AGU/g DS, from 0.01 to 1.5 AGU/g DS, from 0.05 to 1.0 AGU/g DS, from 0.01 to 0.5 AGU/g DS. The enzyme having glucoamylase activity can either absent or present in an in an amount of no more than or even less than 0.5 AGU/g DS; no more than or even less than 0.4 AGU/g DS; no more than or even less than 0.3 AGU/g DS; or no more than or even less than 0.1 AGU/g DS, such as no more than or even less than 0.05 AGU/g DS of starch substrate. Expressed in mg enzyme protein, the enzyme having glucoamylase activity is either absent or present in an in an amount of no more than or even less than 0.5 mg EP/g DS; no more than or even less than 0.4 mg EP/g DS; no more than or even less than 0.3 mg EP/g DS; or no more than or even less than 0.1 mg EP/g DS, such as no more than or even less than 0.05 mg EP/g DS or no more than or even less than 0.02 mg EP/g DS of starch substrate. In the process steps a), b), c), and/or d) may be performed separately or simultaneously.

In another aspect the process may comprise: a) contacting a starch substrate with a yeast cell transformed to express a enzyme variant comprising a catalytic module having α-amylase activity and a carbohydrate-binding module, e.g., the polypeptide of the first and/or second aspect; b) incubating said starch substrate with said yeast for a time and at a temperature sufficient to achieve conversion of at least 90% w/w of said starch substrate into fermentable sugars; c) fermenting to produce ethanol; d) optionally recovering ethanol. The steps a), b), and c) may performed separately or simultaneously.

In yet another aspect, the process comprising hydrolysis of a slurry of gelatinized or granular starch, in particular hydrolysis of granular starch into a soluble starch hydrolysate at a temperature below the initial gelatinization temperature of said granular starch. In addition to being contacted with a polypeptide comprising a catalytic module having α-amylase activity and a carbohydrate-binding module, e.g., the polypeptide of the first aspect, the starch may be contacted with an enzyme selected from the group consisting of a fungal α-amylase (EC 3.2.1.1) and one or more of the following: a β-amylase (EC 3.2.1.2), and a glucoamylase (EC 3.2.1.3). In an embodiment further another amylolytic enzyme or a debranching enzyme, such as an isoamylase (EC 3.2.1.68), or a pullulanases (EC 3.2.1.41) may be added to the α-amylase variant.

In an embodiment, the process is conducted at a temperature below the initial gelatinization temperature. Such processes are oftentimes conducted at least at 30° C., at least 31° C., at least 32° C., at least 33° C., at least 34° C., at least 35° C., at least 36° C., at least 37° C., at least 38° C., at least 39° C., at least 40° C., at least 41° C., at least 42° C., at least 43° C., at least 44° C., at least 45° C., at least 46° C., at least 47° C., at least 48° C., at least 49° C., at least 50° C., at least 51°

C., at least 52° C., at least 53° C., at least 54° C., at least 55° C., at least 56° C., at least 57° C., at least 58° C., at least 59° C., or at least 60° C. The pH at which the process is conducted may in be in the range of about 3.0 to about 7.0, or from about 3.5 to about 6.0, or from about 4.0 to about 5.0. One aspect contemplates a process comprising fermentation, e.g. with a yeast to produce ethanol, e.g., at a temperature around 32° C., such as from 30 to 35° C.

In another aspect, the process comprises simultaneous saccharification and fermentation, e.g., with a yeast to produce ethanol, or another suitable fermentation organism to produce a desired organic compound, such as at a temperature from 30 to 35° C., e.g., at around 32° C.

In the above fermentation processes, the ethanol content reaches at least about 7%, at least about 8%, at least about 9%, at least about 10%, at least about 11%, at least about 12%, at least about 13%, at least about 14%, at least about 15% such as at least about 16% ethanol.

The starch slurry to be used in any of the above aspects may have about 20% to about 55% dry solids granular starch, or about 25% to about 40% dry solids granular starch, or about 30% to about 35% dry solids granular starch. After being contacted with the enzyme variant, the enzyme variant converts the soluble starch into a soluble starch hydrolysate of the granular starch in the amount of at least 85%, at least 86%, at least 87%, at least 88%, at least 89%, at least 90%, at least 91%, at least 92%, at least 93%, at least 94%, at least 95%, at least 96%, at least 97%, at least 98%, or at least 99%.

In another embodiment, the enzyme variant comprises a catalytic module having α-amylase activity and a carbohydrate-binding module, e.g., the polypeptide of the first aspect, is used in a process for liquefaction, saccharification of a gelatinized starch, e.g., but not limited to gelatinization by jet cooking. The process may comprise fermentation to produce a fermentation product, e.g., ethanol. Such a process for producing ethanol from starch-containing material by fermentation comprises: (i) liquefying said starch-containing material with a polypeptide comprising a catalytic module having α-amylase activity and a carbohydrate-binding module, e.g., the polypeptide of the first aspect; (ii) saccharifying the liquefied mash obtained; and (iii) fermenting the material obtained in step (ii) in the presence of a fermenting organism. Optionally the process further comprises recovery of the ethanol. The saccharification and fermentation processes may be carried out as a simultaneous saccharification and fermentation process (SSF process). During the fermentation, the ethanol content reaches at least about 7%, at least about 8%, at least about 9%, at least about 10% such as at least about 11%, at least about 12%, at least about 13%, at least about 14%, at least 15% such as at least about 16% ethanol.

The starch to be processed in the processes of the above aspects may in particular be obtained from tubers, roots, stems, legumes, cereals or whole grain. More specifically, the granular starch may be obtained from corns, cobs, wheat, barley, rye, milo, sago, cassava, tapioca, sorghum, rice, peas, bean, banana, or potatoes. Specially contemplated are both waxy and non-waxy types of corn and barley.

The composition described above may be used for liquefying and/or saccharifying a gelatinized or a granular starch, and a partly gelatinized starch. A partly gelatinized starch is a starch that to some extent is gelatinized, i.e., wherein part of the starch has irreversibly swelled and gelatinized and part of the starch is still present in a granular state.

The composition described above may comprise acid α-amylase variant present in an amount of 0.01 to 10.0 AFAU/g DS, or 0.1 to 5.0 AFAU/g DS, or 0.5 to 3.0 AFAU/ AGU, or 0.3 to 2.0 AFAU/g DS. The composition may be applied in any of the starch processes described above.

As used herein, the term "liquefaction" or "liquefy" means a process by which starch is converted to shorter chain and less viscous dextrins. Generally, this process involves gelatinization of starch simultaneously with or followed by the addition of α-amylase variant. Additional liquefaction inducing enzymes may also optionally be added.

As used herein, the term "primary liquefaction" refers to a step of liquefaction when the slurry's temperature is raised to or near its gelatinization temperature. Subsequent to the raising of the temperature, the slurry is sent through a heat exchanger or jet to temperatures from 200-300° F., e.g., 220-235° F. Subsequent to application to a heat exchange or jet temperature, the slurry is held for a period of 3-10 minutes at that temperature. This step of holding the slurry at 200-300° F. is primary liquefaction.

As used herein, the term "secondary liquefaction" refers the liquefaction step subsequent to primary liquefaction (heating to 200-300° F.), when the slurry is allowed to cool to atmospheric temperature. This cooling step can be 30 minutes to 180 minutes (3 hours), e.g. 90 minutes to 120 minutes (2 hours).

As used herein, the term "minutes of secondary liquefaction" refers to the time that has elapsed from the start of secondary liquefaction, time that the DE is measured.

Another aspect contemplates the additional use of a β-amylase in the composition comprising the α-amylase variant. β-amylases (EC 3.2.1.2) are exo-acting maltogenic amylases, which catalyze the hydrolysis of 1,4-α-glucosidic linkages in to amylose, amylopectin, and related glucose polymers, thereby releasing maltose.

β-amylases have been isolated from various plants and microorganisms (W. M. Fogarty and C. T. Kelly, PROGRESS IN INDUSTRIAL MICROBIOLOGY, vol. 15, pp. 112-115, 1979). These β-amylases are characterized by having optimum temperatures in the range from 40° C. to 65° C., and optimum pH in the range from about 4.5 to about 7.0. Contemplated β-amylases include, but are not limited to, β-amylases from barley Spezyme® BBA 1500, Spezyme® DBA, Optimalt™ ME, Optimalt™ BBA (Genencor International, Inc.); and Novozym™ WBA (Novozymes A/S).

Another enzyme contemplated for use in the composition is a glucoamylase (EC 3.2.1.3). Glucoamylases are derived from a microorganism or a plant. Exemplary glucoamylases are of fungal or bacterial origin. Exemplary bacterial glucoamylases are *Aspergillus* glucoamylases, in particular *A. niger* G1 or G2 glucoamylase (Boel et al. (1984), *EMBO J.* 3(5): 1097-1102), or variants thereof, such as disclosed in WO 92/00381; and WO 00/04136; the *A. awamori* glucoamylase (WO 84/02921); *A. oryzae* (*Agric. Biol. Chem.* (1991), 55(4): 941-949), or variants or fragments thereof.

Other contemplated *Aspergillus* glucoamylase variants include variants to enhance the thermal stability: G137A and G139A (Chen et al. (1996), *Prot. Eng.* 9: 499-505); D257E and D293E/Q (Chen et al. (1995), *Prot. Eng.* 8: 575-582); N182 (Chen et al. (1994), *Biochem. I* 301: 275-281); disulphide bonds, A246C (Fierobe et al. (1996), *Biochemistry,* 35: 8698-8704); and introduction of Pro residues in positions A435 and S436 (Li et al. (1997) *Protein Eng.* 10: 1199-1204. Other contemplated glucoamylases include *Talaromyces* glucoamylases, in particular derived from *Talaromyces emersonii* (WO 99/28448), *Talaromyces leycettanus* (U.S. Pat. No. RE 32,153), *Talaromyces duponti, Talaromyces thermophilus* (U.S. Pat. No. 4,587,215). Bacterial glucoamylases contemplated include glucoamylases from the genus *Clostridium*, in particular *C. thermoamylolyticum* (EP 135138) and *C. ther-*

*mohydrosulfuricum* (WO 86/01831). Exemplary glucoamylases include the glucoamylases derived from *Aspergillus oryzae*, such as a glucoamylase having 50%, 55%, 60%, 65%, 70%, 75%, 80%, 85%, or even 90% homology to the amino acid sequence shown in SEQ ID NO: 2 of WO 00/04136. Also contemplated are the commercial glucoamylases such as AMG 200L; AMG 300 L; SAN™ SUPER and AMG™ E (from Novozymes); OPTIDEX® 300 (from Genencor International, Inc.); AMIGASE™ and AMIGASE™ PLUS (from DSM); G-ZYME® G900 (from Enzyme Bio-Systems); G-ZYME® G990 ZR (*A. niger* glucoamylase and low protease content).

Glucoamylases may be added in an amount of 0.02-2.0 AGU/g DS, such as 0.1-1.0 AGU/g DS, or such as 0.2 AGU/g DS.

Additional enzyme variants are also contemplated for inclusion in the composition. Two or more α-amylase variants can be used alone or in combination with other enzymes discussed herein. For example, a third enzyme may be another α-amylase (e.g. a yeast α-amylase) or another α-amylase variant. These can be *Bacillus* α-amylases or non-Bacillus α-amylases.

Another enzyme that can optionally be added is a debranching enzyme, such as an isoamylase (EC 3.2.1.68) or a pullulanases (EC 3.2.1.41). Isoamylase hydrolyses α-1,6-D-glucosidic branch linkages in amylopectin and β-limit dextrins and can be distinguished from pullulanases by the inability of isoamylase to attack pullulan, and by the limited action on α-limit dextrins. Debranching enzymes may be added in effective amounts well known to the person skilled in the art.

The exact composition of the products of the process depends on the combination of enzymes applied as well as the type of granular starch processed. The soluble hydrolysate can be maltose with a purity of at least about 85%, at least about 90%, at least about 95.0%, at least about 95.5%, at least about 96.0%, at least about 96.5%, at least about 97.0%, at least about 97.5%, at least about 98.0%, at least about 98.5, at least about 99.0% or at least about 99.5%. The soluble starch hydrolysate can also be glucose or the starch hydrolysate has a DX (glucose percent of total solubilized dry solids) of at least 94.5%, at least 95.0%, at least 95.5%, at least 96.0%, at least 96.5%, at least 97.0%, at least 97.5%, at least 98.0%, at least 98.5, at least 99.0% or at least 99.5%. Equally contemplated, however, is the process wherein the product is a specialty syrup, such as a specialty syrup containing a mixture of glucose, maltose, DP3 and DPn for use in the manufacture of ice creams, cakes, candies, canned fruit.

Two milling processes contemplated include: wet and dry milling. In dry milling, the whole kernel is milled and used. Wet milling gives a good separation of germ and meal (starch granules and protein), and is with a few exceptions, applied at locations where the starch hydrolysate is used in production of syrups. Both dry and wet milling are well known in the art of starch processing and are equally contemplated for use with the compositions and methods disclosed. The process may be conducted in an ultrafiltration system where the retentate is held under recirculation in presence of enzymes, raw starch and water and where the permeate is the soluble starch hydrolysate. Equally contemplated is the process conducted in a continuous membrane reactor with ultrafiltration membranes and where the retentate is held under recirculation in presence of enzymes, raw starch and water, and where the permeate is the soluble starch hydrolysate. Also contemplated is the process conducted in a continuous membrane reactor with microfiltration membranes and where the retentate is held under recirculation in presence of enzymes, raw starch and water, and where the permeate is the soluble starch hydrolysate.

In one regard, the soluble starch hydrolysate of the process is subjected to conversion into high fructose starch-based syrup (HFSS), such as high fructose corn syrup (HFCS). This conversion can be achieved using a glucose isomerase, and such as the enzyme immobilized to a solid support. Contemplated isomerases included the commercial products Sweetzyme®, IT (Novozymes A/S); G-zyme® IMGI, and G-zyme® G993, Ketomax®, G-zyme® G993, G-zyme® G993 liquid, and GenSweet® IGI.

In another aspect, the soluble starch hydrolysate of produced yields production of fuel or potable ethanol. In the process of the third aspect the fermentation may be carried out simultaneously or separately/sequential to the hydrolysis of the granular starch slurry. When the fermentation is performed simultaneous to the hydrolysis, the temperature can be between 30° C. and 35° C., or between 31° C. and 34° C. The process may be conducted in an ultrafiltration system where the retentate is held under recirculation in presence of enzymes, raw starch, yeast, yeast nutrients and water and where the permeate is an ethanol containing liquid. Equally contemplated is the process conducted in a continuous membrane reactor with ultrafiltration membranes and where the retentate is held under recirculation in presence of enzymes, raw starch, yeast, yeast nutrients and water and where the permeate is an ethanol containing liquid.

The soluble starch hydrolysate of the process may also be used for production of a fermentation product comprising fermenting the treated starch into a fermentation product, such as citric acid, monosodium glutamate, gluconic acid, sodium gluconate, calcium gluconate, potassium gluconate, glucono delta lactone, or sodium erythorbate.

The amylolytic activity of the α-amylase variant may be determined using potato starch as substrate. This method is based on the break-down of modified potato starch by the enzyme, and the reaction is followed by mixing samples of the starch/enzyme solution with an iodine solution. Initially, a blackish-blue color is formed, but during the break-down of the starch the blue color gets weaker and gradually turns into a reddish-brown, which is compared to a colored glass standard.

5.7 Biofilm Removal Compositions and Use

The composition may comprise one α-amylase variants as the major enzymatic component, e.g., a mono-component composition for use in removing biofilms. Alternatively, the composition may comprise multiple enzymatic activities, such as multiple amylases, or a cocktail of enzymes including an aminopeptidase, amylase (β- or α- or gluco-amylase), carbohydrase, carboxypeptidase, catalase, cellulase, chitinase, cutinase, cyclodextrin glycosyltransferase, deoxyribonuclease, esterase, alpha-galactosidase, β-galactosidase, glucoamylase, α-glucosidase, β-glucosidase, haloperoxidase, invertase, laccase, lipase, mannosidase, oxidase, pectinolytic enzyme, peptidoglutaminase, peroxidase, phytase, polyphenoloxidase, proteolytic enzyme, ribonuclease, transglutaminase, and/or xylanase, or any combination thereof for removing biofilms. The additional enzyme(s) may be producible by means of a microorganism belonging to the genus *Aspergillus*, such as *Aspergillus aculeatus*, *Aspergillus awamori*, *Aspergillus niger*, or *Aspergillus oryzae*; or *Trichoderma*; *Humicola*, such as *Humicola insolens*; or *Fusarium*, such as *Fusarium bactridioides, Fusarium cerealis, Fusarium crookwellense, Fusarium culmorum, Fusarium graminearum,*

*Fusarium graminum, Fusarium heterosporum, Fusarium negundi, Fusarium oxysporum, Fusarium reticulatum, Fusarium roseum, Fusarium sambucinum, Fusarium sarcochroum, Fusarium sulphureum, Fusarium toruloseum, Fusarium trichothecioides,* or *Fusarium venenatum.*

The α-amylase variant comprising compositions may be prepared in accordance with methods known in the art and may be in the form of a liquid or a dry composition. For instance, the α-amylase variant containing composition may be in the form of a granulate or a microgranulate. The polypeptide to be included in the composition may be stabilized in accordance with methods known in the art.

Examples are given below of uses of the polypeptide compositions. The dosage of the α-amylase variant containing composition and other conditions under which the composition is used may be determined on the basis of methods known in the art.

The α-amylase variants are further contemplated for use in a composition along with a 2,6-β-D-fructan hydrolase or variant thereof.

One process is disintegration and/or removal of biofilm. The term "disintegration" as used herein is to be understood as hydrolysis of polysaccharides in a biofilm matrix connecting and binding together individual microbial cells in the biofilm, whereby the microbial cells can be released and removed from the biofilm. The biofilm is present at a surface, and the disintegration of the biofilm is achieved by bringing the surface in contact, e.g. by immersing, covering or splashing the surface with an aqueous medium comprising an α-amylase variant or one or more other enzymes responsible for breaking down biofilms, such as but not limited to 2,6-β-D-fructan hydrolase. The composition can be used to hydrolyse slime, e.g. in white waters in the pulping and paper industry.

The α-amylase variant may be present in the amount of 0.0001 to 10,000 mg/L, or 0.001-1000 mg/L, or 0.01-100 mg/L, or even 0.1-10 mg/L. Additional enzymes and enzyme variants may be present in similar amounts or less, dependent on the use and solubility of the enzyme in the final solution.

The process may suitably be performed at temperatures from about ambient temperature to about 70° C. An exemplary temperature range is from about 30° C. to about 60° C., e.g., about 40° C. to about 50° C.

A suitable pH for the hydrolyzing biofilms lies within from about 3.5 to about 8.5. An exemplary range includes from about 5.5 to about 8 pH, e.g. from about 6.5 to about 7.5. The contact time or reaction time for the enzyme variant to effectively removing a biofilm may vary considerably, depending on the biofilm properties and the frequency of which a surface is treated with the enzyme variant alone or in combination with other enzymes, such as 2,6-β-D-fructan hydrolase. For example, a suitable reaction time lies within about 0.25 to about 25 hours, such as from about 1 to about 10 hours, e.g. about 2 hours.

Additional enzymes that can be combined with the α-amylase variants and 2,6-β-D-fructan hydrolases include but are not limited to cellulases, hemicellulases, xylanases, other amylases including other α-amylases, lipases, proteases, and/or pectinases.

The enzymes can further be combined with antimicrobial agents such as enzymatic or non-enzymatic biocides. An enzymatic biocide may e.g. be a composition comprising an oxidoreductase, e.g. a laccase or a peroxidase, especially haloperoxidase, and optionally an enhancing agent, such as an alkyl syringate, as described for example in patent applications WO 97/42825 and DK 97/1273.

The surface from which a biofilm is to be removed and/or cleaned off can be a hard surface, which by definition relates to any surface which is essentially non-permeable to microorganisms. Examples of surfaces are surfaces made from metal, e.g. stainless steel alloys, plastics/synthetic polymers, rubber, board, glass, wood, paper, textile, concrete, rock, marble, gypsum and ceramic materials which optionally may be coated, e.g. with paint, enamel, polymers and the like. Accordingly, the surface may be a member of a system holding, transporting, processing, or in contact with aqueous solutions such as water supply systems, food processing systems, cooling systems, chemical processing systems or pharmaceutical processing systems. The compositions and methods of using the compositions for removing biofilm in the wood processing industry, such as the pulp and/or paper industry. Accordingly, the enzyme variants and compositions containing the enzyme variants are useful in a conventional cleaning-in-place (C-I-P) system. The surface may a member of a system unit such as pipes, tanks, pumps, membranes, filters, heat exchangers, centrifuges, evaporators, mixers, spray towers, valves and reactors. The surface may also be or be a part of utensils used in the medical science and industry such as contaminated endoscopes, prosthetic devices or medical implants.

The compositions for biofilm removal is also contemplated for preventing so-called bio-corrosion occurring when a metal surface, e.g. a pipeline, is attacked by a microbial biofilm, that is by disintegrating the biofilm thereby preventing the microbial cells of the biofilm from creating a biofilm environment, which corrodes the metal surface to which it is attached.

Another application for anti-biofilm compositions is for oral care. The surface may however also be of biological origin, such as mucous membranes, skin, teeth, hair, nails etc.

Teeth with dental plaque, e.g. by incorporating the enzyme variants into toothpaste, and contaminated contact lenses are encompassed as surfaces. Accordingly, the variant enzymes can be used for compositions and processes for making a medicament comprising an enzyme variant for disintegration of plaque present on a human or animal tooth. A further use is disintegration of biofilm from mucous membranes, such as biofilm in lungs in patients suffering from cystic fibrosis.

Accordingly in a still further aspect relates to an oral care composition comprising a recombinant enzyme variant, purified and essentially free of any active contaminants. An oral care composition may suitably comprise an amount of a recombinant enzyme variant.

Other enzymes for use in oral care compositions include but are not limited to 2,6-β-D-fructan hydrolase activity in the oral care composition. Contemplated enzyme activities include activities from the group of enzymes comprising dextranase; mutanases; oxidases, such as glucose oxidase, L-amino acid oxidase, peroxidases, such as e.g. the *Coprinus* sp. peroxidases described in WO 95/10602 (from Novo Nordisk A/S) or lactoperoxidase, haloperoxidases, especially haloperoxidase derivable from *Curvularia* sp., in particular *C. verruculosa* and *C. inaequalis*; laccases; proteases such as papain, acidic protease (e.g. the acidic proteases described in WO 95/02044 (Novo Nordisk A/S)), endoglucosidases, lipases, amylases, including amyloglucosidases, such as AMG (from Novo Nordisk A/S); anti-microbial enzymes, and mixtures thereof.

The oral care composition may have any suitable physical form (i.e. powder, paste, gel, liquid, ointment, tablet etc.). An "oral care composition" includes a composition, which can be used for maintaining or improving the oral hygiene in the mouth of humans and animals, by preventing dental caries, preventing the formation of dental plaque and tartar, removing dental plaque and tartar, preventing and/or treating dental diseases etc. At least in the context oral care compositions do also encompass products for cleaning dentures, artificial teeth and the like. Examples of such oral care compositions includes toothpaste, dental cream, gel or tooth powder, odontic mouth washes, pre- or post brushing rinse formulations, chewing gum, lozenges, and candy. Toothpastes and tooth gels typically include abrasive polishing materials, foaming agents, flavoring agents, humectants, binders, thickeners, sweetening agents, whitening/bleaching/stain removing agents, water, and optionally enzymes.

Mouthwashes, including plaque-removing liquids, typically comprise a water/alcohol solution, flavor, humectant, sweetener, foaming agent, colorant, and optionally enzymes.

Abrasive polishing material might also be incorporated into the oral care composition such as a dentifrice.

Accordingly, abrasive polishing material can include alumina and hydrates thereof, such as alpha alumina trihydrate; magnesium trisilicate; magnesium carbonate; kaolin; aluminosilicates, such as calcined aluminum silicate and aluminum silicate; calcium carbonate; zirconium silicate; and also powdered plastics, such as polyvinyl chloride; polyamides; polymethyl methacrylate; polystyrene; phenol-formaldehyde resins; melamine-formaldehyde resins; urea-formaldehyde resins; epoxy resins; powdered polyethylene; silica xerogels; hydrogels and aerogels and the like. Also suitable as abrasive agents are calcium pyrophosphate; water-insoluble alkali metaphosphates; dicalcium phosphate and/or its dihydrate, dicalcium orthophosphate; tricalcium phosphate; particulate hydroxyapatite and the like. It is also possible to employ mixtures of these substances.

Dependent on the oral care composition, the abrasive product may be present in from about 0% to about 70% by weight, e.g., from about 1% to about 70%. For toothpastes, the abrasive material content typically lies in the range of from 10% to 70% by weight of the final toothpaste.

Humectants are employed to prevent loss of water from e.g. tooth pastes. Suitable humectants for use in oral care compositions include the following compounds and mixtures thereof: glycerol; polyol; sorbitol; polyethylene glycols (PEG); propylene glycol; 1,3-propanediol; 1,4-butanediol; hydrogenated partially hydrolyzed polysaccharides and the like. Humectants are in general present in from 0% to about 80%, e.g., about 5% to about 70% by weight, in toothpaste.

Silica, starch, tragacanth gum, xanthan gum, extracts of Irish moss, alginates, pectin, cellulose derivatives, such as hydroxyethyl cellulose, sodium carboxymethyl cellulose and hydroxypropyl cellulose, polyacrylic acid and its salts, polyvinylpyrrolidone, can be mentioned as examples of suitable thickeners and binders, which helps stabilizing a dentifrice product. Thickeners may be present in toothpaste creams and gels in an amount of from about 0.1% to about 20% by weight, and binders to the extent of from about 0.01 to about 10% by weight of the final product.

As foaming agent soap, anionic, cationic, non-ionic, amphoteric and/or zwitterionic surfactants can be used. These may be present at levels of from 0% to about 15%, or from about 0.1 to about 13%, or from about 0.25% to about 10% by weight of the final product.

Surfactants are only suitable to the extent that they do not exert an inactivation effect on the present enzymes. Surfactants include fatty alcohol sulfates, salts of sulfonated monoglycerides or fatty acids having 10 to 20 carbon atoms, fatty acid-albumen condensation products, salts of fatty acids amides and taurines and/or salts of fatty acid esters of isethionic acid.

Suitable sweeteners include saccharin for use in a formulation.

Flavors, such as spearmint, are usually present in low amounts, such as from about 0.01% to about 5% by weight, especially from about 0.1% to about 5%.

Whitening/bleaching agents include $H_2O_2$ and may be added in amounts less that about 5%, or from about 0.25% to about 4%, calculated by the weight of the final product.

The whitening/bleaching agents may be an enzyme, such as an oxidoreductase. Examples of suitable teeth bleaching enzymes, such as those described in WO 97/06775 (from Novo Nordisk A/S).

Water is usually added in an amount giving e.g. toothpaste a flowable form.

Further water-soluble anti-bacterial agents, such as chlorohexidine digluconate, hexetidine, alexidine, Triclosan®, quaternary ammonium anti-bacterial compounds and water-soluble sources of certain metal ions such as zinc, copper, silver and stannous (e.g., zinc, copper and stannous chloride, and silver nitrate) may also be included.

Also contemplated is the addition of compounds which can be used as fluoride source, dyes/colorants, preservatives, vitamins, pH-adjusting agents, anti-caries agents, desensitizing agents etc.

Other components useful in oral care compositions are enzymes as described above. Enzymes are biological catalysts of chemical reactions in living systems. Enzymes combine with the substrates on which they act forming an intermediate enzyme-substrate complex. This complex then is converted to a reaction product, and a liberated enzyme that continues its specific enzymatic function.

Enzymes provide several benefits when used for cleansing of the oral cavity. Proteases break down salivary proteins, which are adsorbed onto the tooth surface and form the pellicle, the first layer of resulting plaque. Proteases along with lipases destroy bacteria by lysing proteins and lipids which form the structural components of bacterial cell walls and membranes.

Dextranase and other carbohydrases such as the 2,6-β-D-fructan hydrolase breaks down the organic skeletal structure produced by bacteria that forms a matrix for bacterial adhesion. Proteases and amylases, not only prevents plaque formation, but also prevents the development of calculus by breaking-up the carbohydrate-protein complex that binds calcium, preventing mineralization.

A toothpaste may typically comprise the following ingredients (in weight % of the final toothpaste composition): abrasive material to about 70%; humectant: 0% to about 80%; thickener: about 0.1% to about 20%; binder: about 0.01% to about 10%; sweetener: about 0.1% to about 5%; foaming agent: 0% to about 15%; whitener: 0% to about 5%; and enzymes: about 0.0001% to about 20%.

In a specific embodiment, a toothpaste has a pH in the range from about 6.0 to about 8.0, and comprises: a) about 10% to about 70% abrasive material; b) 0% to about 80% humectant; c) 0.1% to about 20% thickener; d) 0.01% to about 10% binder; e) about 0.1% to about 5% sweetener; 0% to about 15% foaming agent; g) 0% to about 5% whitener; i) about 0.0001% to about 20% enzymes.

Said enzymes referred to under i) include α-amylase variants alone or in combination with other enzymes, such as 2,6-β-D-fructan hydrolase, and optionally other types of enzymes mentioned above known to be used in toothpastes and the like.

A mouth wash may typically comprise the following ingredients (in weight % of the final mouth wash composition): 0% to about 20% humectant; 0% to about 2% surfactant; 0% to about 5% enzymes; 0% to about 20% ethanol; 0% to about 2% other ingredients (e.g., flavor, sweetener active ingredients such as fluorides). The composition can also contain from about 0% to about 70% water.

The mouth wash composition may be buffered with an appropriate buffer e.g. sodium citrate or phosphate in the pH-range of about 6.0 to about 7.5.

The mouth wash may be in none-diluted form (i.e. must be diluted before use).

The oral care compositions may be produced using any conventional method known to the art of oral care.

It will be apparent to those skilled in the art that various modifications and variation can be made to the compositions and methods of using same without departing from the spirit or scope of the intended use. Thus, it is the modifications and variations provided they come within the scope of the appended claims and their equivalents.

EXAMPLES

Example 1

B. licheniformis α-Amylase A1T Variant of Spezyme® FRED

FRED from B. licheniformis strain BML 612 is Δamy gene, amplifiable FRED gene at cat locus with cat$^R$ marker, and Δ spo II AC.

To express Spezyme® FRED α-amylase from expression plasmid pHPLT (see e.g., Published U.S. Application No. 2006/0014265 and International PCT Application No. WO 2005/111203), the Spezyme® FRED α-amylase gene was amplified by PCR (Polymerase Chain Reaction) with the primers LAT(PstI)_FW & LAT(HpapI_RV:

```
LAT(PSTI)_FW
                                    (SEQ ID NO: 3)
5'-GAATGTCTGCAGCTTCAGCAGCAAATCTTAATGGGACGCTGATGCA

G-3'

LAT(HPAI)_RV
                                    (SEQ ID NO: 4)
5'-CCCGGGGTTAACTCATCTTTGAACATAAATTGAAACCGACCCGCC

G-3'
```

PCR was performed on a thermocycler with High Fidelity Platinum Taq polymerase (Invitrogen, Carlsbad, Calif. USA) according to the instructions of the manufacturer (annealing temperature of 55° C.). The resulting PCR fragment was digested with the restriction enzymes PstI and HpaI and ligated with T4 DNA ligase into PstI and HpaI digested pHPLT according to the instructions of the supplier (Invitrogen, Carlsbad, Calif. USA). The ligation mixture was transformed into B. subtilis strain SC6.1 as described in U.S. Published Patent Application US2002/0182734 (see also, International Publication WO 02/14490). All three clones produced relatively large halos, which is indicative for high amylase expression. The inserts of three clones were sequenced by DNA sequencing. One of the clones contained a single mutation in the FRED gene, probably due to an error in the LAT(PSTI)_FW primer, and expresses FRED(A 1 T) amylase. In this clone, the first codon of Spezyme® FRED α-amylase (mature chain absent the signal sequence), encoding an alanine (gca), was mutated into another codon (aca) encoding a threonine.

The FRED(A1T) gene was then cloned into the pICatH vector (see e.g., Published U.S. Application No. 2006/0014265 and International PCT Application No. WO 2005/111203). The FRED(A1T) gene was amplified by PCR as described above but using the primers EBS2XhoI_FW and EBS2XhoI_RV:

```
EBS2XHOI_FW
                                    (SEQ ID NO: 5)
5'-ATCCTACTCGAGGCTTTTCTTTTGGAAGAAAATATAGGG-3'

EBS2XHOI_RV
                                    (SEQ ID NO: 6)
5'-TGGAATCTCGAGGTTTTATCCTTTACCTTGTCTCC-3'
```

Figure 2A:
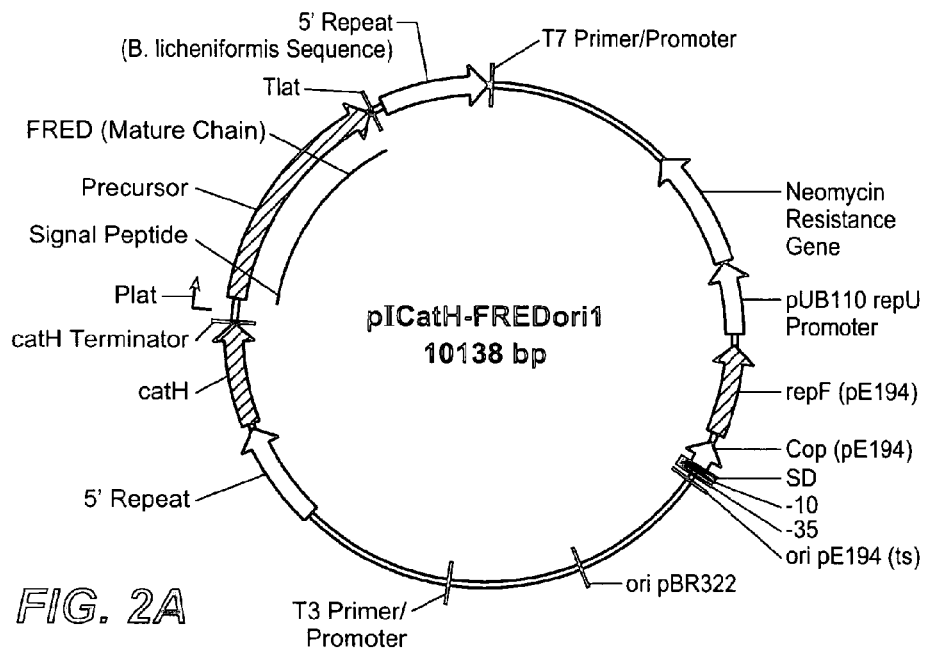
FIG. 2A is a schematic of pICatH-FREDoril.
Figure 2B:
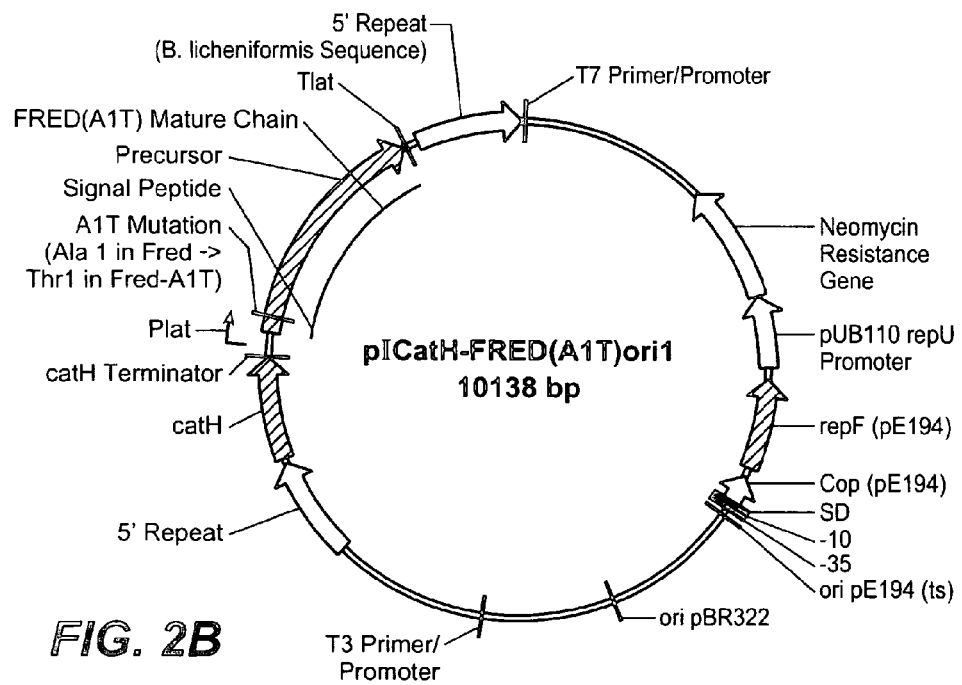
FIG. 2B is a schematic of pICatH-FRED(A 1 T)ori1.

The resulting PCR fragment was digested with restriction enzyme, XhoI, and ligated with T4 DNA ligase into XhoI digested pICatH according to the instructions of the supplier (Invitrogen, Carlsbad, Calif. USA). The ligation mixture was transformed into B. subtilis strain SC6.1 as described above. A clone was selected in which the orientation of the FRED (A1T) gene is the same as the flanking catH gene (FIG. 2B). This resulted in the strain SC6.1(pICatH-FRED(A1T)ori1) and its sequence was confirmed by DNA sequencing.

The 'wild-type' Spezyme® FRED α-amylase gene (encoding FRED amylase without the A1T mutation) was also cloned into the pICatH vector. The FRED gene was amplified by PCR (Polymerase Chain Reaction) from the Spezyme® FRED α-amylase with the primers PlatFREDXhoI_FW and FRED-Tlat_RV:

```
PlatFREDXhoI_FW
                                    (SEQ ID NO: 7)
5'-ACCCCCCTCGAGGCTTTTCTTTTGGAAGAAAATATAGGGAAAATGGT

ACTTGTTAAAAATTCGGAATATTTATACAATATCATATGTTTCACATTGA

AAGGGGAGGAGAATCATGAAACAACAAAAACGGC-3'

FRED-Tlat_RV
                                    (SEQ ID NO: 8)
5'-GTCGACCTCGAGGTTTTATCCTTTACCTTGTCTCCAAGCTTAAAATA

AAAAAACGGATTTCCTTCAGGAAATCCGTCCTCTGTTAACTCATCTTTGA

ACATAAATTG-3'
```

PCR was performed on a thermocycler with Phusion High Fidelity DNA polymerase (Finnzymes O Y, Espoo, Finland) according to the instructions of the manufacturer (annealing temperature of 55° C.). The resulting PCR fragment was digested with restriction enzyme, XhoI, and ligated with T4 DNA ligase into XhoI digested pICatH as described above. The ligation mixture was transformed into B. subtilis strain SC6.1 as described above. A clone was selected in which the orientation of the FRED gene is the same as the flanking catH gene (FIG. 2A). The clone's sequence was confirmed by DNA sequencing. This clone was designated SC6.1(pICatH-FREDori1).

Figure 3:
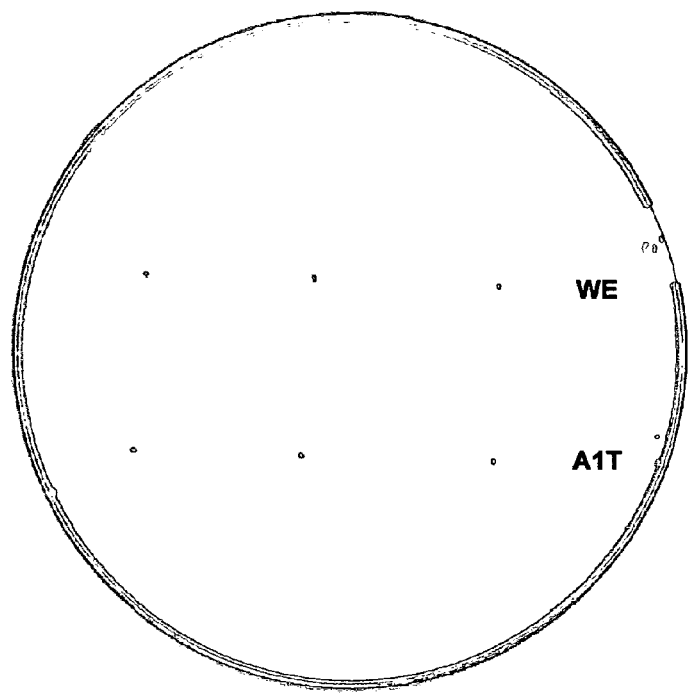
FIG. 3 shows the result of an HI agar test of *B. subtilis* strains expressing the A1T α-amylase variant (bottom) versus strains expressing FRED (Spezyme® FRED) α-amylase in the digestion of amylose. Amylose digestion appears enhanced in the A1T variant.

B. subtilis SC6.1(pICatH-FRED(A1T)ori1) and SC6.1(pI-CatH-FRED(A1T)ori1) were pricked in triplicate from a Heart Infusion (HI) agar plate on a new HI plate containing 0.2% soluble starch. After 16 h growth at 37° C., the plate was stained with an iodine solution to visualize the clearing of starch in the plate (FIG. 3). The size of the halo around the colony (i.e., the cleared starch) is a measure for amylase production since the specific activity of the FRED(1AT) molecule is not altered with respect to the wild-type FRED molecule. The halos formed by the B. subtilis strain expressing FRED(A1T) (at the bottom, marked A1T) are larger than that of the same host strain expressing wild-type FRED amylase (at the top, marked wt). Thus, the production of FRED amylase by *B. subtilis* is increased by the introduction of the A1T mutation in the FRED molecule.

Example 2

Expression of FRED(A1T) Variant in *Bacillus licheniformis*

The plasmids, pICatH-FREDori1 and pICatH-FRED (A1T)ori1, were transformed into *B. licheniformis* strain BML612 (see International PCT Application No. WO 2005/111203) at the permissive temperature, 37° C. For each construct, one neomycin resistant (neoR) and one chloramphenicol resistant (CmR) transformant was selected and designated BML612(pICatH-FREDori1) and BML612(pICatH-FRED (A1T)ori1), respectively. The plasmids in BML612(pICatH-FREDori1) and BML612(pICatH-FRED(A1T)ori1) were integrated into the catH region on the *B. licheniformis* genome by growing the strains at a non-permissive temperature (50° C.) in medium with 5 µg/mL chloramphenicol. For each construct, one CmR resistant clone was selected and designated BML612-pICatH-FREDori1 and BML612-pICatH-FRED(A 1 T)ori 1, respectively.

Both strains were grown again at the permissive temperature for several generations without neomycin to loop-out vector sequences and then for each construct, one neomycin sensitive (neoS) but CmR clone was selected. In these clones, vector sequences of pICatH on the chromosome were excised (including the neomycin resistance gene) and only the catH-amylase cassette was left. Next, the catH-amylase cassette on the chromosome was amplified by growing the strain in media with increasing concentrations of chloramphenicol. After various rounds of amplification, for each construct one clone (resistant against 75 µg/mL chloramphenicol) was selected which produced the largest halo on a starch plate. These strains were then designated BML612-FRED and BML612-FRED(A1T), respectively. Both strains were put through a typical *B. licheniformis* fermentation process at both 14L and 3000L scales. At both scales the FRED(A1T) fermentations showed both an increased initial enzyme production rate and a higher final titer. The graph in FIG. 3 shows the results of three 3000L pilot fermentations comparing a typical production curve for the BML612-FRED strain and two curves for the BML612-FRED(A1T) strain. The graph shows a significant increase in final enzyme titer over the Spezyme® FRED α-amylase expressing strain. The growth medium used consisted of corn steep solids and soy flour as sources of organic compounds along with inorganic salts as a source of sodium, potassium, phosphate, magnesium, sulfate and other trace elements. A carbohydrate source, such as glucose, was also included as part of the starting medium. Once the culture was established and begins growing, the carbohydrate is metered into the tank to maintain the culture. Periodic sampling of the culture medium in the fermenter was measured at regular intervals to assess enzyme titer using a colorimetric assay method. The fermentation ended when the enzyme production rate stopped increasing.

The variant protein was characterized as having the following specific activity. Two FRED A1T purified materials and four other FRED A1T samples were analyzed to determine the specific activity of FRED A1T. FRED A1T was also analyzed and was used as a protein standard. SDS-PAGE gels, TCA and total proteins via nitrogen analysis, and densitometry were performed. The following samples were tested:

FRED A1T
1) #1 purified material
2) #2 purified material
3) 20060100-14L PA run, "normal" run, clarified process
4)
5) 20068013, clarified-$1^{st}$ 3K PA run, clarified process
6) 20068013, whole cell-$1^{st}$ 3K PA run, whole broth
7) 20068024, clarified-$2^{nd}$ 3K PA run, clarified process
8) 20068024, whole cell-$2^{nd}$ 3K PA run, whole broth FRED
1) 105-01086-002 FRED gel reference
2) 107-04326-001 FRED-L run 1
3) 101-05330-001 FRED-L run 2

The specific activity for FRED A1T was determined as 1317 LU/mg active protein. This result was based on the Activity/Adjusted TCA protein and one gel with only one FRED A1T sample, which was used as a protein standard. Based on more recent work, the FRED A1T sample was actually overloaded on this gel making the FRED A1T results falsely high.

Several different gels using at least three FRED A1T samples were used as standards and controls. Bovine serum albumin (BSA) and LAT were also used as protein standards on some of the gels. The specific activity was calculated using two different methods: using the Activity/Adjusted TCA protein and using Spezyme® FRED, LAT and/or BSA as protein standards.

The results using the Activity/Adjusted TCA protein differ from the results using a protein standard. Since the results against the standard are closer to what was expected for both the Spezyme® FRED (FRED) and FRED A1T samples, the Activity/Adj. Trichloroacetic acid (TCA) precipitated protein results were not included in the final specific activity determination. Based on these experiments, FRED A1T has a specific activity of 1323 LU/mg active protein or 0.00076 mg/LU, which is about 2% higher than the historically assigned value of 1317 LU/mg active protein or 0.00076 mg/LU.

Example 3

Methods of Enhancing Fermentation and Purification of FRED A1T

The samples obtained in Example 1 were then run on an SDS polyacrylamide gel. For the SDS polyacrylamide gel, the Spezyme® FRED and FRED A1T samples were loaded based on active protein values. The active protein was calculated using a Spezyme® FRED conversion of 0.00076 mg active protein/LU. The samples were prepped using trichloroacetic acid (TCA) inactivation. The gel was stained using conventional Coomassie. When loading all samples using the Spezyme® FRED specific activity value, both the Spezyme® FRED and FRED A1T showed similar main band intensities, indicating that the active protein/specific activities are very similar between the variant and parental strain.

The specific activity was calculated using 2 different methods. First, the active protein was determined by multiplying the TCA precipitated protein with the purity of the protein (active band versus total Coomassie area response) from the gel.

In the second method, three FRED A1T lots as well as LAT and bovine serum albumin (BSA), were assigned using its active protein value, and were used as a standard against which all the other samples were compared and specific activity values were determined; this was performed using the raw area of the main protein band for each sample.

TABLE 1

Specific Activity (Activity/Adj. TCA Protein) using Adjusted TCA Values

| Sample Type | Activity (LU/ml) | Total Protein (mg/ml) | TCA Protein (mg/ml) | TCA/Total Protein (%) | % Purity | Activity/Adj. TCA protein (LU/mg) |
|---|---|---|---|---|---|---|
| FRED-gel ref | 22527 | 33.57 | 18.31 | 54.5 | 95.9 | 1283 |
| FRED-L-Run 1 | 18245 | 55.21 | 14.87 | 26.9 | 94.6 | 1297 |
| FRED-L-Run 2 | 19172 | 48.83 | 14.81 | 30.3 | 94.8 | 1366 |
|  |  |  |  |  |  | 1315 |
| FRED A1T pure | 9990 | 5.84 | 5.95 | 101.8 | 89.6 | 1875 |
| FRED A1T pure | 16708 | 8.35 | 8.49 | 101.7 | 96.5 | 2039 |
| FRED A1T | 21045 | 17.78 | 12.22 | 68.7 | 94.4 | 1826 |
| FRED A1T Clarified | 24530 | 24.34 | 15.60 | 64.1 | 95.5 | 1645 |
| FRED A1T Whole Broth | 19581 | 42.75 | 13.84 | 32.4 | 98.4 | 1438 |
| FRED A1T Clarified | 20353 | 28.35 | 17.94 | 63.3 | 93.3 | 1216 |
| FRED A1T Whole broth | 22760 | 66.02 | 17.43 | 26.4 | 96.4 | 1354 |
|  |  |  |  | FRED A1T AVG |  | 1655 |

Note:
The proteins were calculated using a conversion factor of 5.78 g protein/g nitrogen for the Spezyme ® FRED. A conversion factor of 5.79 g protein/g nitrogen was used for the FRED A1T. By "FRED A1T pure" is meant a purified enzyme as described in the example above. By "whole broth" is meant unclarified.

Using the Activity/Adj. TCA protein calculation gives an average specific activity of 1315 LU/mg for three runs. The FRED A1T samples range from 1216 to 2039 LU/mg, with an average of 1655 LU/mg. The A1T runs had many differences in the fermentation and recovery process that may be contributing to the variability in these results.

TABLE 2

Specific Activity using Spezyme ® FRED ("FRED"), LAT and BSA as Protein Standards

| Sample Type | AVG Specific Activity (LU/mg) * |
|---|---|
| FRED-gel ref | 1203 |
| FRED-L | 1354 |
| FRED-L | 1412 |
|  | 1323 |
| FRED A1T pure | 1430 |
| FRED A1T pure | 1403 |
| FRED A1T | 1428 |
| FRED A1T | 1299 |
| FRED A1T Clarified | 1331 |
| FRED A1T Whole Broth | 1307 |
| FRED A1T Clarified | 1126 |
| FRED A1T Whole Broth | 1213 |
| FRED A1T AVG | 1317 |

By "*" is meant the specific activity is the average obtained from four gels using 3 different analyses and 5 different protein standards (3 Spezyme ® FRED standards as well as BSA and LAT standards). The specific activity against the different protein standards gave the FRED result of 1323 LU/mg, which is similar to the assigned value of 1299 LU/mg. The FRED A1T had a specific activity result of 1317 LU/mg.

Example 4

B. subtilis Production of FRED(A1T)

B. subtilis was used as an intermediate host to build the integration plasmids for A1T and wild-type Spezyme® FRED. The result was that the B. subtilis FRED(A1T) polypeptide has an increased amount of protein produced over that of the wild-type Spezyme® FRED.

The Spezyme® FRED amylase gene (encoding Spezyme® FRED α-amylase with an alanine at position one, $X_2$) and mutant FRED(A1T) gene (encoding a FRED mutant with a threonine instead of the alanine at $X_2$) were cloned in the pICatH vector (U.S. Publication No. 20060014265) and transformed into B. subtilis strain SC6.1 (Australian Application No. 20041293826). For both the Spezyme® FRED and FRED A1T constructs, a clone was selected in which the origination of the Spezyme® FRED gene was the same as the flanking catH gene (FIGS. 2A and 2B). This produced strains SC6.1(pICatH-FREDori1) and SC6.1(pICatH-FRED(A1T) ori1). Both strains were pricked in triplicate from a Heart Infusion (HI) agar plate on a new HI plate containing 0.2% soluble starch. After 16 hours growth at 37° C., the plate was stained with an iodine solution to visualize the clearing of starch in the plate. The size of the halo around the colony (cleared starch) is a measure of α-amylase production (the specific activity of the FRED(1AT) molecule is not altered with respect to the wild-type Spezyme® FRED. FIG. 3 shows that the halos formed by the B. subtilis strain expressing FRED (A1T) (at the bottom, marked "A1T") are larger than that of the same strain expressing wild-type Spezyme® FRED (at the top marked "wt").

From this data, it was determined that the production of Spezyme® FRED α-amylase by B. subtilis is increased by introducing the A1T mutation in the Spezyme® FRED molecule.

Example 5

Modification of LAT α-Amylase

Another α-amylase contemplated is the mature LAT α-amylase. The mature form can be produced as a heterologous protein fused with signal polypeptide that is not the same as that of LAT or derived from the same parent. It would involve substituting any amino acid other than alanine or valine at the first residue. Another modification would be to substitute the first residue (the underlined alanine) with two, three, four, or five residues for that alanine, wherein the first of those residues are an amino acid other than alanine or valine. Yet another example would be the substitution of a threonine for the underlined alanine. The polypeptide could then be synthesized as described herein or known in the art.

```
                                              (SEQ ID NO: 9)
ANLNGTLMQY FEWYMPNDGQ HWKRLQNDSA YLAEHGITAV
WIPPAYKGTS QADVGYGAYD LYDLGEFHQK GTVRTKYGTK
GELQSAIKSL HSRDINVYGD VVINHKGGAD ATEDVTAVEV
DPADRNRVIS GEHLIKAWTH FHFPGRGSTY SDFKWHWYHF
DGTDWDESRK LNRIYKFQGK AWDWEVSNEN GNYDYLMYAD
IDYDHPDVAA EIKRWGTWYA NELQLDGFRL DAVKHIKFSF
LRDWVNHVRE KTGKEMFTVA EYWQNDLGAL ENYLNKTNFN
HSVFDVPLHY QFHAASTQGG GYDMRKLLNG TVVSKHPLKS
VTFVDNHDTQ PGQSLESTVQ TWFKPLAYAF ILTRESGYPQ
VFYGDMYGTK GDSQREIPAL KHKIEPILKA RKQYAYGAQH
DYFDHHDIVG WTREGDSSVA NSGLAALITD GPGGAKRMYV
GRQNAGETWH DITGNRSEPV VINSEGWGEF HVNGGSVSIY
VQR
```

Example 6

Modification of Spezyme® FRED

One α-amylase contemplated is the mature Spezyme® FRED. The mature form can be produced as a heterologous protein fused with signal polypeptide that is not the same as that of LAT or derived from the *Bacillus* species. It would involve substituting the first residue (i.e., alanine) with any amino acid other than alanine or valine. Another modification would be to substitute two, three, four, or five residues for that alanine, wherein the first of those residues are an amino acid other than alanine or valine. Yet another example would be the substitution of a threonine for the underlined alanine, i.e. A1T also known as FRED A1T. The polypeptide could then be synthesized as described herein or known in the art.

The Spezyme® FRED has the following mutations compared to the LAT mature polypeptide sequence: M15T, H133Y, N188S, and A209V, the residues are underlined in the sequence below. The lysine at residue 23 can also be an arginine.

```
                                                           (SEQ ID NO: 10)
ANLNGTLMQY FEWYTPNDGQ HWKRLQNDSA YLAEHGITAV WIPPAYKGTS        50
QADVGYGAYD LYDLGEFHQK GTVRTKYGTK GELQSAIKSL HSRDINVYGD       100
VVINHKGGAD ATEDVTAVEV DPADRNRVIS GEYLIKAWTH FHFPGRGSTY       150
SDFKWHWYHF DGTDWDESRK LNRIYKFQGK AWDWEVSSEN GNYDYLMYAD       200
IDYDHPDVVA EIKRWGTWYA NELQLDGFRL DAVKHIKFSF LRDWVNHVRE       250
KTGKEMFTVA EYWQNDLGAL ENYLNKTNFN HSVFDVPLHY QFHAASTQGG       300
GYDMRKLLNG TVVSKHPLKS VTFVDNHDTQ PGQSLESTVQ TWFKPLAYAF       350
ILTRESGYPQ VFYGDMYGTK GDSQREIPAL KHKIEPILKA RKQYAYGAQH       400
DYFDHHDIVG WTREGDSSVA NSGLAALITD GPGGAKRMYV GRQNAGETWH       450
DITGNRSEPV VINSEGWGEF HVNGGSVSIY VQR
```

Example 7

Modification of *B. licheniformis* Wild-Type Teramyl

Another α-amylase contemplated is the modification of the *B. licheniformis* wild-type Teramyl amylase (see e.g., WO 02/10355). This α-amylase has a K23R substitution. The sequence below depicts the mature Teramyl amylase.

Another variant could be a R23K form with the substitution at $X_2$ or a sequence wherein the R occurs at residue 23 in the mature form. It would involve substituting the first residue of the mature α-amylase (the underlined alanine) with any amino acid other than alanine or valine. The first residue in the mature polypeptide is actually residue 30 in the pre-protein. Another modification would be to substitute the first residue (the underlined alanine) with two, three, four, or five residues for that alanine, wherein the first of those residues are an amino acid other than alanine or valine. Yet another example would be the substitution of a threonine for the underlined alanine. The polypeptide could then be synthesized as described herein or known in the art.

```
                                             (SEQ ID NO: 11)
ANLNGTLMQY FEWYMPNDGQ HWRRLQNDSA YLAEHGITAV
WIPPAYKGTS QADVGYGAYD LYDLGEFHQK GTVRTKYGTK
GELQSAIKSL HSRDINVYGD VVINHKGGAD ATEDVTAVEV
DPADRNRVIS GEHLIKAWTH FHFPGRGSTY SDFKWHWYHF
DGTDWDESRK LNRIYKFQGK AWDWEVSNEN GNYDYLMYAD
IDYDHPDVAA EIKRWGTWYA NELQLDGFRL DAVKHIKFSF
LRDWVNHVRE KTGKEMFTVA EYWQNDLGAL ENYLNKTNFN
HSVFDVPLHY QFHAASTQGG GYDMRKLLNG TVVSKHPLKS
VTFVDNHDTQ PGQSLESTVQ TWFKPLAYAF ILTRESGYPQ
VFYGDMYGTK GDSQREIPAL KHKIEPILKA RKQYAYGAQH
DYFDHHDIVG WTREGDSSVA NSGLAALITD GPGGAKRMYV
GRQNAGETWH DITGNRSEPV VINSEGWGEF HVNGGSVSIY
VQR
```

Example 8

Modification of Teramyl SC/Liquozyme® Sc Sequence

Another α-amylase contemplated for mutation at X$_2$ (underlined alanine in the mature sequence) is the Termamyl SC/Liquozyme® Sc sequence, which can be used for starch processing. It would involve substituting the first residue (the underlined alanine) with any amino acid other than alanine or valine. Another modification would be to substitute two, three, four, or five residues for that alanine, wherein the first of those residues are an amino acid other than alanine or valine. The polypeptide could then be synthesized as described herein or known in the art.

```
                                               (SEQ ID NO: 12)
AAPFNGTMMQ  YFEWYLPDDG  TLWTKVANEA  NNLSSLGITA

LWLPPAYKGT  SRSDVGYGVY  DLYDLGEFNQ  KGTVRTKYGT

KAQYLQAIQA  AHAAGMQVYA  DVVFDHKGGA  DGTEWVDAVE

VNPSDRNQEI  SGTYQIQAWT  KFDFPGRGNT  YSSFKWRWYH

FDGVDWDESR  KLSRIYKFRG  KAWDWEVDTE  FGNYDYLMYA

DLDMDHPEVV  TELKNWGKWY  VNTTNIDGFR  LDAVKHIKFS

FFPDWLSYVR  SQTGKPLFTV  GEYWSYDINK  LHNYITKTNG

TMSLFDAPLH  NKFYTASKSG  GAFDMRTLMT  NTLMKDQPTL

AVTFVDNHDT  EPGQALQSWV  DPWFKPLAYA  FILTRQEGYP

CVFYGDYYGI  PQYNIPSLKS  KIDPLLIARR  DYAYGTQHDY

LDHSDIIGWT  REGGTEKPGS  GLAALITDGP  GGSKWMYVGK

QHAGKVFYDL  TGNRSDTVTI  NSDGWGEFKV  NGGSVSVWVP

RKTTVS
```

Example 9

Liquefaction Assay Comparing FRED A1T to Spezyme® FRED

The wild type α-amylase, Spezyme® FRED, was compared to the A1T mutant in a standard liquefaction assay, as well as assay under low pH and an assay under lower calcium conditions.

Materials and Methods.

Four A1T samples were assessed as compared to the wild-type. The amylase was fermented in *Pseudomonas*. The following materials were used:

Cargill bag starch, Lot. No. RM 228B D

Clinton Brand 106B Pearl corn starch, Lot. No. CS4 C20 076 106

TSL 06.275 blip A1T 20060100 (clarified), activity: 18,392, LU/g

TSL 06.276 blip A1T 20060101 (clarified), activity: 20,832, LU/g

TSL 06.277 blip A1T 20068013 (whole cell), activity: 16,969, LU/g

TSL 06.278 blip A1T 20068013 (clarified), activity: 22,154, LU/g

Spezyme® (lab standard), Lot No. 107-05190-001, activity: 19,678 LU/g

Sulfurous acid, JT Baker, Lot No. L14635

Calcium chloride, Fisher, Lot No. 006902

For each set of liquefactions, a 35% dry solid (ds) slurry of corn starch was made by adding 4666.67 g of Cargill bag starch to 7333.33 g reverse osmosis (RO) treated water. To this slurry, 100 ppm of SO$_2$ was added using 15.385 g of 6.5% sulfurous acid. Calcium was added when required as a calcium chloride dihydrate. The slurries were pH adjusted with 20% sodium carbonate to the desired pH (either 5.8 or 5.4). The slurry was then filtered through a 100-mesh sieve and split into 2000 g portions. Each slurry was dosed with 10 LU/g, either Spezyme® (standard Lot No. 107-05190-001) or the appropriate A1T sample approximately 10 minutes prior to being pumped through the bench cooker. The slurries were pumped through the bench cooker at a rate of approximately 43.33 mL/min to achieve a hold time of 9 minutes at a temperature of 109° C. Liquefact was then collected in a 500 mL Erlenmeyer flask, and held in a 95° C. bath for 120 minutes for secondary liquefaction. Samples were collected at 30, 60, 90, and 120 minutes. DE was determined using the Schoorl's reducing sugar method. The Schoorl method of reducing sugar is an assay based on the reduction of copper (II) ion to copper (I) by the presence of reducing sugars and a known excess of copper (II) ion. The remaining copper (II) ion concentration then reduces the iodide ion in an acetic media forming the triiodide ion. The triiodide ion is then titrated with a standardized thiosulfate solution. The specific materials and methods used are as follows: 10 mL wide mouth pipet, 250 mL Erlenmeyer flask, automatic dispensing pipettors with reservoir (10 mL and 2 mL), rheostat heater, clamp, flask, safety tongs, Fehlings solutions A & B, potassium iodide solution (30% w/v), sulfuric acid solution (26% w/v), sodium thiosulfate (0.1 N) standardized, starch indicator solution, glucose (1.00% w/v standardized). The potassium iodide solution (30% w/v) was prepared by dissolving 150 g KI in 40 mL distilled water, adding 1.5 mL 1 N NaOH, and quantitatively transferring to a 500 mL volumetric flask and bringing to the mark with distilled water. Sulfuric acid (26% w/v) was prepared as follows: with gentle agitation, slowly add 72.f mL concentrated sulfuric acid (S.G. 1.84) to 400 mL distilled water in a 600 mL beaker. Cool to room temperature. Quantitatively transfer to a 500 mL volumetric flask and bring to the mark with distilled water. The starch indicator solution was prepared by dissolving 150 g NaCl in 300 mL distilled water and heating to boiling. A slurry of starch in cold distilled water was then prepared containing 5 g (dry weight) of soluble starch. While agigating the hot NaCl solution, slowly add to the stach slurry. Bring the combined mixture to a boil for about 5 minutes and then cool to room temperature. Quantitatively transfer to a 500 mL volumetric flask and bring to the mark with distilled water. Not all the salt will dissolve. The standardized glucose, standardized sodium thiosulfate and Fehlings solutions were purchased.

The Schrool procedure is as follows. Thoroughly warm up the heater and adjust to bring 50 mL of water to a boil in 3 minutes. Obtain a sample of mash and prepare a dilution containing the equivalent of 47 to 67 mg dextrose per mL. For example, dilute about 15 g of liquefied mash (with DE=10-12) or 4 g of saccharified mash (with DE=50-60) to 100 mL. Determine the % solids (% S) of the diluted sample. Tare a 250 mL Erlenmeyer flask. Pipet 10 mL of diluted sample into the flask and weigh (F+S). With mixing, add 15 mL distilled water, then 10 mL Fehlings solution A, and 10 mL Fehlings solution B. Bring the mixture to a boil on the heater in 3 minutes (+/−15 seconds). Continue boiling for about 2 more minutes. Cool immediately under running tap water. With mixing, add 10 mL 30% potassium iodide and then 10 mL 26% sulfuric acid. Add 2 mL starch indicator and mix. Titrate immediately with 0.1 N sodium thiosulfate until the blue starch-iodine complex disappears. The blue color should not reappear for at least one minute. Record the tirtration volume (TVs). For a standard pipet 5.00 mL of 1.00% glucose and 20 mL distilled water into a 250 mL Erlenmeyer flask. The water blank used was 25 mL of distilled water into another flask. The steps were repeated starting at the step where with mixing 15 mL distilled water was added along with the 10 mL each of Fehlings Solutions A and B. The calculation is as follows:

$$\% \, DE = \frac{5 \times (TV_{wb} - TV_s) \times 100}{\% \, S \times [(F+S) - F] \times (TV_{wb} - TV_{std})}$$

Results.

Each of the four samples had improved DE progression over Spezyme® FRED when liquefied using a bench cooker at 109° C. with a hold time of 9 minutes. Both the Spezyme® FRED and A1T FRED variant at pH 5.4 had significantly however DE (dextrose equivalents) development than 5.8. The addition of 10 ppm calcium to the starch slurry did not have a significant effect on liquefaction for either Spezyme® FRED or the A1T variant. It was concluded that the native calcium content of the starch was apparently high enough to stabilize each of the enzymes at a pH of 5.8.

TABLE 3

| Enzyme | Lot# | pH | temp. ° C. | primary minutes | added calcium | DE 30 min. | 60 min. | 90 min. | 120 min |
|---|---|---|---|---|---|---|---|---|---|
| FRED std. | 107-05190-001 | 5.8 | 109 | 9 | 10 ppm | 4.27 | 7.37 | 9.61 | 11.15 |
| A1T | 20060100 | 5.8 | 109 | 9 | 10 ppm | 4.54 | 7.29 | 10.03 | 12.58 |
| A1T | 20060101 | 5.8 | 109 | 9 | 10 ppm | 4.60 | 7.24 | 9.98 | 12.42 |
| A1T | 20068013WC | 5.8 | 109 | 9 | 10 ppm | 4.78 | 7.20 | 10.24 | 12.62 |
| A1T | 20068013 | 5.8 | 109 | 9 | 10 ppm | 4.60 | 7.54 | 9.82 | 11.91 |
| Spezyme ® | 107-05190-001 | 5.8 | 109 | 9 | 0 | 4.66 | 7.07 | 9.18 | 11.21 |
| A1T | 20060100 | 5.8 | 109 | 9 | 0 | 4.66 | 7.56 | 9.84 | 12.26 |
| A1T | 20060101 | 5.8 | 109 | 9 | 0 | 4.68 | 7.20 | 9.82 | 12.27 |
| A1T | 20068013WC | 5.8 | 109 | 9 | 0 | 4.63 | 7.68 | 9.93 | 12.43 |
| A1T | 20068013 | 5.8 | 109 | 9 | 0 | 4.52 | 7.13 | 9.57 | 11.94 |
| Spezyme ® | 107-05190-001 | 5.4 | 109 | 9 | 0 | 3.93 | 5.67 | 7.72 | 9.66 |
| A1T | 20060100 | 5.4 | 109 | 9 | 0 | 4.39 | 7.19 | 9.06 | 11.08 |
| A1T | 20060101 | 5.4 | 109 | 9 | 0 | 4.28 | 6.29 | 8.63 | 10.50 |
| A1T | 20068013WC | 5.4 | 109 | 9 | 0 | 4.26 | 6.61 | 8.87 | 11.04 |
| A1T | 20068013 | 5.4 | 109 | 9 | 0 | 3.94 | 6.24 | 8.44 | 10.57 |

Figure 4:
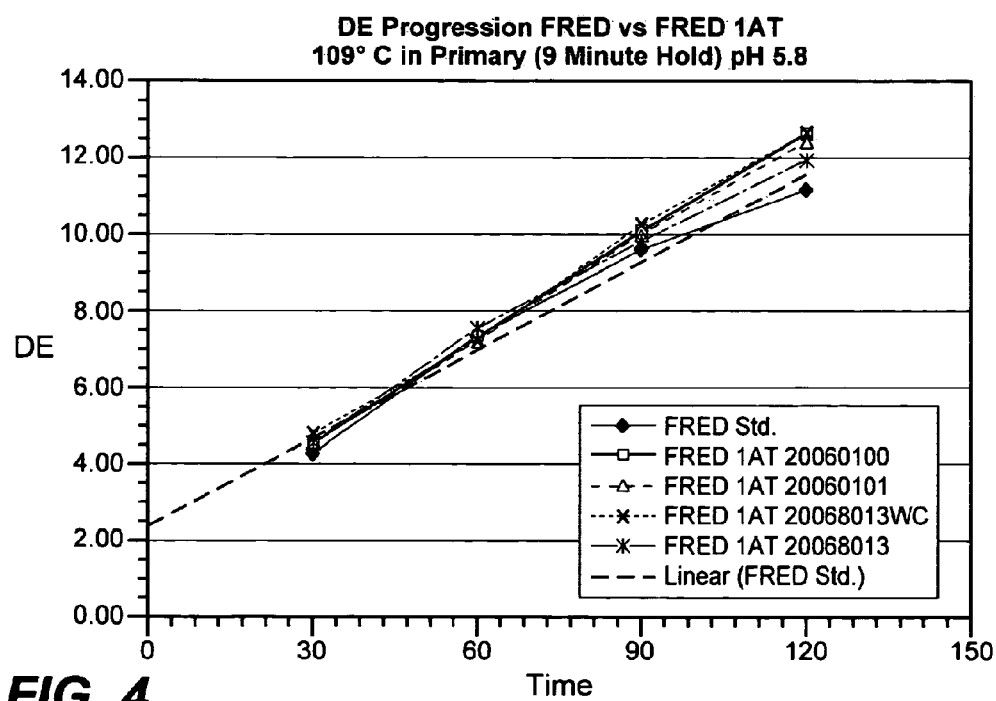
FIG. 4 depicts DE progression of Spezyme® FRED as compared to the A 1 T variant when the assay was performed at pH 5.8.
Figure 5:
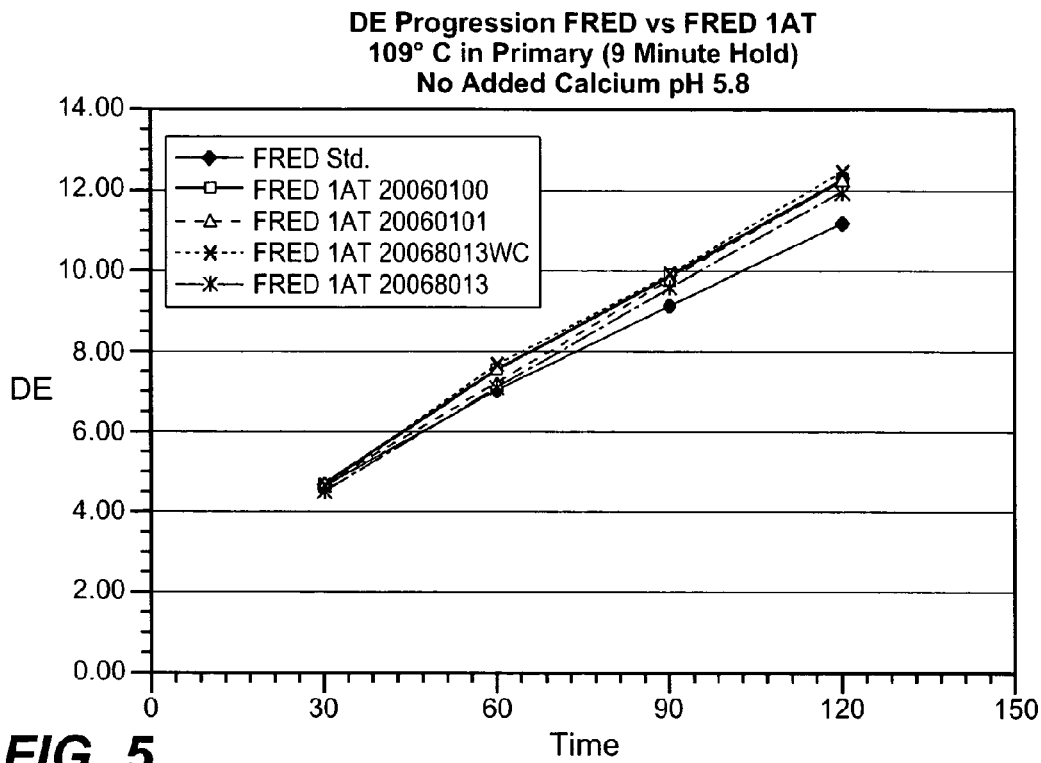
FIG. 5 depicts DE progression of Spezyme® FRED as compared to the A 1 T variant with no calcium added at pH 5.8.

The data shows that all of the A1T samples performed better at these conditions than the Spezyme® standard. The A1T whole cell sample performed better than its clarified counter part. It is unclear why the Spezyme® standard produced an uncharacteristic bend in the regression line, indicating that the enzyme was denatured over the course of the 120-minute secondary. FIG. 4 shows the DE progression of the A1T samples without the addition of calcium; FIG. 5 shows that the DE progression was not significantly effected with the addition of the 10 ppm, but that the A1T still performed better than the Spezyme® control.

Figure 6:
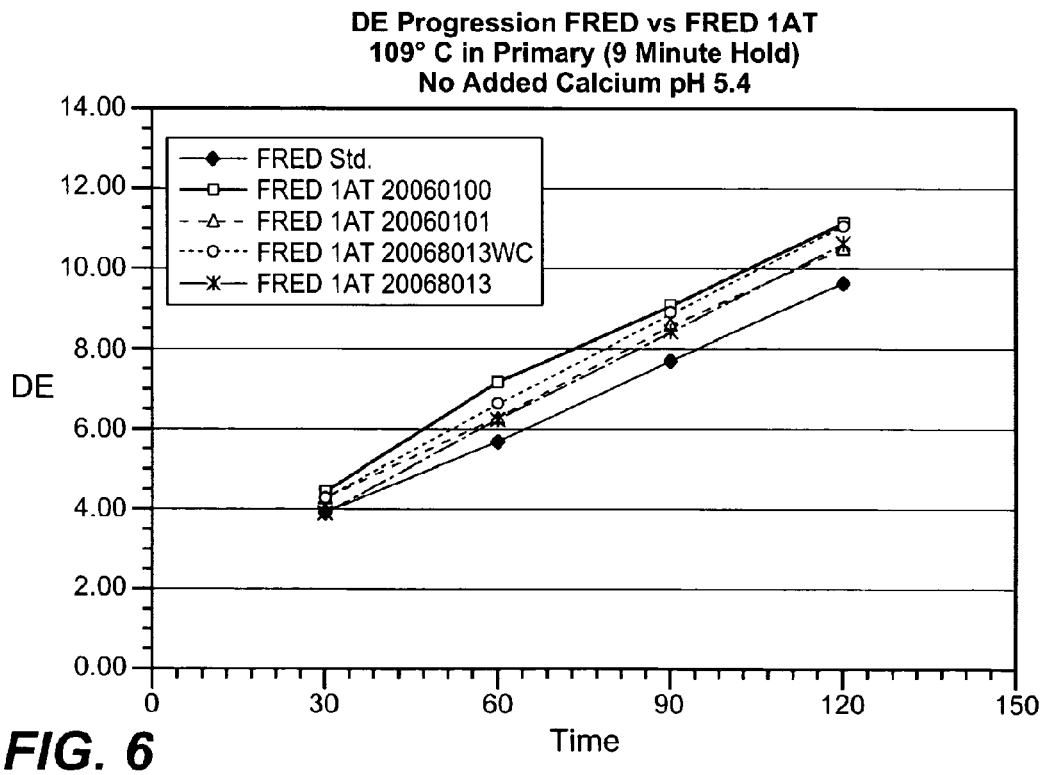
FIG. 6. Spezyme® FRED (wild-type) as compared to the A1T variant without additional calcium but at a pH of 5.4.

When the pH was changed to pH 5.4 (no addition of calcium), there was a slight decrease of stability for both enzymes (FIG. 6). However, the A1T samples were on average less effected by the pH decrease than the Spezyme® control.

All references cited above are herein incorporated by reference in their entirety for all purposes.

What is claimed is:

1. An isolated, mature amylase variant polypeptide comprising an amino acid sequence selected from the group consisting of SEQ ID NO: 9, 10, 11 and 12, wherein the first amino acid residue of SEQ ID NO: 9, 10, 11 and 12 is replaced by any amino acid other than alanine or valine, wherein said isolated, mature amylase variant has amylase activity.

2. The isolated, mature amylase variant polypeptide of claim 1, wherein said first amino acid residue of SEQ ID NO:9, 10, 11 and 12 is replaced by a threonine residue.

3. A detergent additive comprising the isolated, mature amylase variant of claim 1, optionally in the form of a non-dusting granulate, stabilized liquid, or protected enzyme.

4. The detergent additive of claim 3, wherein said detergent additive further comprises an enzyme selected from the group consisting of a cellulase, a protease, and an amylase.

5. The detergent additive of claim 4, wherein said amylase is an α-amylase, a β-amylase, or a glucoamylase.

6. A detergent composition comprising the isolated, mature amylase variant of claim 1.

7. A detergent composition comprising the detergent additive of claim 3.

8. The detergent composition of claim 6, further comprising an enzyme, where said enzyme is a protease, a lipase, a peroxidase, an amylase, a cellulase, a mannanase, a pectate lyase, or a combination of said enzymes.

9. A desizing composition comprising the isolated, mature amylase variant of claim 1 in an aqueous solution and optionally further comprising an additional enzyme.

10. A starch processing composition comprising the isolated, mature amylase variant of claim 1 in an aqueous solution.

11. The starch processing composition of claim 10 further comprising a glucoamylase, an isoamylase, a pullanase, or a combination thereof.

12. A method of processing a starch comprising administering the composition of claim 10 to a starch for a time sufficient to liquefy said starch.

13. A biofilm hydrolyzing composition comprising the isolated, mature amylase variant of claim 1, wherein said composition is in a solution or gel, and optionally further comprises a cellulase, a hemicellulase, a xylanase, a lipase, a protease, a pectinase, an antimicrobial agent, or a combination thereof.

14. A method of hydrolyzing a biofilm comprising administering the composition of claim 13 to a biofilm for a period of time sufficient to partially or fully hydrolyze said biofilm.

15. A method of saccharifying starch comprising administering the composition of claim 10 to a starch for a period of time sufficient to saccharify said starch.

* * * * *